US009461251B2

(12) United States Patent
Kawamura et al.

(10) Patent No.: US 9,461,251 B2
(45) Date of Patent: Oct. 4, 2016

(54) ANTHRACENE DERIVATIVE AND ORGANIC ELECTROLUMINESCENCE DEVICE USING THE SAME

(71) Applicants: Idemitsu Kosan Co., Ltd., Chiyoda-ku (JP); Sony Corporation, Tokyo (JP)

(72) Inventors: Masahiro Kawamura, Sodegaura (JP); Takashi Obikawa, Tokyo (JP); Shigeyuki Matsunami, Tokyo (JP); Ichinori Takada, Tokyo (JP); Yasunori Kijima, Tokyo (JP)

(73) Assignees: IDEMITSU KOSAN CO., LTD., Chiyoda-ku (JP); SONY CORPORATION, Tokyo (JP)

( * ) Notice: Subject to any disclaimer, the term of this patent is extended or adjusted under 35 U.S.C. 154(b) by 501 days.

(21) Appl. No.: 13/955,814

(22) Filed: Jul. 31, 2013

(65) Prior Publication Data

US 2013/0313538 A1 Nov. 28, 2013

Related U.S. Application Data

(63) Continuation of application No. 12/124,816, filed on May 21, 2008, now Pat. No. 8,512,875.

(30) Foreign Application Priority Data

May 21, 2007 (JP) ................................ 2007-134524

(51) Int. Cl.

| | |
|---|---|
| ***H01L 51/54*** | (2006.01) |
| ***C09K 11/06*** | (2006.01) |
| ***H01L 51/00*** | (2006.01) |
| ***C07D 307/79*** | (2006.01) |
| ***C07D 307/91*** | (2006.01) |
| ***C07D 333/76*** | (2006.01) |
| ***H05B 33/14*** | (2006.01) |
| ***C09B 57/00*** | (2006.01) |
| ***C09B 1/00*** | (2006.01) |
| *H01L 51/50* | (2006.01) |

(52) U.S. Cl.

CPC ......... *H01L 51/0074* (2013.01); *C07D 307/79* (2013.01); *C07D 307/91* (2013.01); *C07D 333/76* (2013.01); *C09B 1/00* (2013.01); *C09B 57/00* (2013.01); *C09K 11/06* (2013.01); *H01L 51/0052* (2013.01); *H01L 51/0058* (2013.01); *H01L 51/0073* (2013.01); *H05B 33/14* (2013.01); *C09K 2211/1011* (2013.01); *C09K 2211/1088* (2013.01); *C09K 2211/1092* (2013.01); *H01L 51/006* (2013.01); *H01L 51/0059* (2013.01); *H01L 51/0081* (2013.01); *H01L 51/5012* (2013.01)

(58) Field of Classification Search

None

See application file for complete search history.

(56) References Cited

U.S. PATENT DOCUMENTS

| | | | |
|---|---|---|---|
| 2005/0123787 | A1 | 6/2005 | Robello et al. |
| 2005/0123796 | A1 | 6/2005 | Giesen et al. |
| 2007/0055085 | A1 | 3/2007 | Kubota et al. |
| 2007/0247063 | A1 | 10/2007 | Murase et al. |
| 2008/0111478 | A1 | 5/2008 | Lyu et al. |
| 2009/0096356 | A1 | 4/2009 | Murase et al. |

FOREIGN PATENT DOCUMENTS

| | | | |
|---|---|---|---|
| CN | 1984897 | A | 6/2007 |
| EP | 1 707 550 | A1 | 10/2006 |
| EP | 1 748 045 | A1 | 1/2007 |
| EP | 2 100 941 | A2 | 9/2009 |
| EP | 2 213 640 | A1 | 8/2010 |
| JP | 2000-192028 | | 7/2000 |
| JP | 2004-2351 | | 1/2004 |
| JP | 2007-63501 | | 3/2007 |
| JP | 2007/77094 | | 3/2007 |
| JP | 2007-238500 | | 9/2007 |
| WO | WO 2005/054162 | A1 | 6/2005 |
| WO | WO 2005/113531 | A1 | 12/2005 |
| WO | 2007/029798 | | 3/2007 |
| WO | WO 2009/099133 | A1 | 8/2009 |
| WO | WO 2009/133917 | A1 | 11/2009 |

OTHER PUBLICATIONS

Extended Search Report issued Oct. 8, 2010, in European Patent Application No. 08752968.1-2101/2163550.

*Primary Examiner* — Andrew K Bohaty

(74) *Attorney, Agent, or Firm* — Oblon, McClelland, Maier & Neustadt, L.L.P.

(57) ABSTRACT

Provided are a novel anthracene derivative of a specific structure in which benzofuran or benzothiophene is bonded to anthracene through an arylene group, a material for an organic electroluminescence device and a light emitting material for an organic electroluminescence device each containing the anthracene derivative, and an organic electroluminescence device including an organic thin film layer formed of one or plural layers including at least a light emitting layer, the organic thin film layer being interposed between a cathode and an anode, in which at least one layer of the organic thin film layer contains the anthracene derivative alone or as a component of a mixture. The organic electroluminescence device has high luminous efficiency and is capable of emitting light with a long lifetime, and the device can be realized by the anthracene derivative.

19 Claims, No Drawings

ANTHRACENE DERIVATIVE AND ORGANIC ELECTROLUMINESCENCE DEVICE USING THE SAME

The present application is a Continuation application of U.S. application Ser. No. 12/124,816 which claims priority to Japanese Patent Application 2007-134524 having a filing date of May 21, 2007.

TECHNICAL FIELD

The present invention relates to an anthracene derivative and an organic electroluminescence (EL) device utilizing the derivative, in particular, an organic EL device having high luminous efficiency and capable of emitting light with a long lifetime, and an anthracene derivative for realizing the device.

BACKGROUND ART

An organic EL device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company (C. W. Tang and S. A. Vanslyke, Applied Physics Letters, Volume 51, Pages 913, 1987 or the like), many studies have been conducted on organic EL devices using organic materials as the constituent materials. Tang et al. used tris(8-hydroxyquinolinol aluminum) for a light emitting layer and a triphenyldiamine derivative for a hole transporting layer. Advantages of the laminate structure are that the efficiency of hole injection into the light emitting layer can be increased, that the efficiency of forming exciton which are formed by blocking and recombining electrons injected from the cathode can be increased, and that exciton formed within the light emitting layer can be enclosed. As described above, for the structure of the organic EL device, a two-layered structure having a hole transporting (injecting) layer and an electron transporting light emitting layer and a three-layered structure having a hole transporting (injecting) layer, a light emitting layer, and an electron transporting (injecting) layer are well known. To increase the efficiency of recombination of injected holes and electrons in the devices of the laminate type, the structure of the device and the process for forming the device have been studied.

Further, as the light emitting material, chelate complexes such as tris(8-quinolinolato)aluminum complexes, coumarine derivatives, tetraphenylbutadiene derivatives, bisstyrylarylene derivatives, and oxadiazole derivatives are known. It is reported that light in the visible region ranging from blue light to red light can be obtained by using these light emitting materials, and development of a device exhibiting color images is expected.

Further, in recent years, a large number of investigations have been conducted on the use of a phosphorescent compound as a light emitting material and the use of energy in a triplet state in EL light emission. A group of Princeton University has reported that an organic EL device using an iridium complex as a light emitting material shows high luminous efficiency. In addition to the organic EL device using a low molecular weight material as described above, an organic EL device using a conjugated polymer has been reported by a group of Cambridge University. In this report, light emission has been confirmed from a monolayer of polyphenylene vinylene (PPV) formed in a coating system.

Recent advances in organic EL device are remarkable, and characteristics of the organic EL device allow formation of a thin and lightweight light-emitting device with high luminance under application of a low voltage, wide range of emission wavelengths, and high-speed response, thereby suggesting the possibility of extensive uses.

In association with the significant progress of an organic light emitting device, performance requested of a light emitting material has been growing. For example, Patent Documents 1 to 6 each disclose an anthracene derivative. In addition, Patent Documents 7 to 10 each disclose an anthracene derivative containing dibenzofuran, dibenzothiophene, and a carbazole derivative. Each of those material systems shows improved performance, but involves, for example, the following problem: each of the systems still has low luminous efficiency. Accordingly, none of the systems has satisfied characteristics requested of a light emitting material needed to have an optical output with additionally high luminance or additionally high efficiency with which a voltage applied to the material is converted into light yet. In addition, a sufficient material, especially light emitting material, for an organic EL device having the following characteristics has not been found yet: the material meets requests for durability against, for example, a change over time due to the long-term use of an organic EL device containing the material or the deterioration of the device due to an atmospheric gas containing oxygen, moisture, or the like and for high-efficiency blue light emission taking the application of the device to, for example, a full-color display into consideration.

[Patent Document 1] US 2005/0089717 A
[Patent Document 2] U.S. Pat. No. 7,056,601
[Patent Document 3] WO 02/038524
[Patent Document 4] WO 2005/054162
[Patent Document 5] WO 2005/061656
[Patent Document 6] WO 2004/018587
[Patent Document 7] WO 04/053018
[Patent Document 8] JP 2005-314239 A
[Patent Document 9] JP 2007-063501 A
[Patent Document 10] WO 2005/113531

DISCLOSURE OF THE INVENTION

Problems to be Solved by the Invention

The present invention has been made with a view to solving the above-mentioned problems, and an object of the present invention is to provide an organic EL device having high luminous efficiency and capable of emitting light with a long lifetime, and a novel anthracene derivative for realizing the device.

Means for Solving the Problems

The inventors of the present invention have made extensive studies with a view to achieving the above-mentioned object. As a result, the inventors have found that the above-mentioned object can be achieved by using an anthracene derivative represented by the following general formula (1) in which benzofuran or benzothiophene is bonded to anthracene through an arylene group as a material for an organic EL device. Thus, the inventors have completed the present invention.

In other words, the present invention provides an anthracene derivative represented by the following general formula (1):

(1)

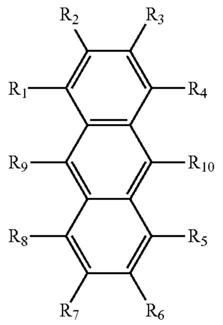

(In the formula, $R_1$ to $R_{10}$ each represent a hydrogen atom, a substituted or unsubstituted aliphatic hydrocarbon group having 1 to 12 ring carbon atoms, a substituted or unsubstituted aryl group having 6 to 60 ring carbon atoms, or a substituted or unsubstituted aromatic heterocyclic group having 5 to 60 ring carbon atoms, and at least one of $R_1$ to $R_{10}$ represents an aromatic heterocyclic derivative represented by the following general formula (a) or (a'):

(a)

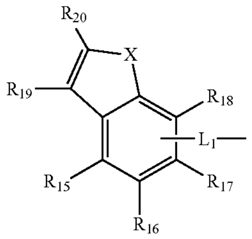

or (a')

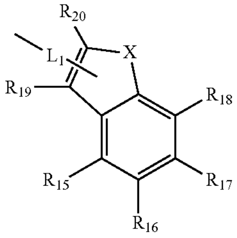

(In the formulae, where $L_1$ represents a substituted or unsubstituted arylene group having 6 to 30 ring carbon atoms, and $R_{15}$ to $R_{20}$ each represent a hydrogen atom or a substituent provided that a case where $L_1$ represents an anthrylene group is excluded, and X represents an oxygen atom (O) or a sulfur atom (S))).

In addition, the present invention provides a material for an organic EL device and a light emitting material for an organic EL device each containing the anthracene derivative, and an organic EL device including an organic thin film layer formed of one or more layers including at least a light emitting layer, the organic thin film layer being interposed between a cathode and an anode, in which at least one layer of the organic thin film layer contains the anthracene derivative alone or as a component of a mixture.

Effects of the Invention

An organic EL device using the anthracene derivative of the present invention as a material for an organic EL device has high luminous efficiency and a long lifetime.

BEST MODE FOR CARRYING OUT THE INVENTION

An anthracene derivative of the present invention is represented by the following general formula (1).

(1)

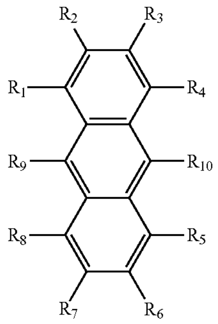

(In the formula, $R_1$ to $R_{10}$ each represent a hydrogen atom, a substituted or unsubstituted aliphatic hydrocarbon group having 1 to 12 ring carbon atoms, a substituted or unsubstituted aryl group having 6 to 60 ring carbon atoms, or a substituted or unsubstituted aromatic heterocyclic group having 5 to 60 ring carbon atoms, and at least one of $R_1$ to $R_{10}$ represents an aromatic heterocyclic derivative represented by the following general formula (a) or (a').

(a)

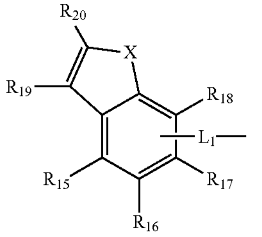

or (a')

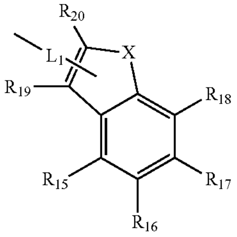

(In the formulae, $L_1$ represents a substituted or unsubstituted arylene group having 6 to 30 ring carbon atoms, and $R_{15}$ to $R_{20}$ each represent a hydrogen atom or a substituent provided that the case where $L_1$ represents an anthrylene group is excluded, and X represents an oxygen atom (O) or a sulfur atom (S).))

In the general formula (1), examples of the aliphatic hydrocarbon group having 1 to 12 ring carbon atoms represented by $R_1$ to $R_{10}$ include a methyl group, an n-propyl group, an isopropyl group, an n-butyl group, an isobutyl group, a t-butyl group, a pentyl group, an isopentyl group, a neopentyl group, a hexyl group, a cyclohexyl group, a heptyl group, an octyl group, a nonyl group, a decyl group, a vinyl group, a 2-butenyl group, a 3-pentenyl group, an ethinyl group, a propargyl group, and a 3-pentynyl group. Preferred are aliphatic hydrocarbon groups each having 1 to 6 carbon atoms and more preferred are a methyl group, a propyl group, a t-butyl group, and a cyclohexyl group.

In addition, examples of the aryl group having 6 to 60 ring carbon atoms represented by $R_1$ to $R_{10}$ include a phenyl group, a 1-naphthyl group, a 2-naphthyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, and a fluorenyl group.

Preferred are aryl groups each having 6 to 14 ring carbon atoms, and more preferred are a phenyl group, a 1-naphthyl group, a 2-naphthyl group, a 9-phenanthryl group, a 2-biphenylyl group, a 3-biphenylyl group, and a 4-biphenylyl group.

In addition, examples of the aromatic heterocyclic group having 5 to 60 ring carbon atoms represented by $R_1$ to $R_{10}$ include a 1-pyrrolyl group, a 2-pyrrolyl group, a 3-pyrrolyl group, a pyradinyl group, a 2-pyrizinyl group, a 3-pyrizinyl group, a 4-pyrizinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a 2-quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrole-1-yl group, a 2-methylpyrrole-3-yl group, a 2-methylpyrrole-4-yl group, a 2-methylpyrrole-5-yl group, a 3-methylpyrrole-1-yl group, a 3-methylpyrrole-2-yl group, a 3-methylpyrrole-4-yl group, a 3-methylpyrrole-5-yl group, a 2-t-butylpyrrole-4-yl group, a 3-(2-phenylpropyl)pyrrole-1-yl group, a 2-methyl-1-indolyl group, a 4-methyl-1-indolyl group, a 2-methyl-3-indolyl group, a 4-methyl-3-indolyl group, a 2-t-butyl1-indolyl group, a 4-t-butyl1-indolyl group, a 2-t-butyl3-indolyl group, and a 4-t-butyl3-indolyl group.

Preferred are a 2-pyrizinyl group, a 3-pyrizinyl group, a 4-pyrizinyl group, a 2-quinolyl group, a 3-quinolyl group, a 4-quinolyl group, a 5-quinolyl group, a 6-quinolyl group, a 7-quinolyl group, and an 8-quinolyl group.

Examples of the arylene group having 6 to 30 ring carbon atoms represented by $L_1$ in the general formula (a) or (a') include a phenylene group, a biphenylene group, a terphenylene group, a quarter phenylene group, a naphthylene group, a phenanthrylene group, a chrysenylene group, a pyrenylene group, a perylenylene group, and a fluorenylene group. Preferred are arylene groups each having 6 to 18 ring carbon atoms, more preferred are a phenylene group, a biphenylene group, a terphenylene group, a fluorenylene group, a naphthylene group, and a chrysenylene group, and more preferred are a phenylene group, a biphenylene group, and a naphthylene group.

Examples of the substituent in $R_1$ to $R_{10}$ and the substituent in $L_1$, or the substituent represented by $R_{15}$ to $R_{20}$ include aryl groups (having preferably 6 to 30 ring carbon atoms and more preferably 6 to 15 ring carbon atoms such as a phenyl group, a naphthyl group, a phenanthryl group, and a 9,9-dimethylfluorene-2-yl group), alkyl groups (having preferably 1 to 20 carbon atoms, more preferably 1 to 12 carbon atoms, and particularly preferably 1 to 8 carbon atoms such as methyl, ethyl, iso-propyl, tert-butyl, n-octyl, n-decyl, n-hexadecyl, cyclopropyl, cyclopentyl, and cyclohexyl), alkylsilyl groups (having preferably 1 to 20 carbon atoms and more preferably 1 to 10 carbon atoms such as a trimethylsilyl group and a triethylsilyl group), arylsilyl groups (having preferably 6 to 50 ring carbon atoms and more preferably 6 to 30 ring carbon atoms such as a triphenylsilyl group and a trinaphthylsilyl group), an alkenyl groups (having preferably 2 to 20 carbon atoms, more preferably 2 to 12 carbon atoms, and particularly preferably 2 to 8 carbon atoms such as vinyl, allyl, 2-butenyl, and 3-pentenyl), alkynyl groups (having preferably 2 to 20 carbon atoms, more preferably 2 to 12 carbon atoms, and particularly preferably 2 to 8 carbon atoms such as propargyl and 3-pentynyl), amino groups (having preferably 0 to 20 carbon atoms, more preferably 0 to 12 carbon atoms, and particularly preferably 0 to 6 carbon atoms such as amino, methylamino, dimethylamino, diethylamino, diphenylamino, and dibenzylamino), alkoxy groups (having preferably 1 to 20 carbon atoms, more preferably 1 to 12 carbon atoms, and particularly preferably 1 to 8 carbon atoms such as methoxy, ethoxy, and butoxy), aryloxy groups (having preferably 6 to 20 carbon atoms, more preferably 6 to 16 carbon atoms, and particularly preferably 6 to 12 carbon atoms such as phenyloxy and 2-naphthyloxy), acyl groups (having preferably 1 to 20 carbon atoms, more preferably 1 to 16 carbon atoms, and particularly preferably 1 to 12 carbon atoms such as acetyl, benzoyl, formyl, and pivaloyl), alkoxycarbonyl groups (having preferably 2 to 20 carbon atoms, more preferably 2 to 16 carbon atoms, and particularly preferably 2 to 12 carbon atoms such as methoxycarbonyl and ethoxycarbonyl), aryloxycarbonyl groups (having preferably 7 to 20 carbon atoms, more preferably 7 to 16 carbon atoms, and particularly preferably 7 to 10 carbon atoms such as phenyloxycarbonyl), acyloxy groups (having preferably 2 to 20 carbon atoms, more preferably 2 to 16 carbon atoms, and particularly preferably 2 to 10 carbon atoms such as acetoxy and benzoyloxy), acylamino groups (having preferably 2 to 20 carbon atoms, more preferably 2 to 16 carbon atoms, and particularly preferably 2 to 10 carbon atoms such as acetylamino and benzoylamino), alkoxycarbonylamino groups (having preferably 2 to 20 carbon atoms, more preferably 2 to 16 carbon atoms, and particularly preferably 2 to 12 carbon atoms such as methoxycarbonylamino), aryloxycarbonylamino groups (having preferably 7 to 20 carbon atoms, more preferably 7 to 16 carbon atoms, and particularly preferably 7 to 12 carbon atoms such as phenyloxycarbonylamino), sulfonylamino groups (having preferably 1 to 20 carbon atoms, more preferably 1 to 16 carbon atoms, and particularly preferably 1 to 12 carbon atoms such as methanesulfonylamino and benzenesulfonylamino), sulfamoyl groups (having preferably 0 to 20 carbon atoms, more preferably 0 to 16 carbon atoms, and particularly preferably 0 to 12 carbon atoms such as sulfamoyl, methylsulfamoyl, dimethylsulfamoyl, and phenylsulfamoyl), carbamoyl groups (having preferably 1 to 20 carbon atoms, more preferably 1 to 16 carbon atoms, and particularly preferably 1 to 12 carbon atoms such as carbamoyl, methylcarbamoyl, diethylcarbamoyl, and phenylcarbamoyl), alkylthio groups (having preferably 1 to 20 carbon atoms, more preferably 1 to 16 carbon atoms, and particularly preferably 1 to 12 carbon atoms such as methylthio and ethylthio), arylthio groups (having preferably 6 to 20 carbon atoms, more preferably 6 to 16 carbon atoms, and particularly preferably 6 to 12 carbon atoms such as phenylthio), sulfonyl groups (having preferably 1 to 20 carbon atoms, more preferably 1 to 16 carbon atoms, and particularly preferably 1 to 12 carbon atoms such as mesyl and tosyl), sulfinyl groups (having preferably 1 to 20 carbon atoms, more preferably 1 to 16 carbon atoms, and particularly preferably 1 to 12 carbon atoms such as methane sulfinyl and benzene sulfinyl), ureide groups (having preferably 1 to 20 carbon atoms, more preferably 1 to 16 carbon atoms, and particularly preferably 1 to 12 carbon atoms such as ureide, methyl ureide, and phenyl ureide), phosphoric amide groups (having preferably 1 to 20 carbon atoms, more preferably 1 to 16 carbon atoms, and particularly preferably 1 to 12 carbon atoms such as diethyl phosphoric amide and phenyl phosphoric amide), a hydroxy group, a mercapto group, halogen atoms (such as a fluorine atom, a chlorine atom, a bromine atoms, and an iodine atom), a cyano group, a sulfo group, a carboxyl group, a nitro group, a hydroxamic acid group, a sulfino group, a hydrazino group, an imino group, and heterocyclic group (having preferably 1 to 30 carbon atoms, and more preferably 1 to 12 carbon atoms, and a nitrogen atom, an oxygen atom, and sulfur atom as a hetero atom such as imidazolyl, pyridyl, quinolyl, furyl, thienyl, piperidyl, morpholino, benzooxazolyl, benzoimidazolyl, benzothiazolyl, and carbazolyl), and silyl groups (having preferably 3 to 40 carbon atoms, more preferably 3 to 30 carbon atoms, and particularly preferably 3 to 24 carbon atoms such as trimethylsilyl and triphenylsilyl).

Each of those substituents may be further substituted. In addition, when two or more substituents are present, the substituents may be identical to or different from each other, and, if possible, may be coupled to each other to form a ring.

Of those substituents, an aryl group, an alkyl group, an alkylsilyl group, an arylsilyl group, an alkenyl group, or an alkynyl group is preferable, and an aryl group, an alkyl group, an alkylsilyl group, or an arylsilyl group is more preferable.

The anthracene derivative of the present invention is preferably of a structure represented by any one of the following general formulae (2) to (7). An anthracene derivative represented by any one of the general formulae (2) to (6) out of those formulae is preferable, and an anthracene derivative represented by the general formula (3) or (5) out of those formulae is more preferable.

(2) An Anthracene Derivative Represented by the Following General Formula (2)

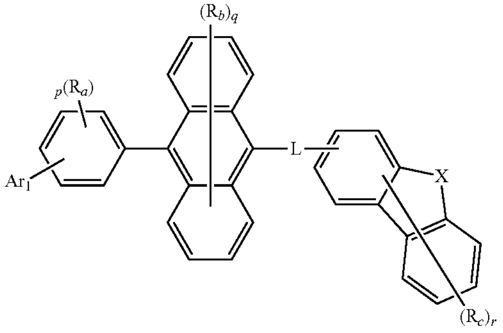

(2)

(In the formula, L represents a substituted or unsubstituted phenylene group, a substituted or unsubstituted naphthylene group, a substituted or unsubstituted phenanthrylene group, a substituted or unsubstituted fluorenylene group, or a substituted or unsubstituted biphenylene group, Ra to Rc each represent a hydrogen atom or a substituent, $Ar_1$ represents a substituted or unsubstituted aryl group having 6 to 20 ring carbon atoms, X represents an oxygen atom (O) or a sulfur atom (S), p represents an integer of 1 to 4, q represents an integer of 1 to 8, and r represents an integer of 1 to 7.)

Examples of the aryl group represented by $Ar_1$ include examples each having a compatible carbon number out of the examples of the aryl groups represented by any one of $R_1$ to $R_{10}$ of the general formula (1). Examples of the substituent in L, the substituent represented by any one of Ra to Rc, and the substituent of $Ar_1$ include examples similar to those of the substituent in any one of $R_1$ to $R_{10}$ and the substituent in $L_1$, or the substituent represented by any one of $R_{15}$ to $R_{20}$ in the general formula (1).

(3) An Anthracene Derivative Represented by the Following General Formula (3)

(3)

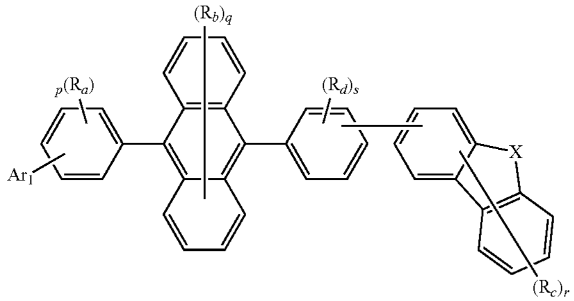

(In the formula, Ra to Rd each represent a hydrogen atom or a substituent, $Ar_1$ represents a substituted or unsubstituted aryl group having 6 to 20 ring carbon atoms, X represents an oxygen atom (O) or a sulfur atom (S), p represents an integer of 1 to 4, q represents an integer of 1 to 8, r represents an integer of 1 to 7, ands represents an integer of 1 to 4.)

Examples of the aryl group represented by $Ar_1$ include examples each having a compatible carbon number out of the examples of the aryl group represented by anyone of $R_1$ to $R_{10}$ of the general formula (1). Examples of the substituent in L, the substituent represented by any one of Ra to Rd, and the substituent of $Ar_1$ include examples similar to those of the substituent in any one of $R_1$ to $R_{10}$ of the general formula (1).

An anthracene derivative represented by any one of the following formulae (3)-1 to (3)-3 is preferable.

(3)-1

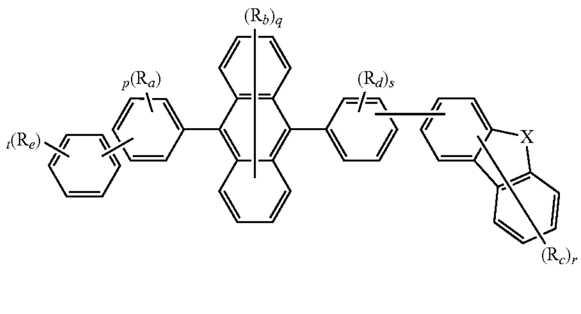

In the formula (3)-1, t represents an integer of 1 to 5, and Re has the same meaning as that of each of Ra to Rd.

(3)-2

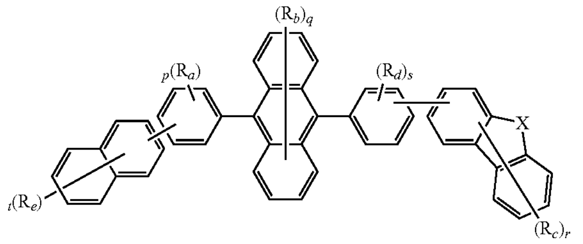

In the formula (3)-2, t represents an integer of 1 to 7, and Re has the same meaning as that of each of Ra to Rd.

(3)-3

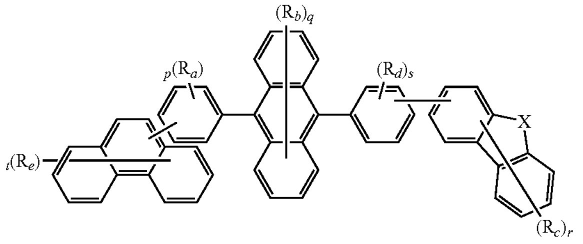

In the formula (3)-3, t represents an integer of 1 to 9, and Re has the same meaning as that of each of Ra to Rd.

(4) An Anthracene Derivative Represented by the Following General Formula (4)

(4)

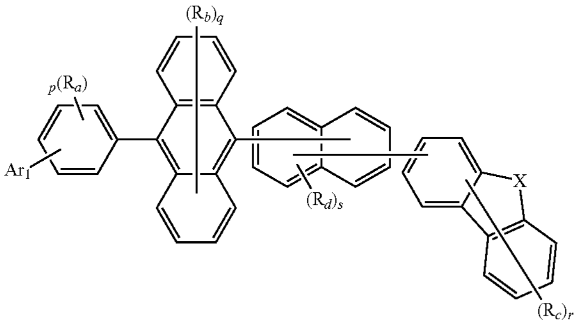

(In the formula, Ra to Rd each represent a hydrogen atom or a substituent, $Ar_1$ represents a substituted or unsubstituted aryl group having 6 to 20 ring carbon atoms, X represents an oxygen atom (O) or a sulfur atom (S), p represents an integer of 1 to 4, q represents an integer of 1 to 8, r represents an integer of 1 to 7, and s represents an integer of 1 to 6.)

Examples of the aryl group represented by $Ar_1$ include examples each having a compatible carbon number out of the examples of the aryl group represented by any one of $R_1$ to $R_{10}$ of the general formula (1). Examples of the substituent represented by any one of Ra to Rd and the substituent of $Ar_1$ include examples similar to those of the substituent in any one of $R_1$ to $R_{10}$ of the general formula (1).

An anthracene derivative represented by any one of the following formulae (4)-1 to (4)-3 is preferable.

(4)-1

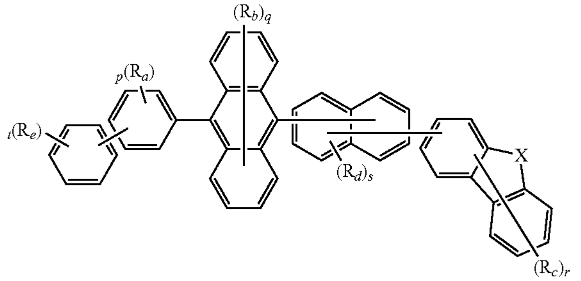

In the formula (4)-1, t represents an integer of 1 to 5, and Re has the same meaning as that of each of Ra to Rd.

(4)-2

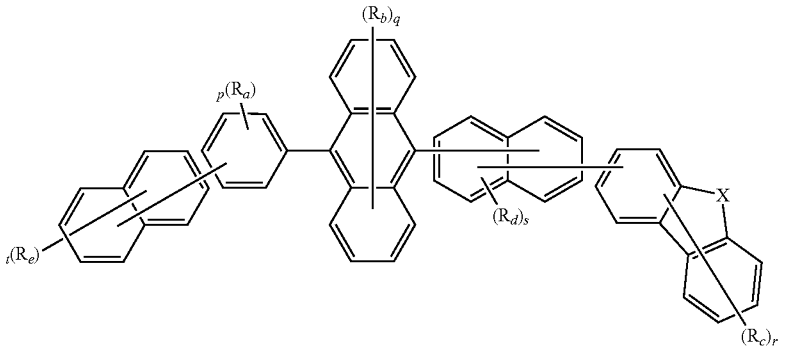

In the formula (4)-2, t represents an integer of 1 to 7, and Re has the same meaning as that of each of Ra to Rd.

(4)-3

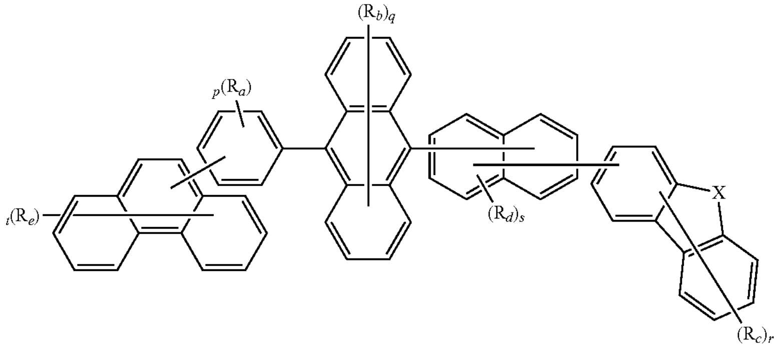

In the formula (4)-3, t represents an integer of 1 to 9, and Re has the same meaning as that of each of Ra to Rd.

(5) An Anthracene Derivative Represented by the Following General Formula (5)

(5)

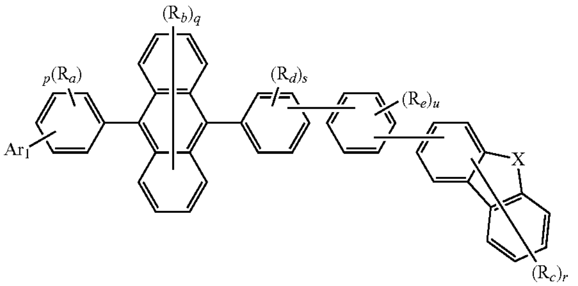

(In the formula, Ra to Re each represent a hydrogen atom or a substituent, $Ar_1$ represents a substituted or unsubstituted aryl group having 6 to 20 ring carbon atoms, X represents an oxygen atom (O) or a sulfur atom (S), p represents an integer of 1 to 4, q represents an integer of 1 to 8, r represents an integer of 1 to 7, s represents an integer of 1 to 6, and u represents an integer of 1 to 4.)

Examples of the aryl group represented by $Ar_1$ include examples each having a compatible carbon number out of the examples of the aryl group represented by any one of $R_1$ to $R_{10}$ of the general formula (1). Examples of the substituent represented by any one of Ra to Rd and the substituent of $Ar_1$ include examples similar to those of the substituent in any one of $R_1$ to $R_{10}$ of the general formula (1).

An anthracene derivative represented by any one of the following formulae (5)-1 to (5)-3 is preferable.

(5)-1

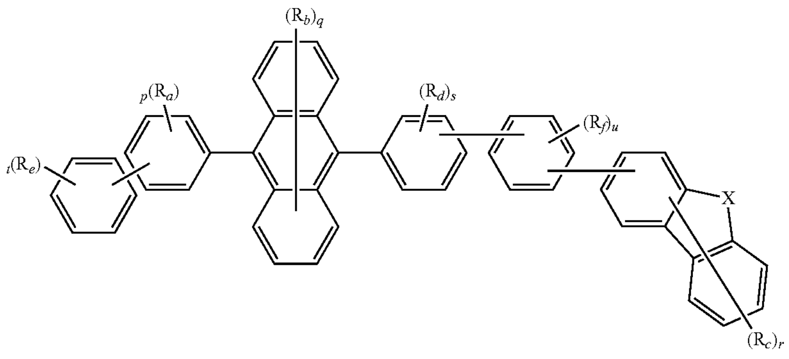

In the formula (5)-1, t represents an integer of 1 to 5, and Re has the same meaning as that of each of Ra to Rd.

(5)-2

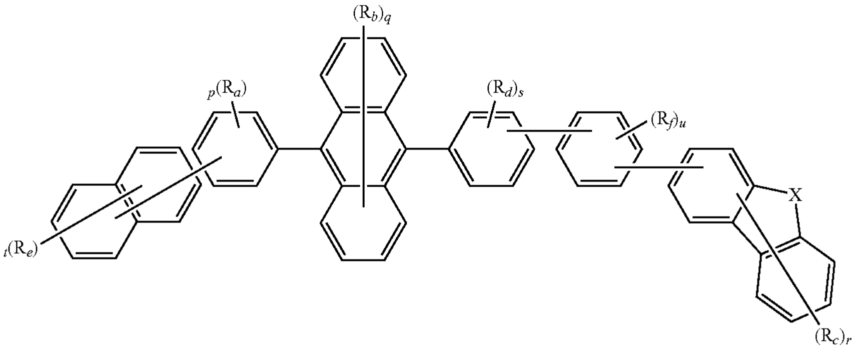

In the formula (5)-2, t represents an integer of 1 to 7, and Re has the same meaning as that of each of Ra to Rd.

(5)-3

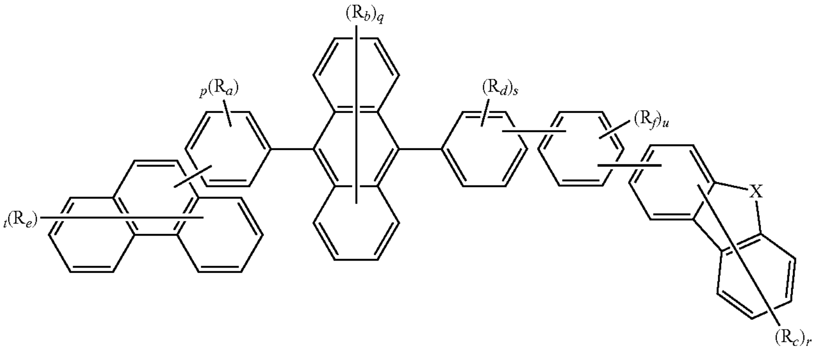

In the formula (5)-3, t represents an integer of 1 to 9, and Re has the same meaning as that of each of Ra to Rd.

(6) An Anthracene Derivative Represented by the Following General Formula (6)

(6)

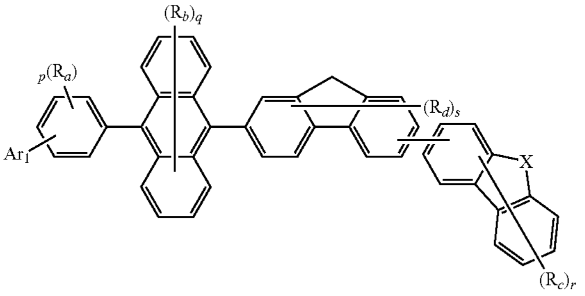

(In the formula, Ra to Rd each represent a hydrogen atom or a substituent, $Ar_1$ represents a substituted or unsubstituted aryl group having 6 to 20 ring carbon atoms, X represents an oxygen atom (O) or a sulfur atom (S), p represents an integer of 1 to 4, q represents an integer of 1 to 8, r represents an integer of 1 to 7, and s represents an integer of 1 to 8.)

Examples of the aryl group represented by $Ar_1$ include examples each having a compatible carbon number out of the examples of the aryl group represented by any one of $R_1$ to $R_{10}$ of the general formula (1). Examples of the substituent represented by any one of Ra to Rd and the substituent of $Ar_1$ include examples similar to those of the substituent in any one of $R_1$ to $R_{10}$ of the general formula (1).

An anthracene derivative represented by any one of the following formulae (6)-1 to (6)-3 is preferable.

(6)-1

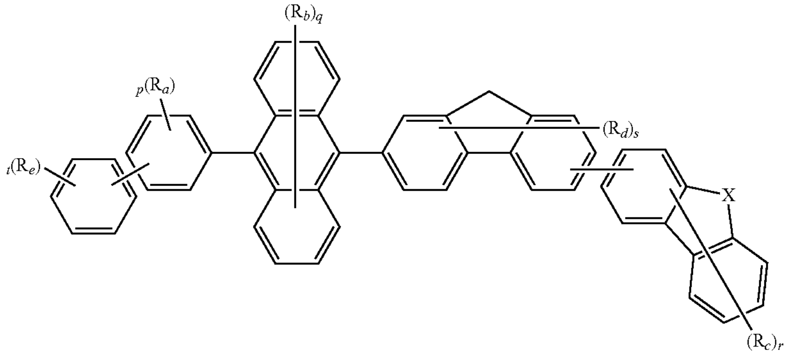

In the formula (6)-1, t represents an integer of 1 to 5, and Re has the same meaning as that of each of Ra to Rd.

(6)-2

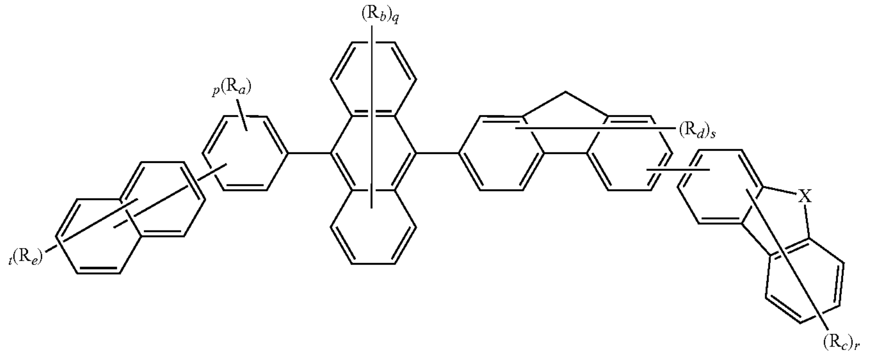

In the formula (6)-2, t represents an integer of 1 to 7, and Re has the same meaning as that of each of Ra to Rd.

(6)-3

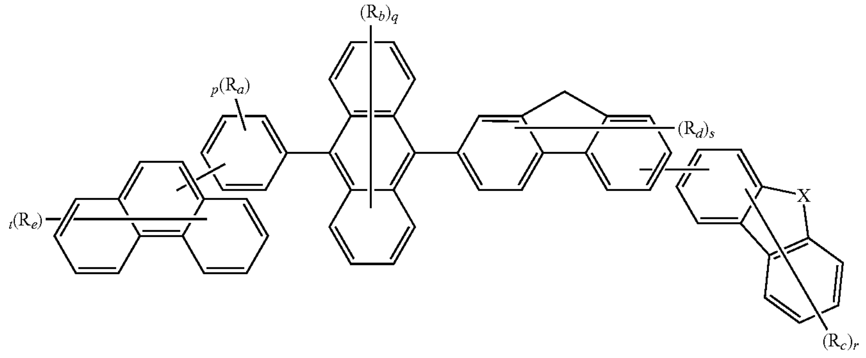

In the formula (6)-3, t represents an integer of 1 to 9, and Re has the same meaning as that of each of Ra to Rd.

(7) An Anthracene Derivative Represented by the Following General Formula (7)

(7)

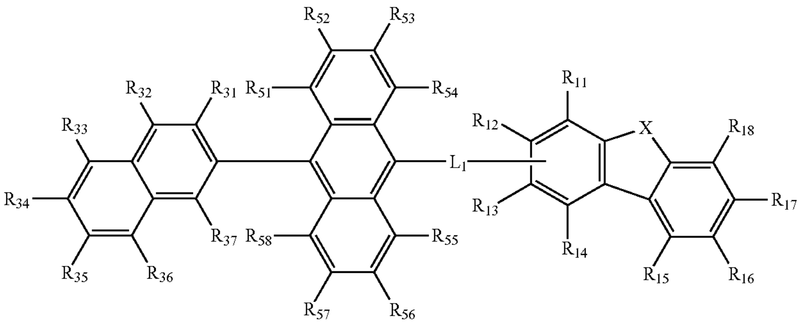

(In the formula, $L_1$ represents a substituted or unsubstituted arylene group having 6 to 30 ring carbon atoms provided that the case where $L_1$ represents an anthrylene group is excluded, $R_{11}$ to $R_{18}$ each represent a hydrogen atom or a substituent, and adjacent substituents of $R_{11}$ to $R_{18}$ may form a saturated or unsaturated ring, $R_{31}$ to $R_{37}$ and $R_{51}$ to $R_{58}$ each represent a hydrogen atom, an alkyl group having 1 to 10 carbon atoms, an alkoxy group having 1 to 10 carbon atoms, an aralkyl group having 7 to 20 carbon atoms, an aryloxy group having 6 to 20 carbon atoms, an alkynyl group having 2 to 20 carbon atoms, an alkylsilyl group having 1 to 20 carbon atoms, an arylsilyl group having 6 to 30 ring carbon atoms, an alkenyl group having 2 to 20 carbon atoms, a vinyl group having 8 to 20 carbon atoms, or an aryl group having 6 to 20 ring carbon atoms, and X represents an oxygen atom (O) or a sulfur atom (S).)

Specific examples of $L_1$ and $R_{11}$ to $R_{18}$ include examples similar to those of $L_1$ and $R_{15}$ to $R_{20}$ of the general formula (1). Specific examples of $R_{31}$ to $R_{37}$ and $R_{51}$ to $R_{58}$ include those described for $R_1$ to $R_{10}$ of the general formula (1) and the substituent of any one of them. Examples of the substituent in $L_1$ and the substituent in any one of $R_{31}$ to $R_{37}$ and $R_{51}$ to $R_{58}$ include examples similar to those of the substituent in any one of $R_1$ to $R_{10}$ of the general formula (1).

An anthracene derivative represented by any one of the following general formulae (8) to (12) is also preferable as the anthracene derivative of the present invention.

(8) An Anthracene Derivative Represented by the General Formula (8)

(8)

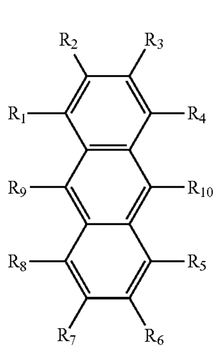

In the general formula (8), $R_1$ to $R_{10}$ each represent a hydrogen atom, a substituted or unsubstituted aliphatic hydrocarbon group having 1 to 12 ring carbon atoms, a substituted or unsubstituted aryl group having 6 to 60 ring carbon atoms, or a substituted or unsubstituted aromatic heterocyclic group having 5 to 60 ring carbon atoms, and at least one of $R_1$ to $R_{10}$ represents an aromatic heterocyclic derivative represented by the following general formula (a) or (a').

(a)

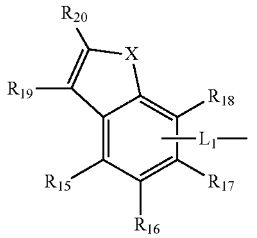

or (a')

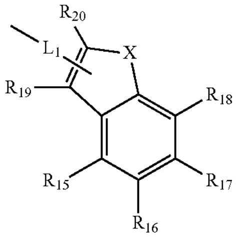

(In the formulae, $L_1$ represents a substituted or unsubstituted arylene group having 6 to 30 ring carbon atoms (provided that the case where $L_1$ represents an anthrylene group is excluded), $R_{15}$ to $R_{20}$ each represent a hydrogen atom or a substituent, and adjacent substituents of $R_{15}$ to $R_{20}$ may form a saturated or unsaturated ring (provided that the case where $R_{19}$ and $R_{20}$ in the general formula (a) form an unsaturated ring is excluded), and X represents an oxygen atom (O) or a sulfur atom (S).)

Those described for the general formula (1) correspond to specific examples of $R_1$ to $R_{10}$, $L_1$, and $R_{35}$ to $R_{20}$, and to the substituents of them.

(9) An Anthracene Derivative Represented by the Following General Formula (9)

(9)

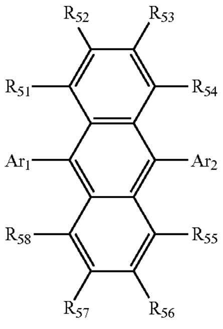

In the general formula (9), $R_{51}$ to $R_{58}$ each represent a hydrogen atom, or a substituted or unsubstituted aliphatic hydrocarbon group having 1 to 12 ring carbon atoms, and $Ar_1$ represents a substituted or unsubstituted aryl group having 6 to 60 ring carbon atoms (except a monosubstituted phenyl group substituted by an alkyl group, or a 1-naphthyl group), and $Ar_2$ is represented by the following general formula (b).

(b)

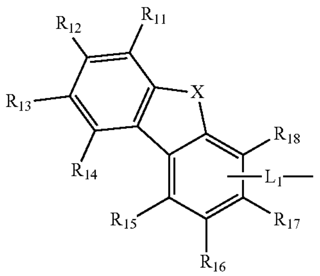

In the general formula (b), $L_1$ represents a phenylene group, X represents an oxygen atom (O) or a sulfur atom (S), $R_{11}$ to $R_{18}$ each represent a hydrogen atom or a substituent, and adjacent substituents of $R_{11}$ to $R_{18}$ may form a saturated or unsaturated ring.

Specific examples of $L_1$ and $R_{11}$ to $R_{18}$ include examples similar to those of $L_1$ and $R_{15}$ to $R_{20}$ of the general formula (1). Specific examples of $R_{51}$ to $R_{58}$ include examples similar to those of $R_1$ to $R_{10}$ of the general formula (1). Examples of the aryl group represented by $Ar_1$ include examples similar to those of the aryl group represented by any one of $R_1$ to $R_{10}$ of the general formula (1). Examples of the substituent in any one of $R_{11}$ to $R_{18}$ and $R_{51}$ to $R_{58}$ include examples similar to those of the substituent in any one of $R_1$ to $R_{10}$ of the general formula (1).

(10) An Anthracene Derivative Represented by the Following General Formula (10)

(10)

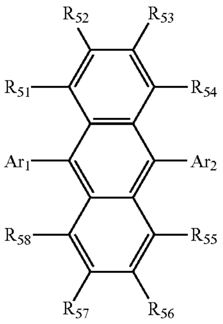

In the general formula (10), $R_{51}$ to $R_{58}$ each represent a hydrogen atom, or a substituted or unsubstituted aliphatic hydrocarbon group having 1 to 12 ring carbon atoms.

$Ar_1$ represents an unsubstituted aryl group having 6 to 60 ring carbon atoms, or a substituted aryl group having 6 to 60 ring carbon atoms (except a monosubstituted phenyl group substituted by an alkyl group, a monosubstituted naphthyl group substituted by a dibenzofuranyl group, or a 1-naphthyl group), and $Ar_2$ is represented by the following general formula (c).

(c)

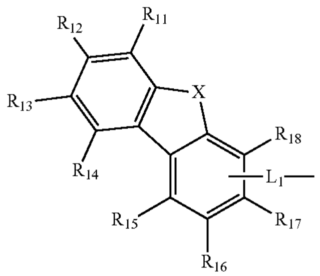

In the general formula (c), $L_1$ represents a naphthylene group, X represents an oxygen atom (O) or a sulfur atom (S), $R_{11}$ to $R_{18}$ each represent a hydrogen atom or a substituent, and adjacent substituents of $R_{11}$ to $R_{18}$ may form a saturated or unsaturated ring.

Specific examples of $R_{11}$ to $R_{18}$ include examples similar to those of $R_{15}$ to $R_{20}$ of the general formula (1). Specific examples of $R_{51}$ to $R_{58}$ include examples similar to those of $R_1$ to $R_{10}$ of the general formula (1). Examples of the aryl group represented by $Ar_1$ include examples similar to those of the aryl group represented by any one of $R_1$ to $R_{10}$ of the general formula (1). Examples of the substituent in any one of $Ar_1$, $R_{11}$ to $R_{18}$, and $R_{51}$ to $R_{58}$ include examples similar to those of the substituent in any one of $R_1$ to $R_{10}$ of the general formula (1).

(11) An Anthracene Derivative Represented by the Following General Formula (11)

to $R_{18}$, and $R_{41}$ to $R_{48}$ include examples similar to those of the substituent in any one of $R_1$ to $R_{10}$ of the general formula (1).

(12) An Anthracene Derivative Represented by the Following General Formula (12)

(12)

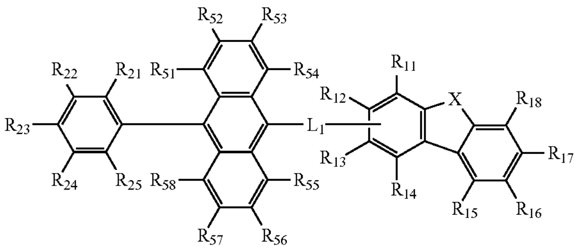

In the general formula (12), $L_1$ represents a substituted or unsubstituted arylene group having 6 to 30 ring carbon atoms (except an anthrylene group), X represents an oxygen atom (O) or a sulfur atom (S), $R_{11}$ to $R_{18}$ each represent a hydrogen atom or a substituent, and adjacent substituents of $R_{11}$ to $R_{18}$ may form a saturated or unsaturated ring, $R_{21}$ to $R_{25}$ each represent a hydrogen atom or a substituent, and adjacent substituents of $R_{21}$ to $R_{25}$ may form a saturated or unsaturated ring (provided that the case where $R_{23}$ represents a t-butyl group is excluded), and $R_{51}$ to $R_{58}$ each represent a hydrogen atom, or a substituted or unsubstituted aliphatic hydrocarbon group having 1 to 12 ring carbon atoms.

(11)

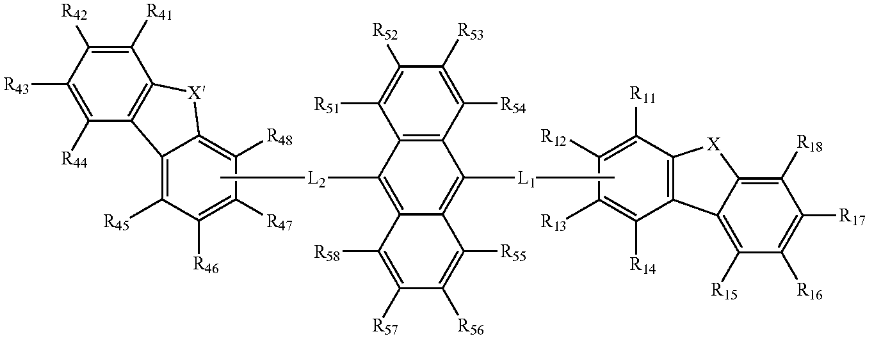

In the general formula (11), $L_1$ and $L_2$ each represent a substituted or unsubstituted phenylene group, $R_{11}$ to $R_{18}$ each represent a hydrogen atom or a substituent, and adjacent substituents of $R_{11}$ to $R_{18}$ may form a saturated or unsaturated ring, $R_{41}$ to $R_{48}$ each represent a hydrogen atom or a substituent, and adjacent substituents of $R_{41}$ to $R_{48}$ may form a saturated or unsaturated ring, $R_{51}$ to $R_{58}$ each represent a hydrogen atom, or a substituted or unsubstituted aliphatic hydrocarbon group having 1 to 12 ring carbon atoms, and X and X' each represent an oxygen atom (O) or a sulfur atom (S) provided that the case where both of $L_1$ and $L_2$ each represent a naphthylene group and both of X and X' each represent an oxygen atom (O) is excluded.

Specific examples of $R_{11}$ to $R_{18}$ and $R_{41}$ to $R_{48}$ include examples similar to those of $R_{15}$ to $R_{20}$ of the general formula (1). Specific examples of $R_{51}$ to $R_{58}$ include examples similar to those of $R_1$ to $R_{10}$ of the general formula (1). Examples of the substituent in any one of $L_1$ and $L_2$, $R_{11}$ Those described for the general formula (1) correspond to the substituent in $L_1$, the substituent in any one of $R_{51}$ to $R_{58}$, and the substituent represented by any one of $R_{11}$ to $R_{18}$ and $R_{21}$ to $R_{25}$.

Specific examples of $L_1$ include examples similar to those of $L_1$ of the general formula (1). Specific examples of $R_{11}$ to $R_{18}$ and $R_{21}$ to $R_{25}$ include examples similar to those of $R_{15}$ to $R_{20}$ of the general formula (1). Specific examples of $R_{51}$ to $R_{58}$ include examples similar to those of $R_1$ to $R_{10}$ of the general formula (1). Examples of the substituent in any one of $L_1$, $R_{11}$ to $R_{18}$, and $R_{21}$ to $R_{25}$ include examples similar to those of the substituent in any one of $R_1$ to $R_{10}$ of the general formula (1).

Examples of the ring which adjacent substituents may form in any one of the above general formulae include benzene, naphthalene, anthracene, and phenanthrene.

Hereinafter, specific examples of the compound of the present invention are shown. However, the compound is not limited to the following examples.

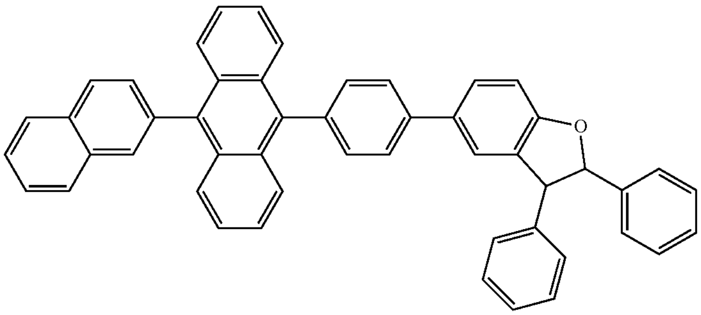
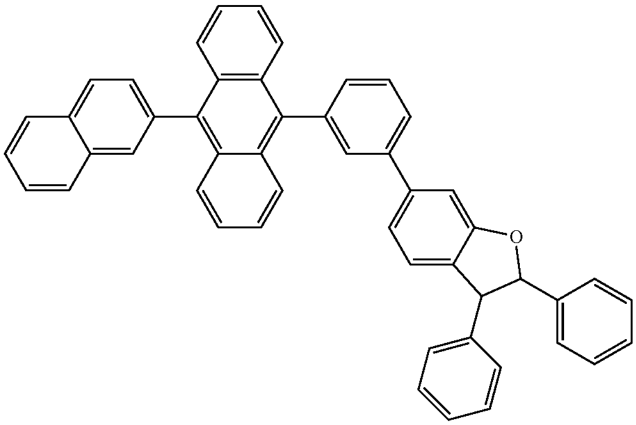
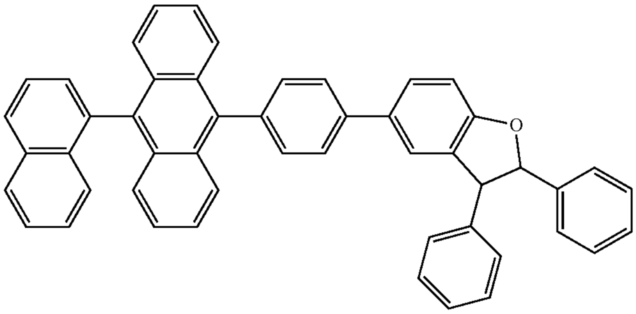
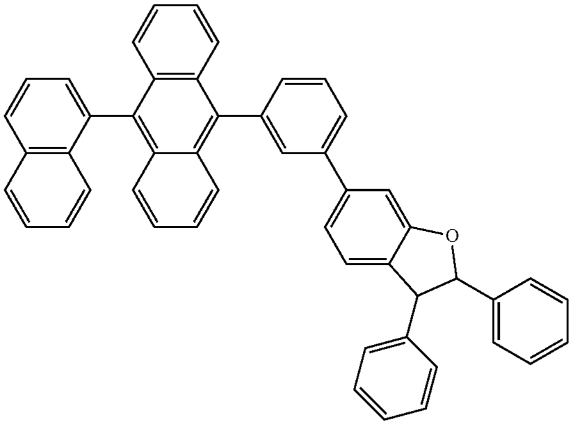

-continued
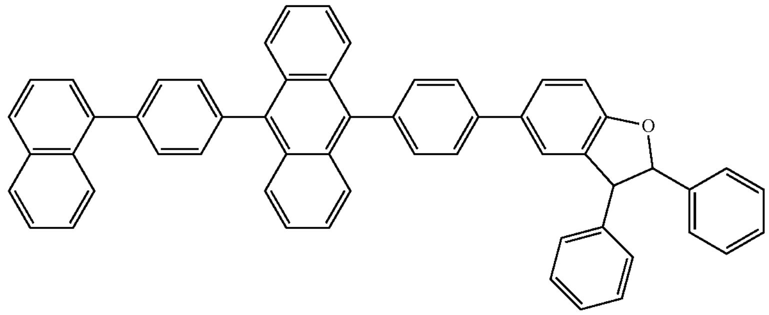
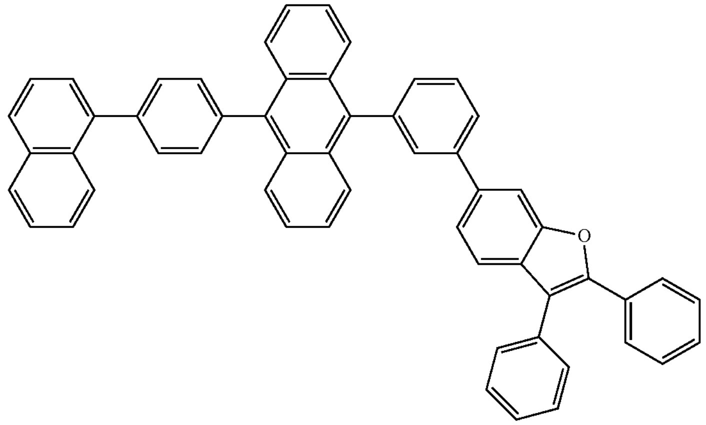
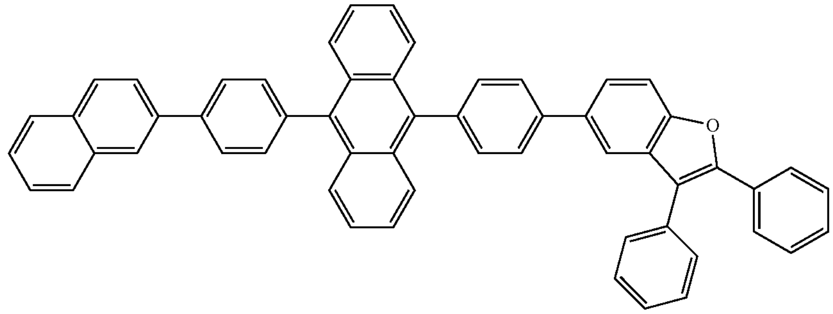
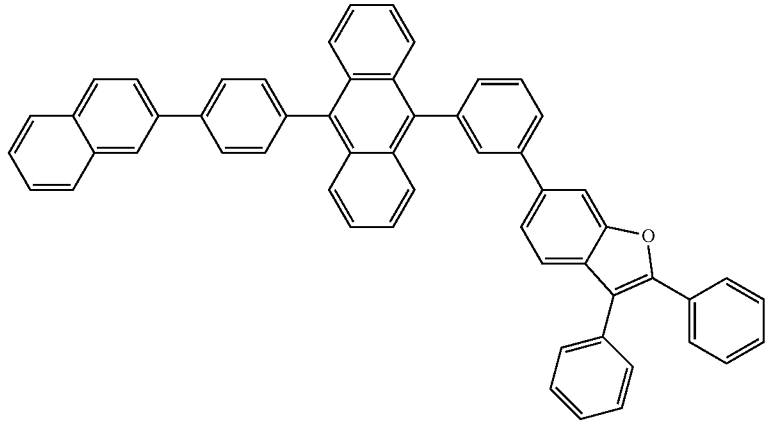

-continued
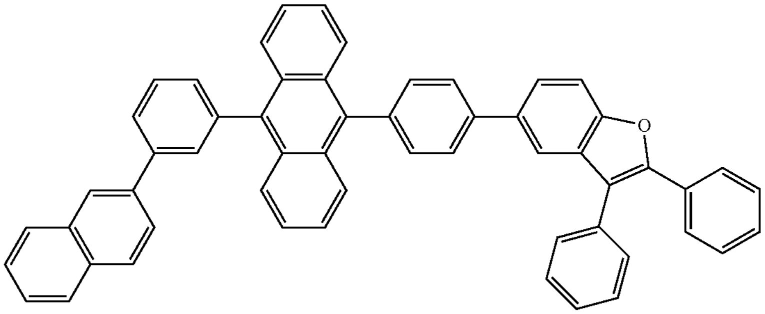
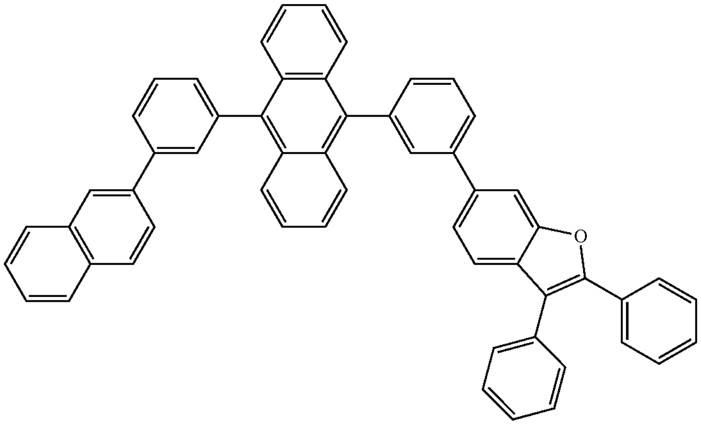
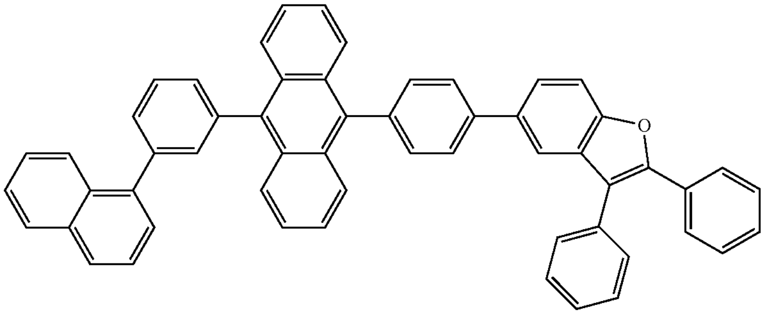
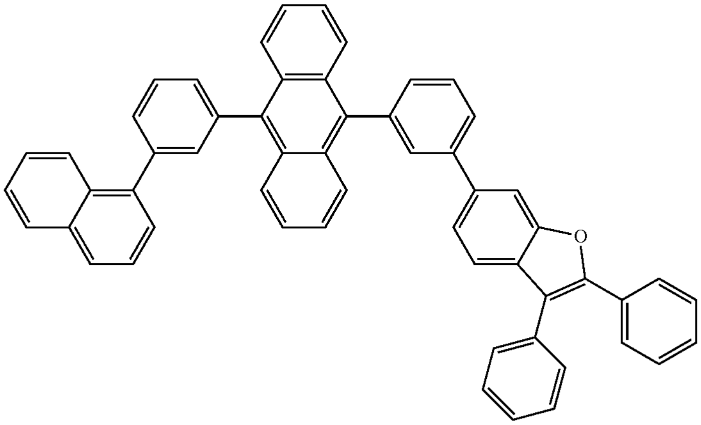
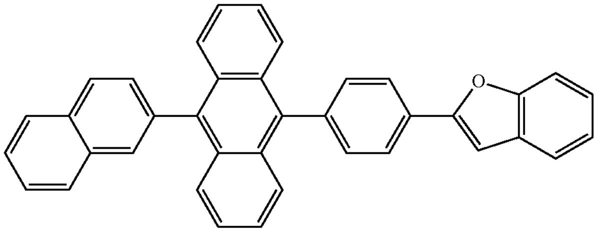

-continued
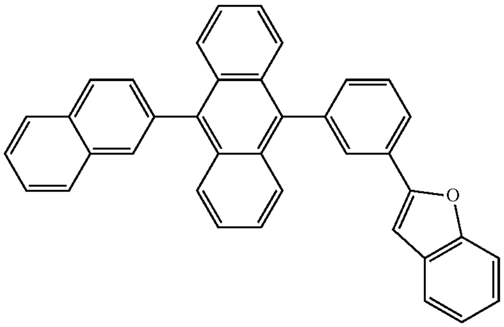
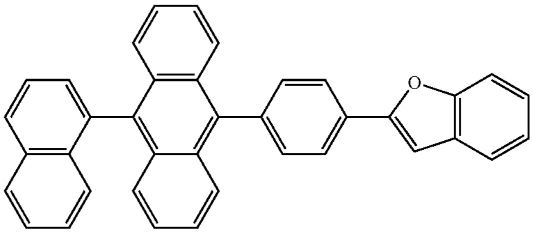
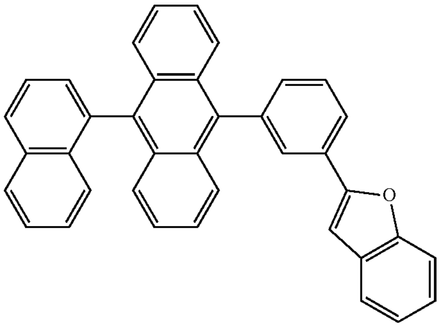
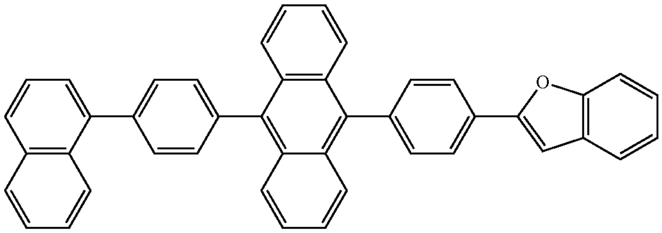
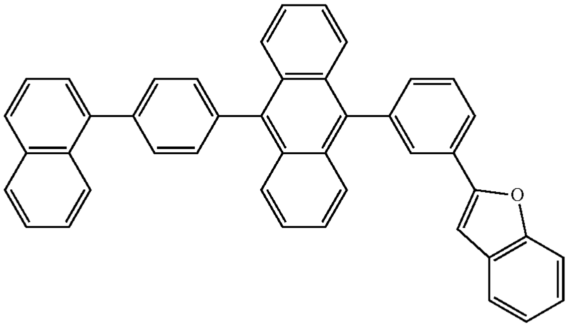
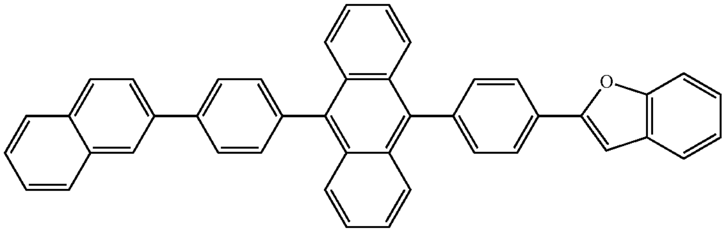
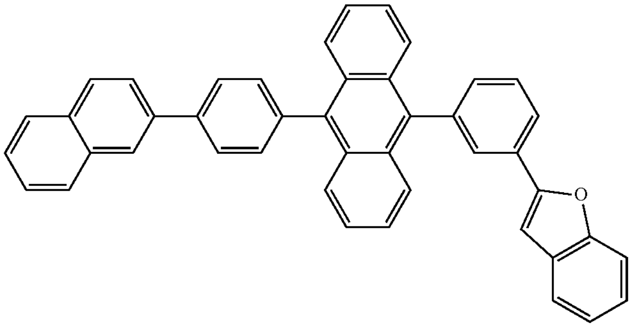

-continued
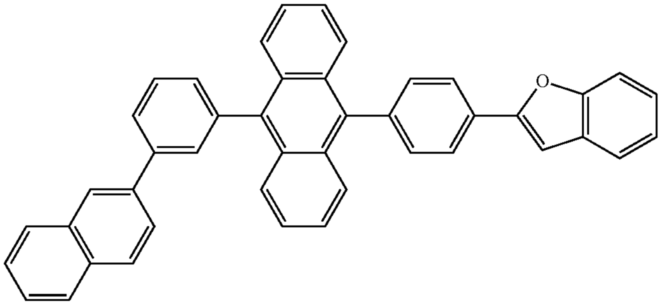
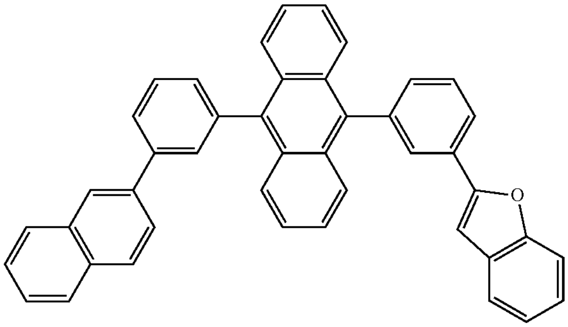
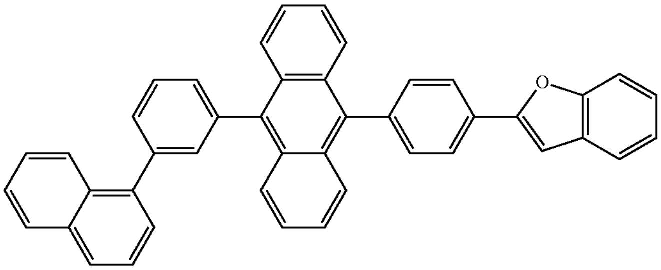
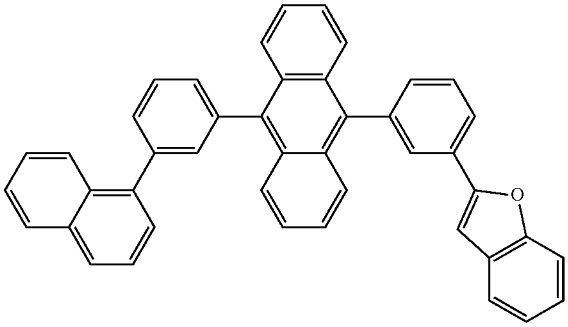
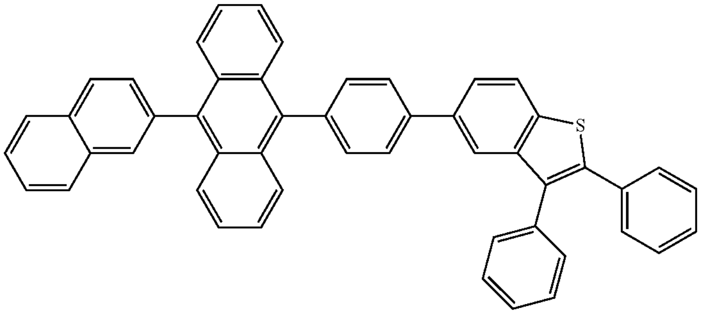

-continued
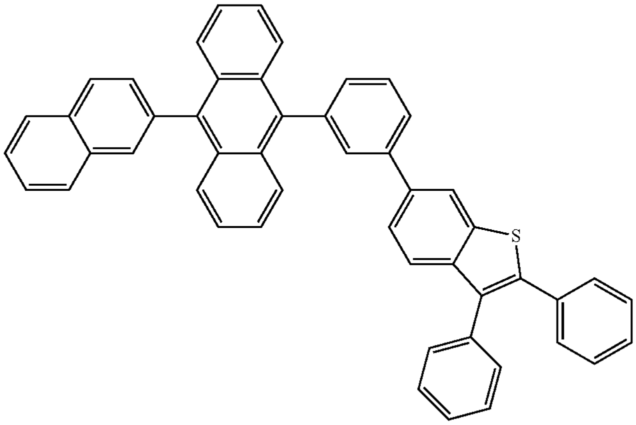
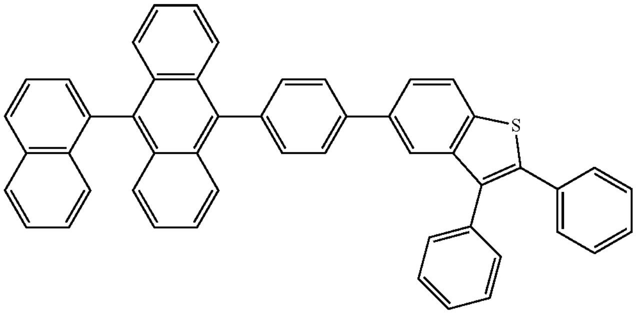
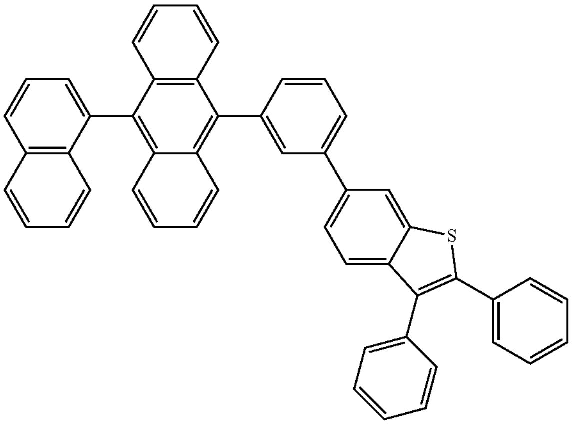
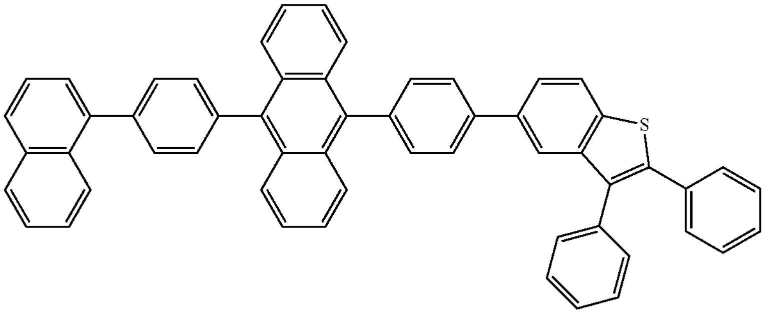

-continued
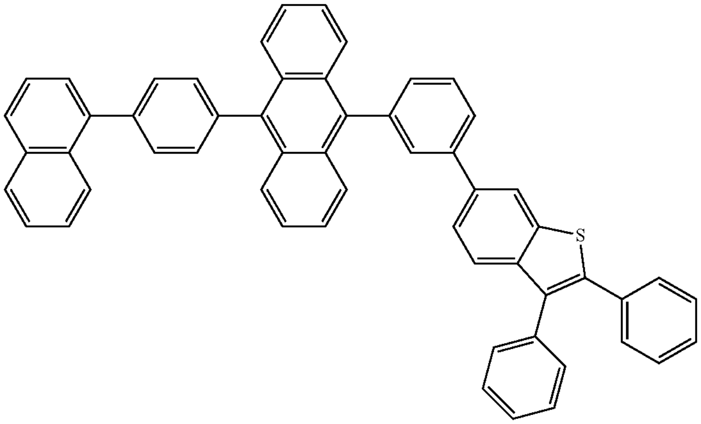
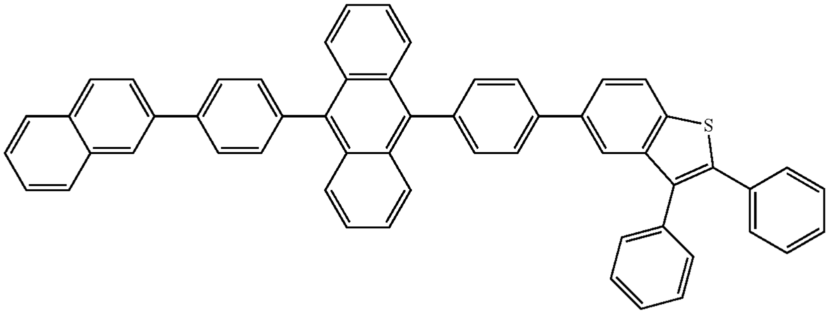
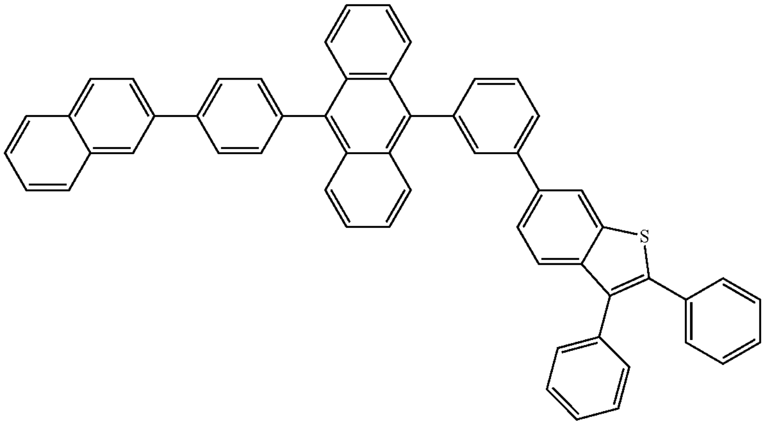
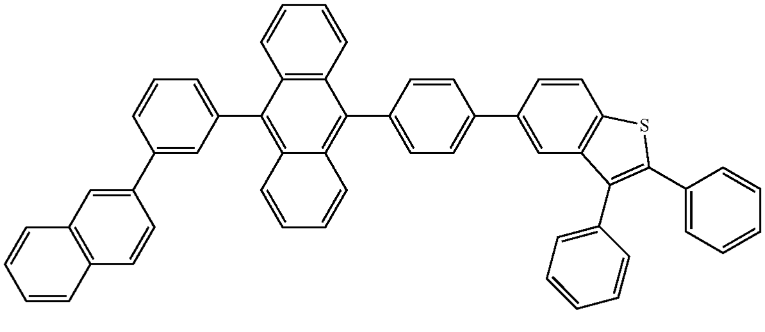

-continued
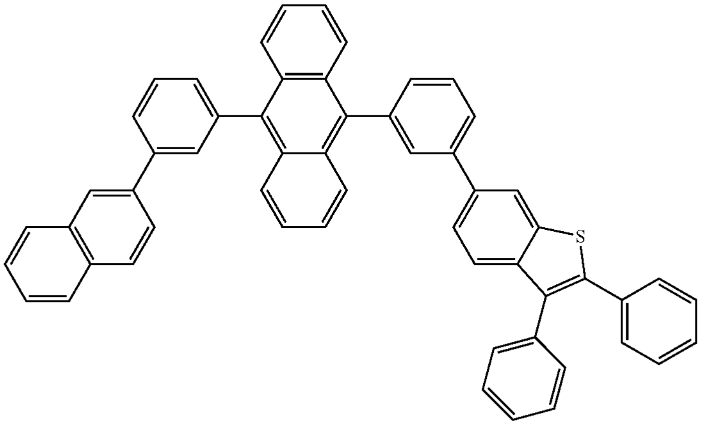
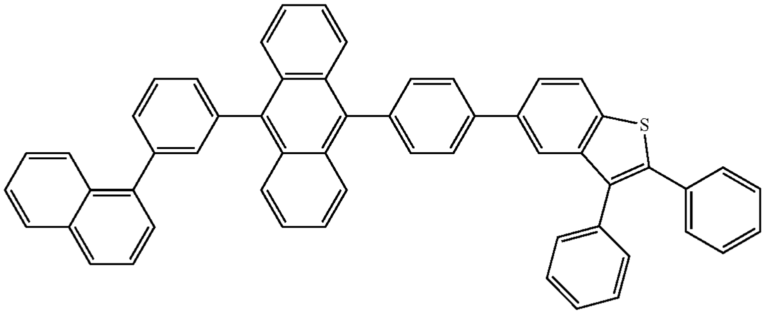
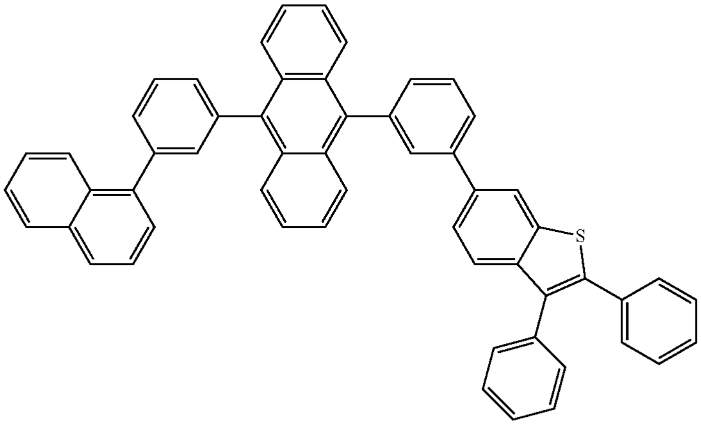
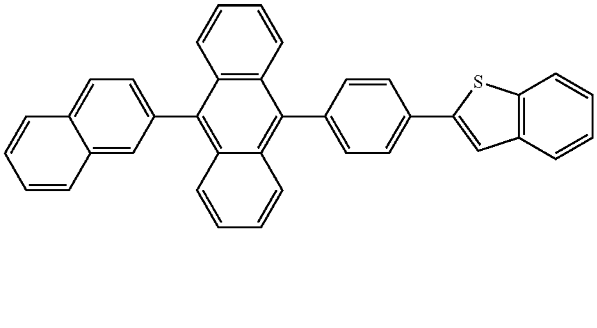
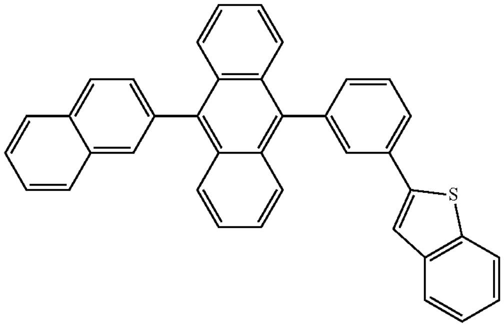

-continued
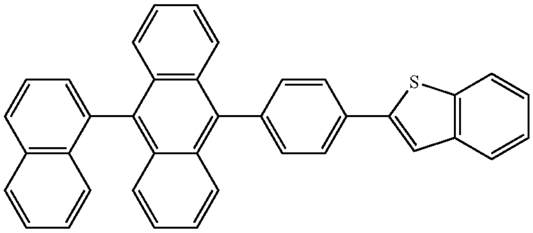
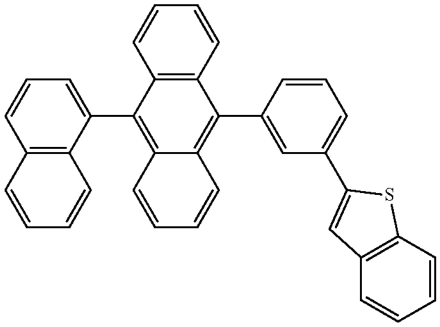
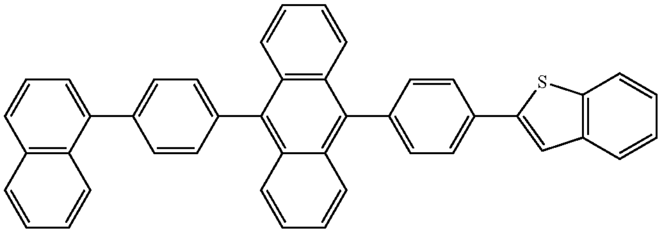
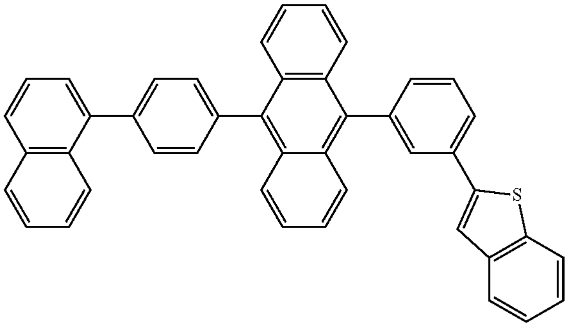
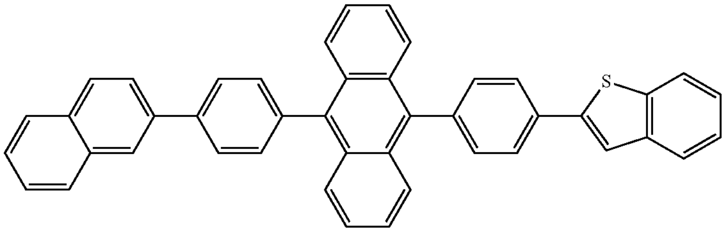
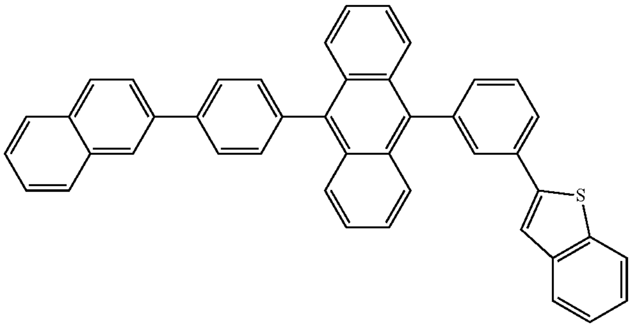

-continued
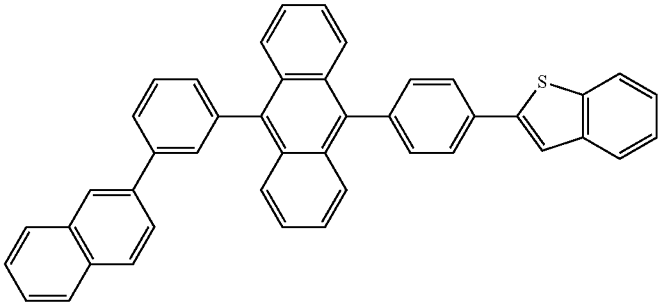
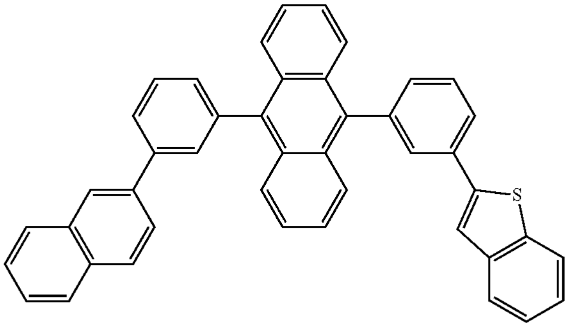
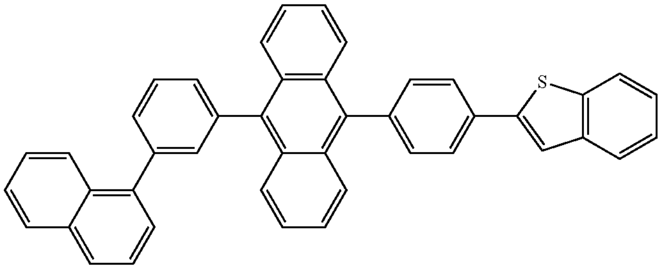
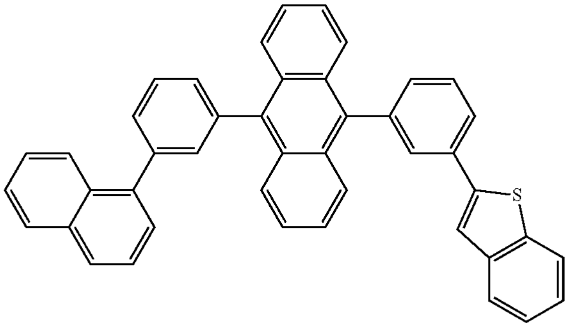
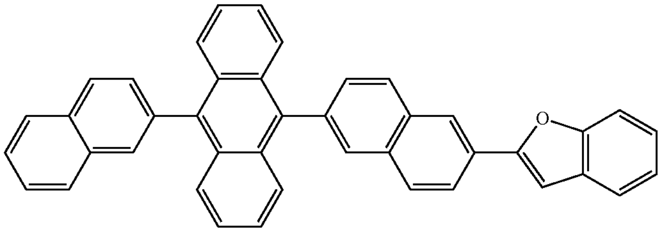
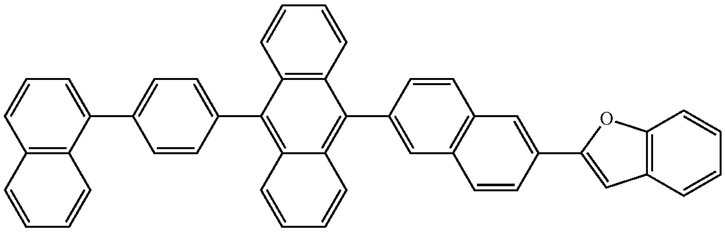

-continued
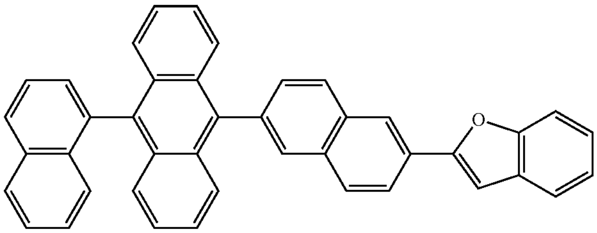
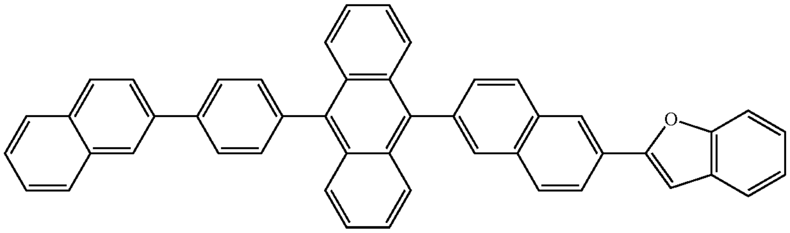
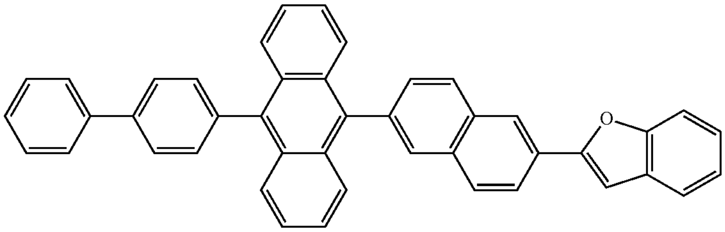
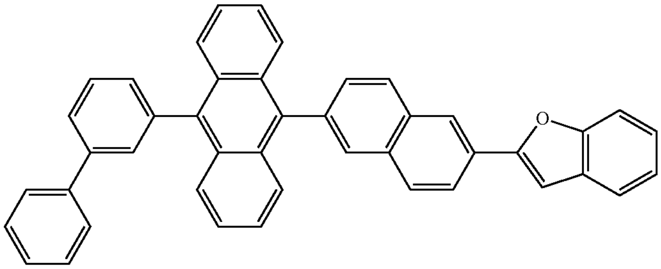
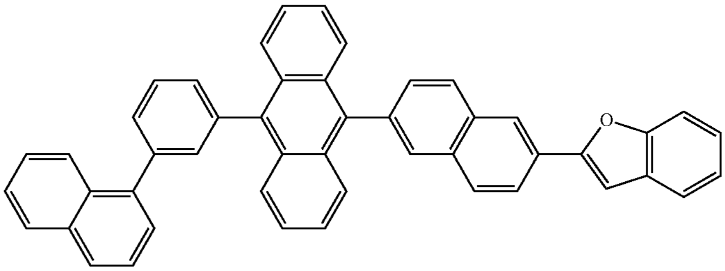
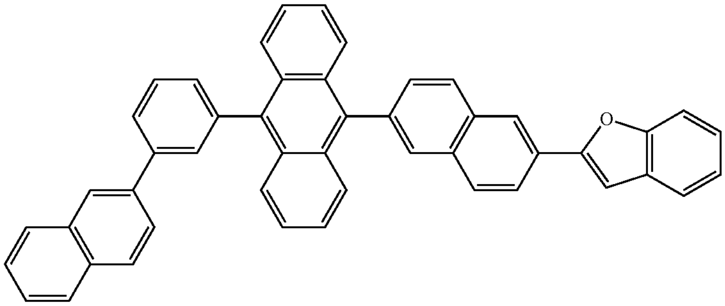

-continued
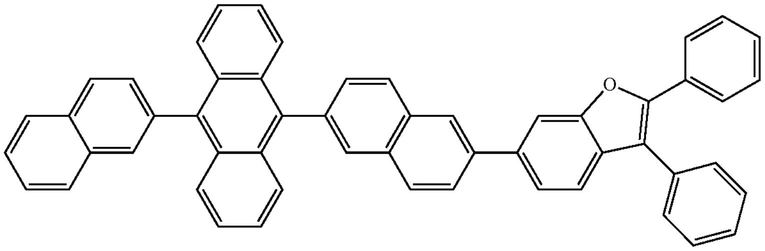
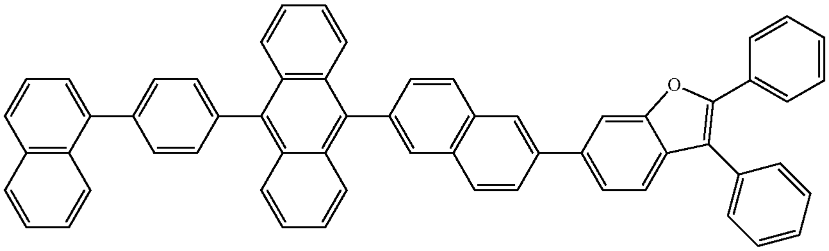
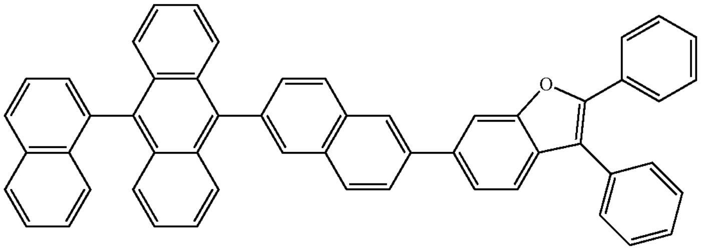
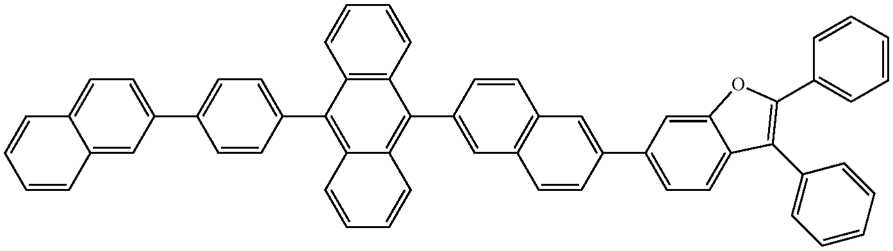
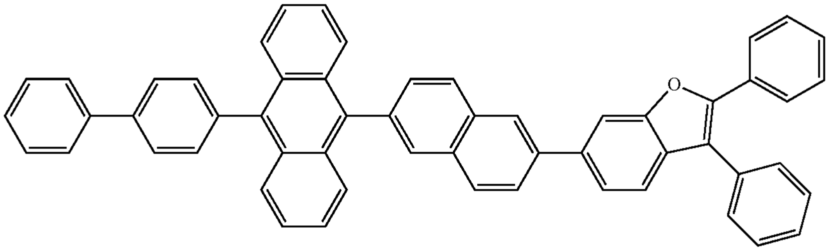
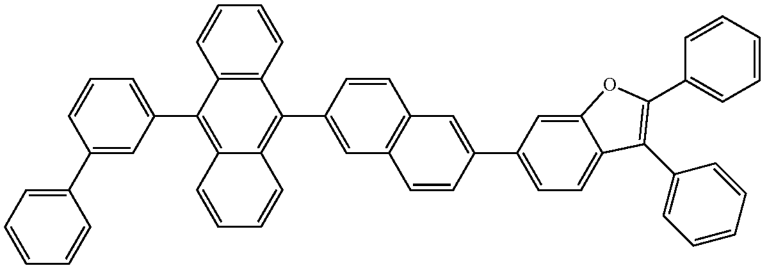

-continued
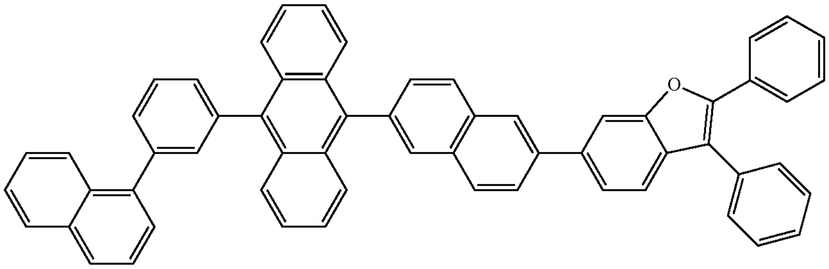
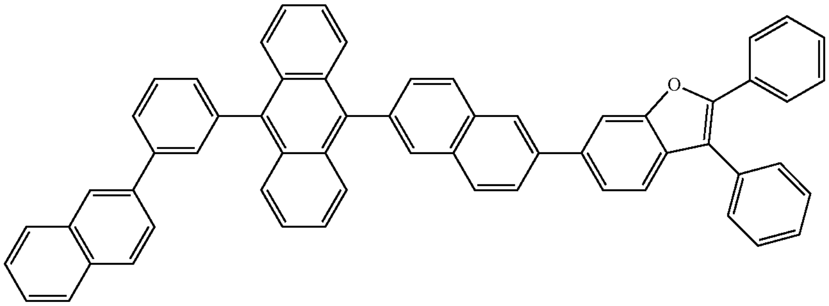
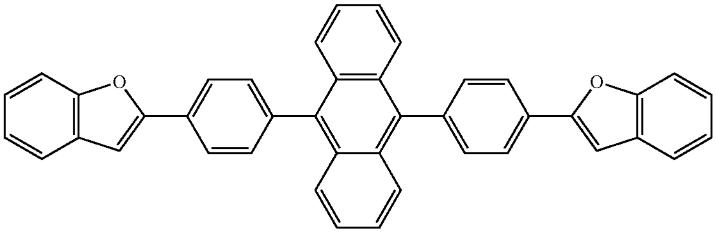
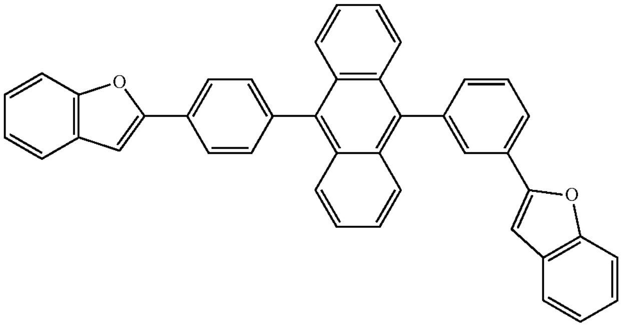
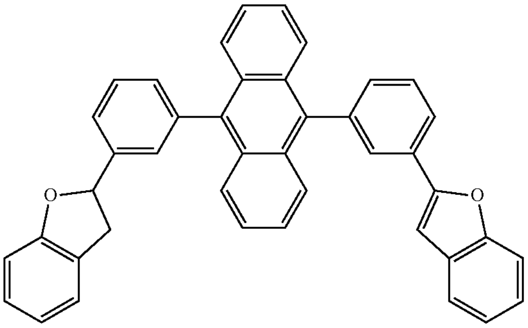
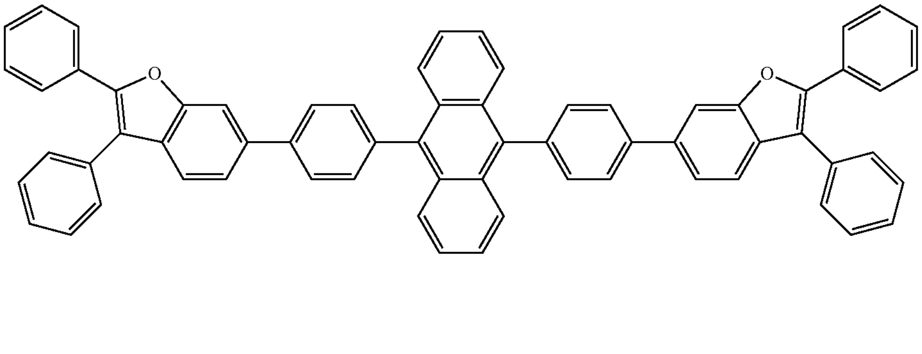

-continued
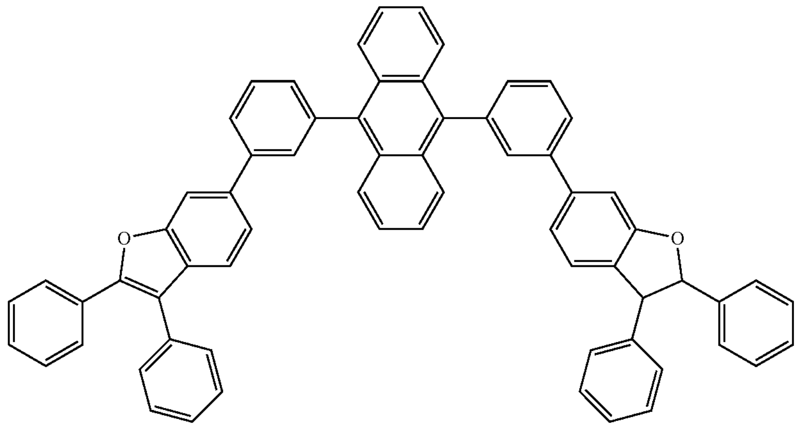
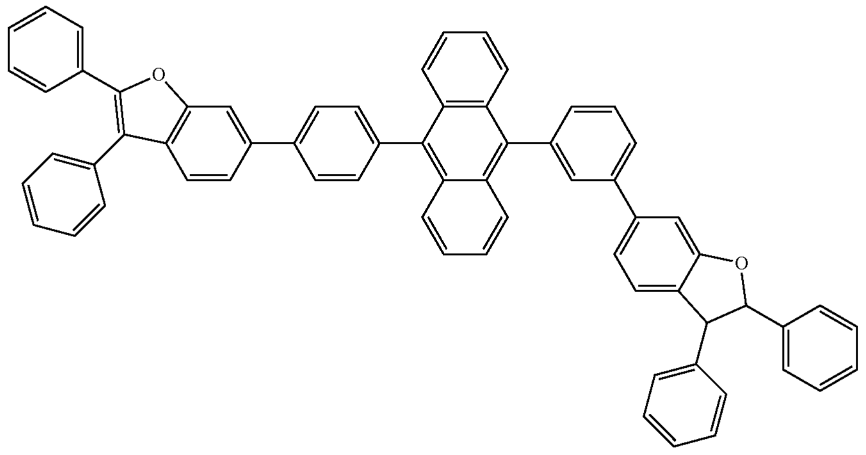
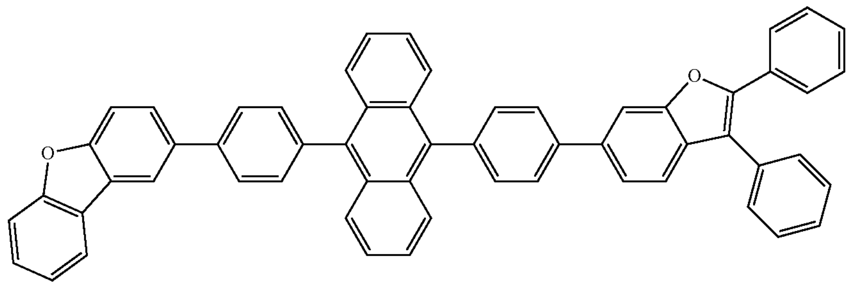
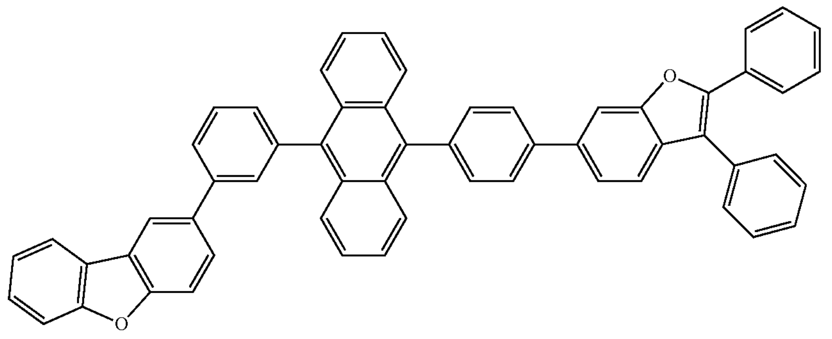

-continued
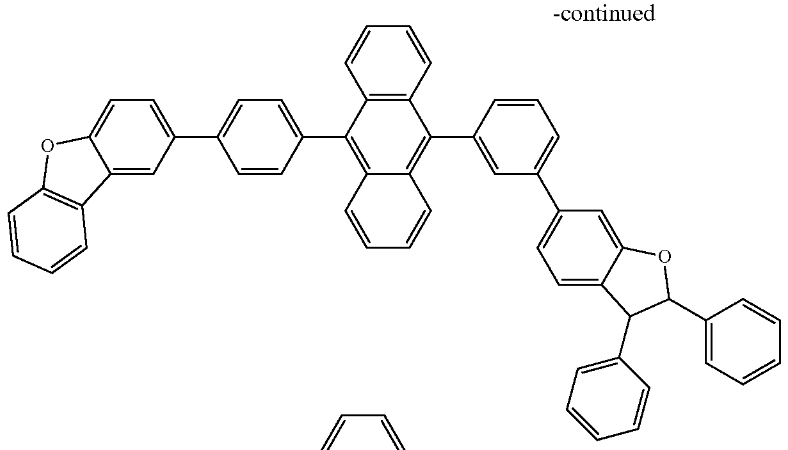
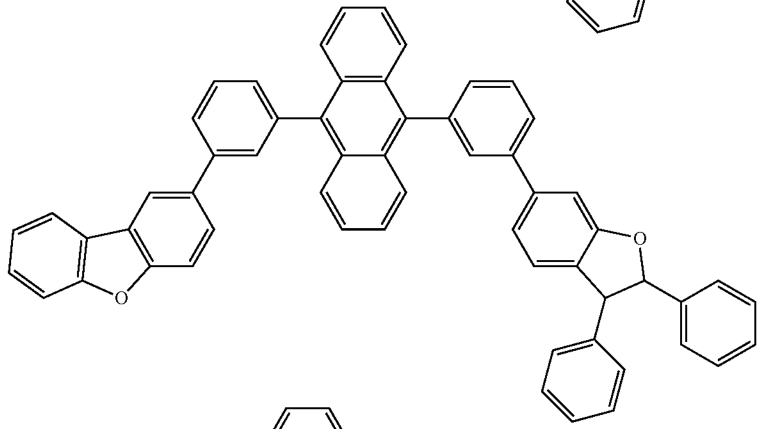
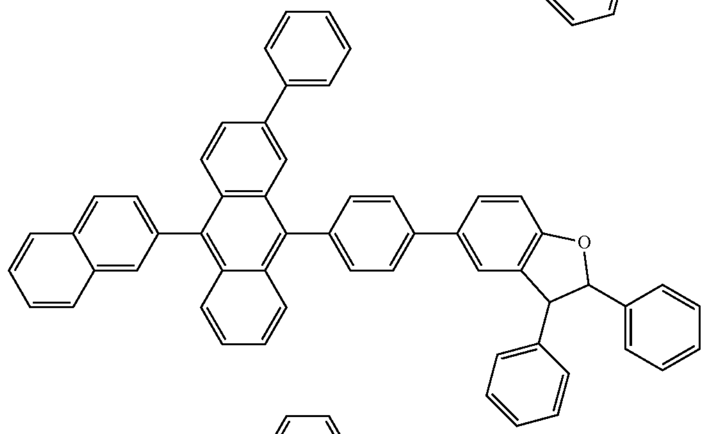
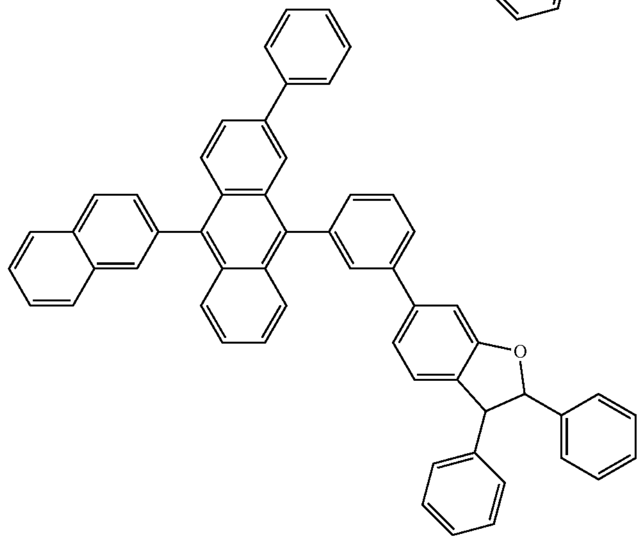

-continued
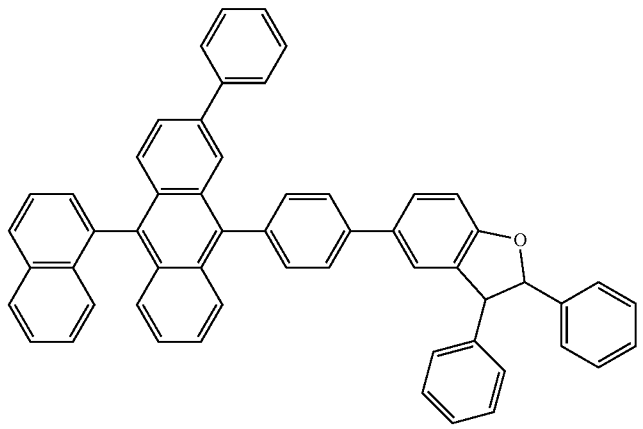
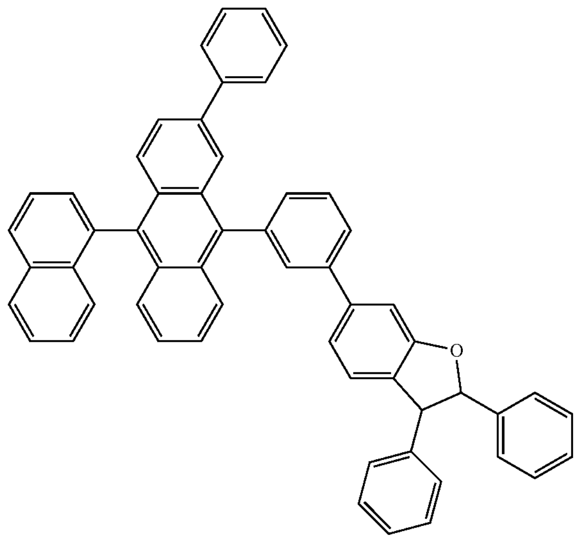
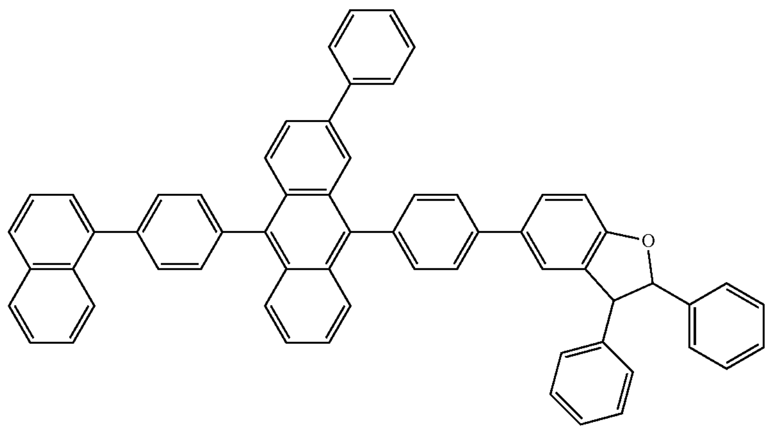

-continued
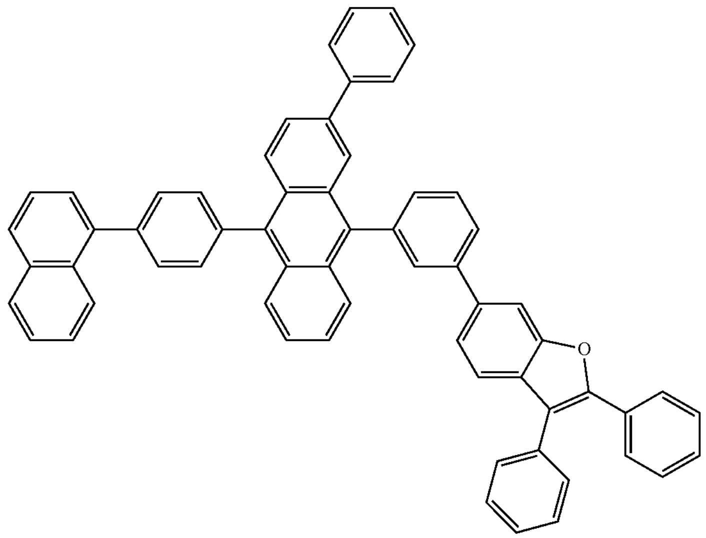
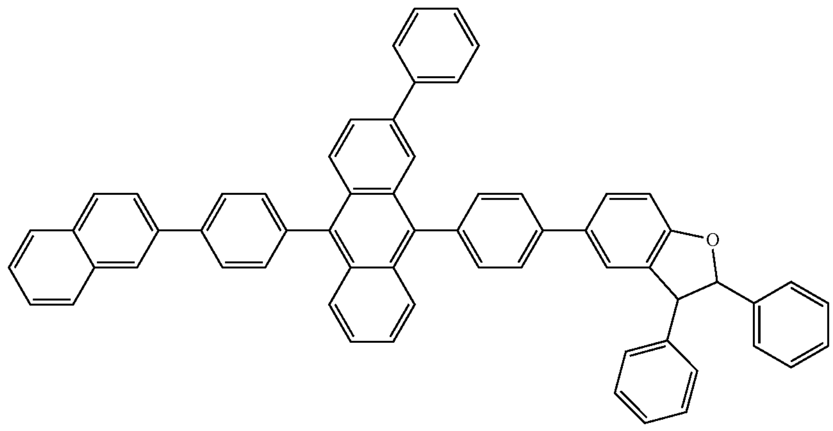
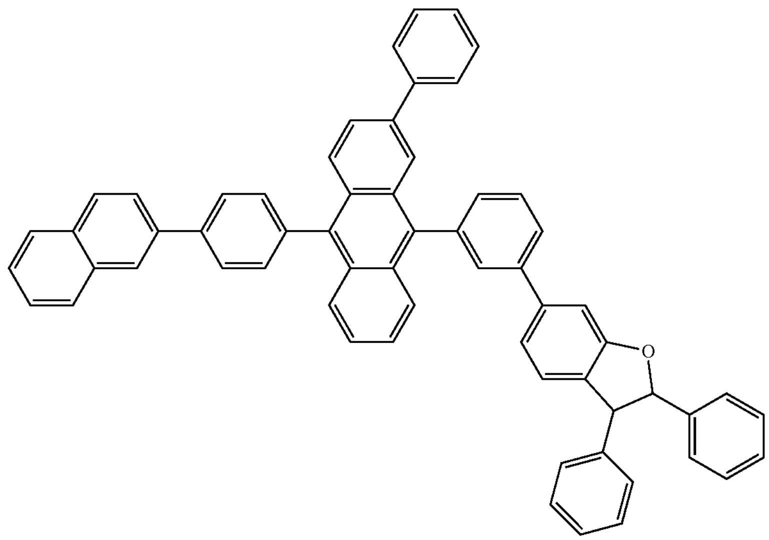

-continued
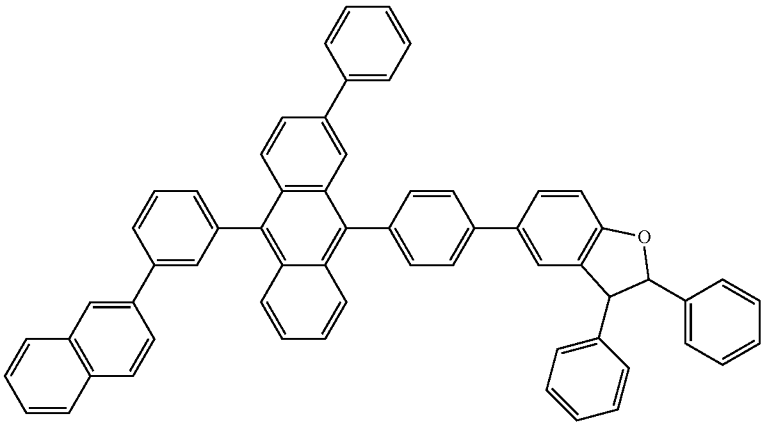
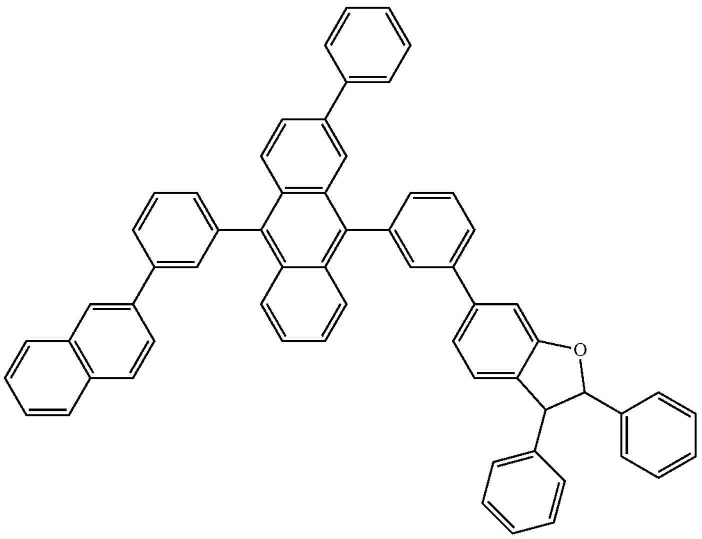
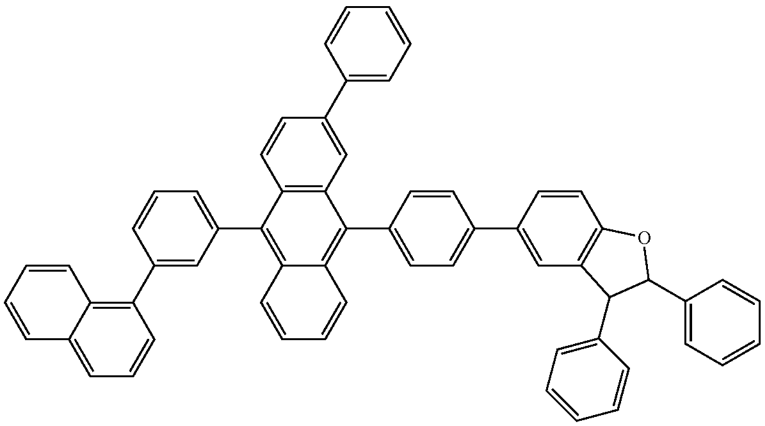

-continued
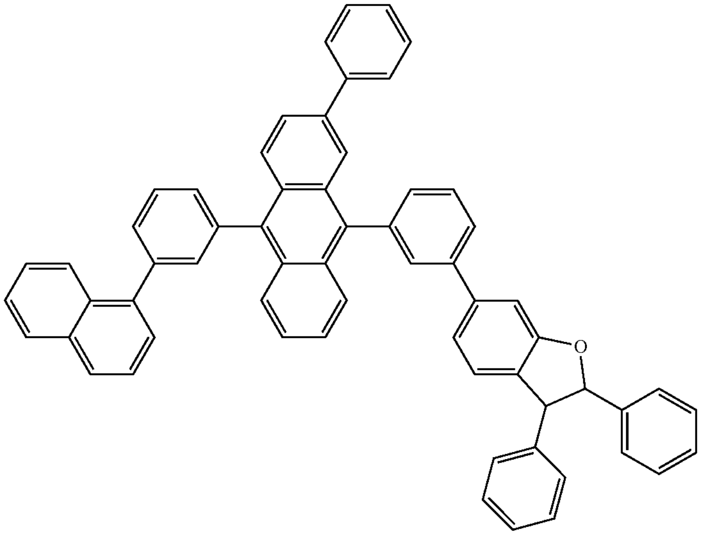
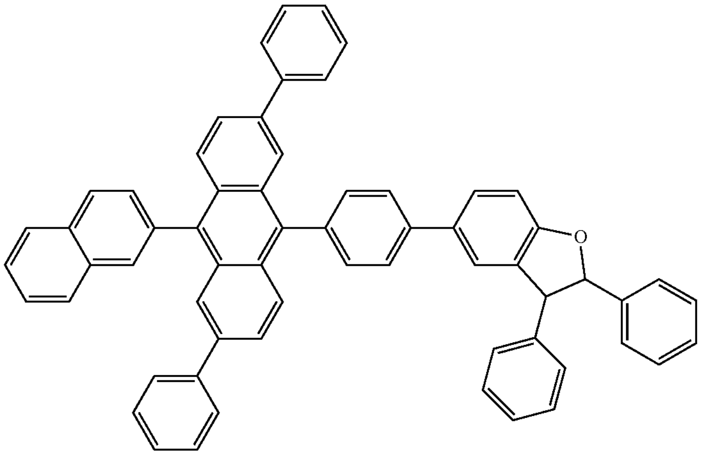
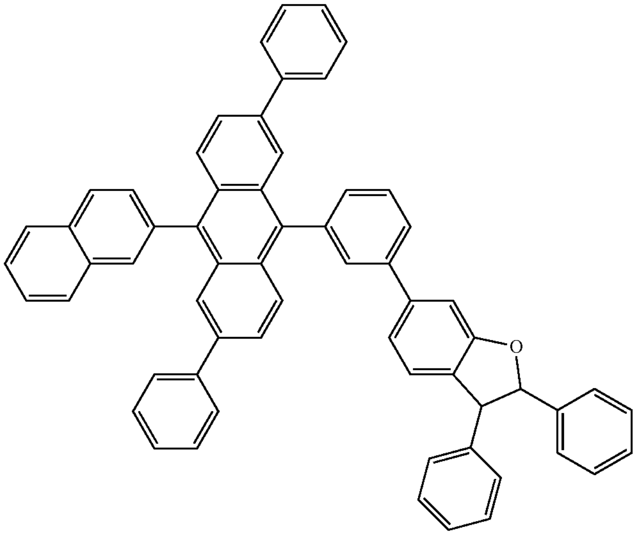

-continued
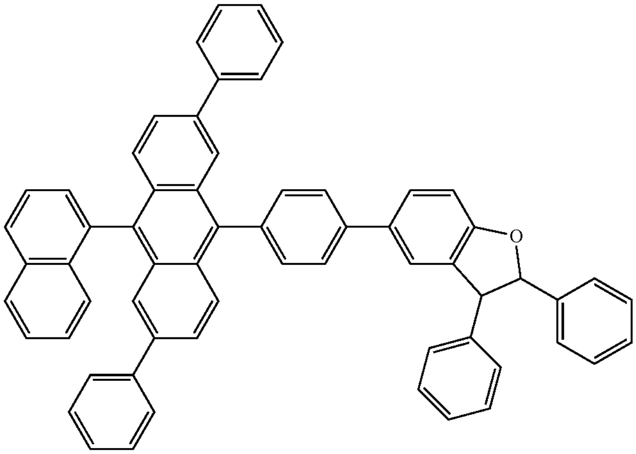
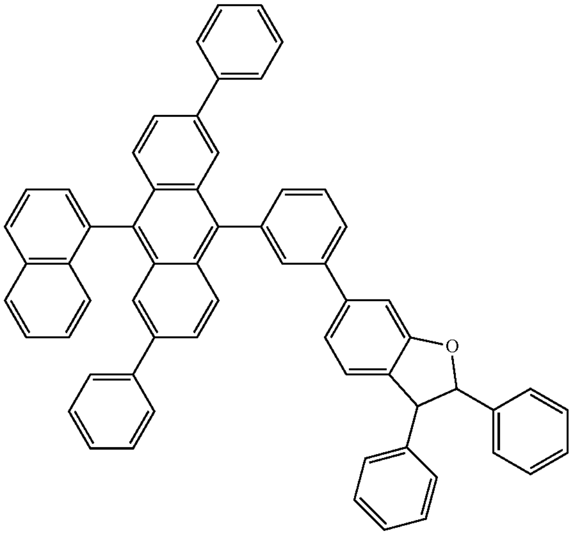
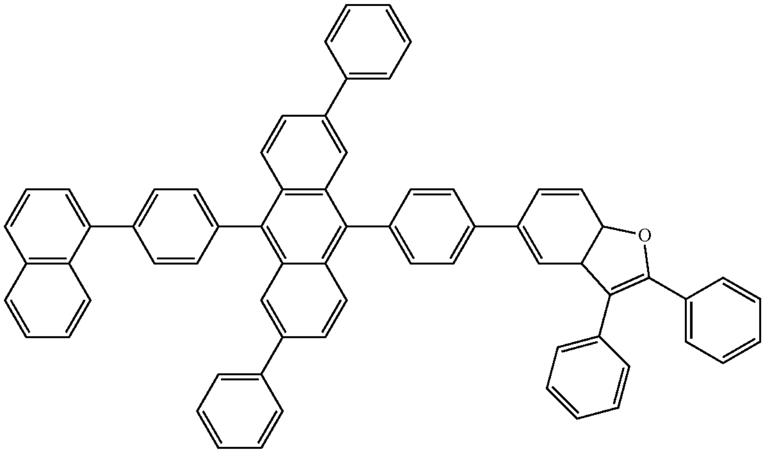

-continued
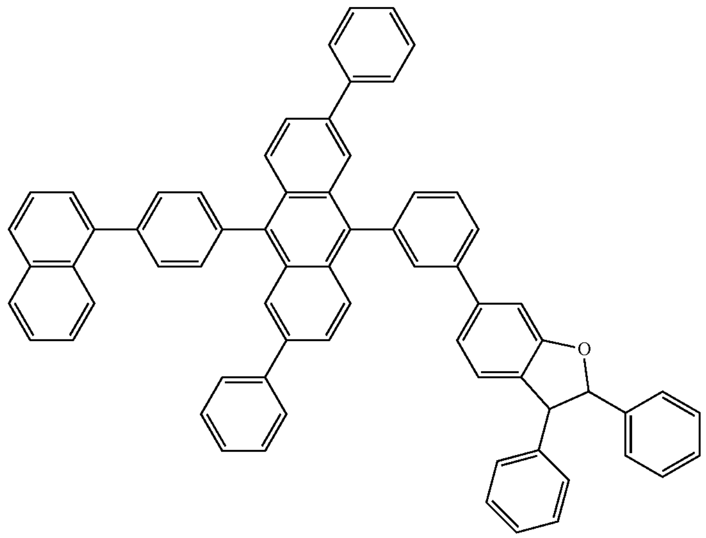
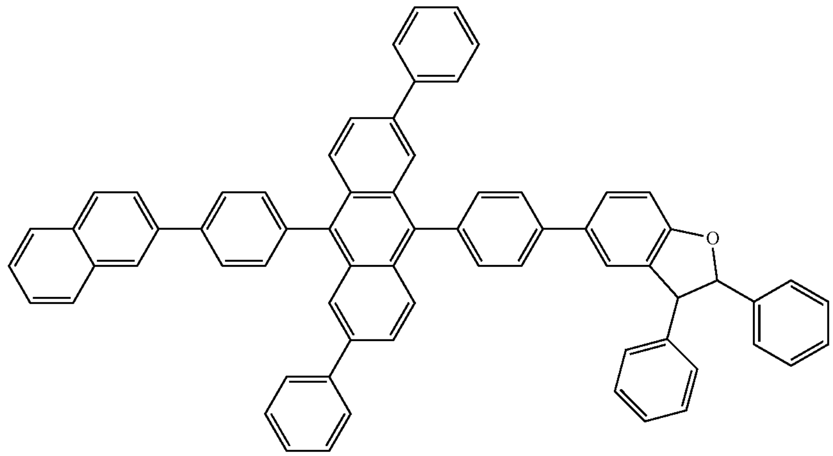
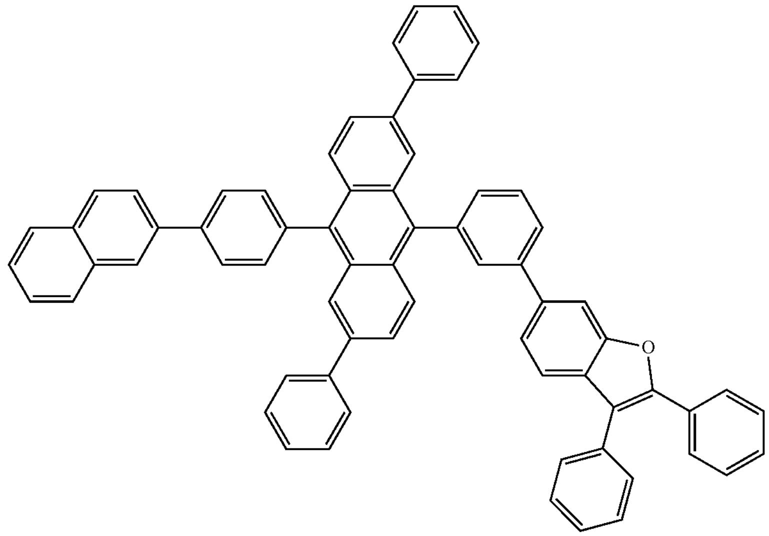

-continued
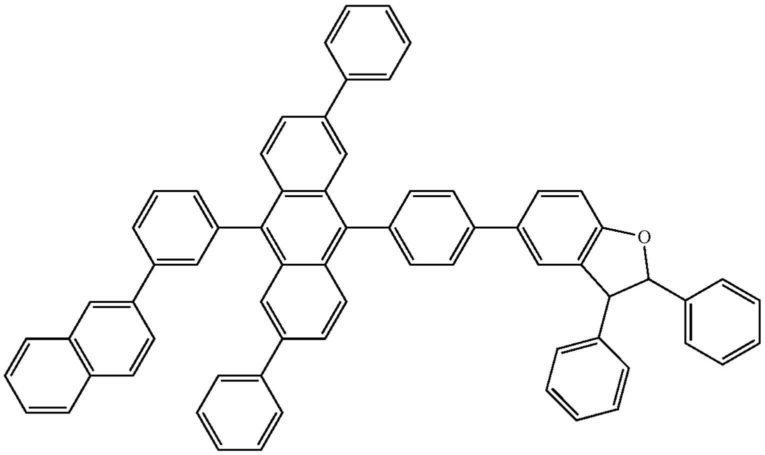
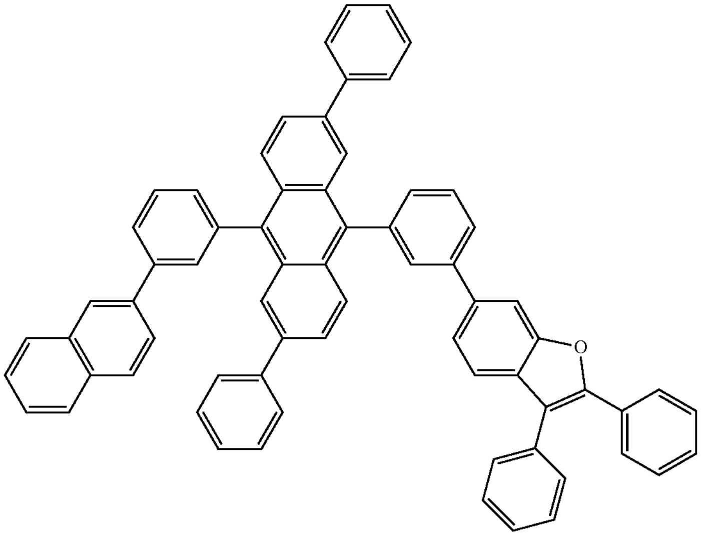
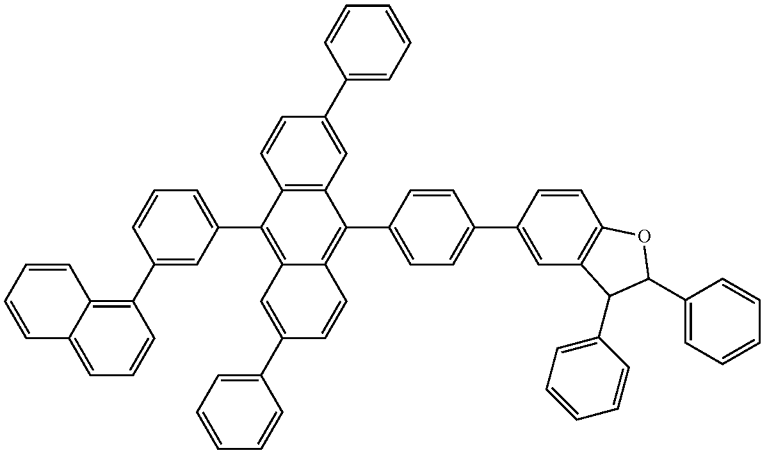

-continued
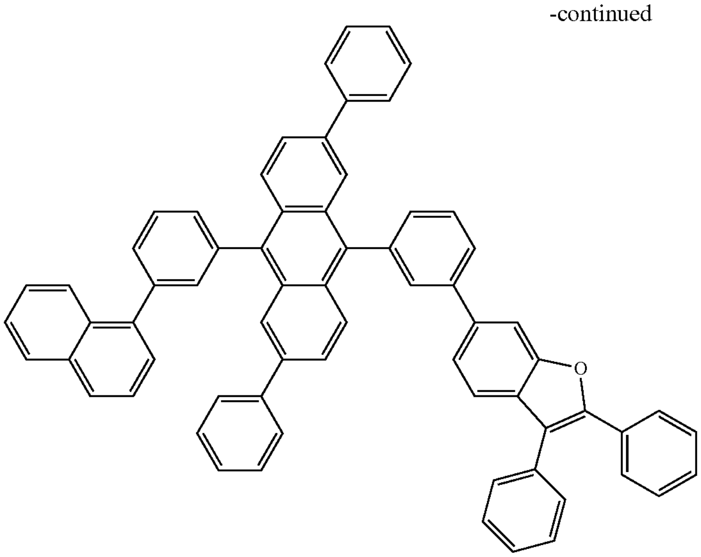
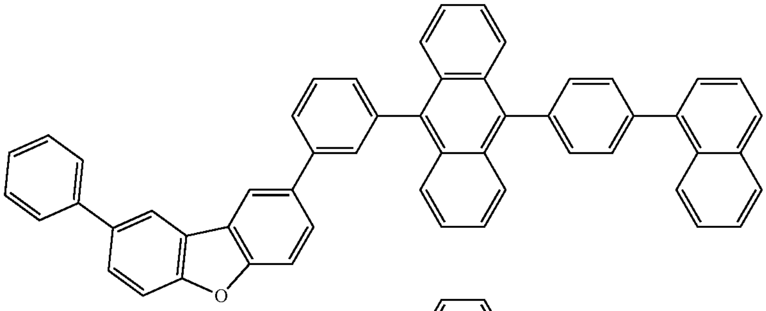
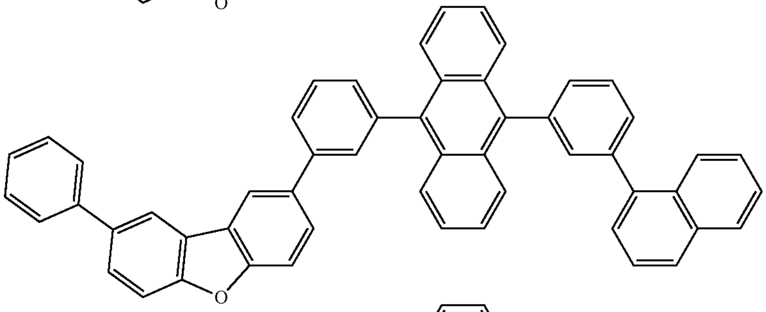
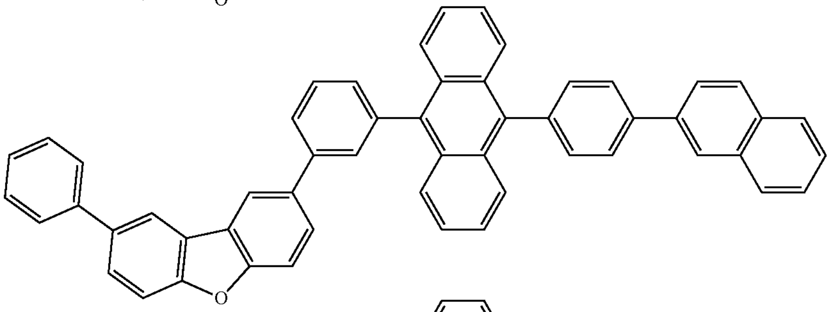
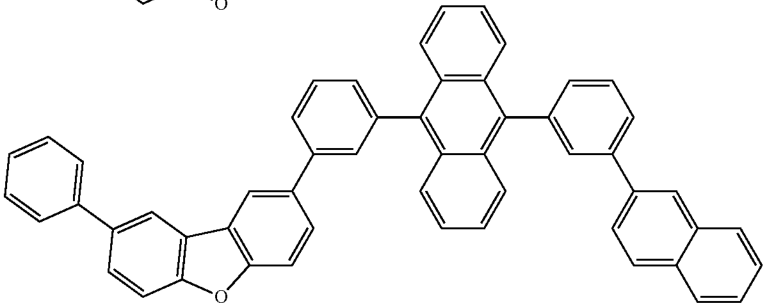

-continued
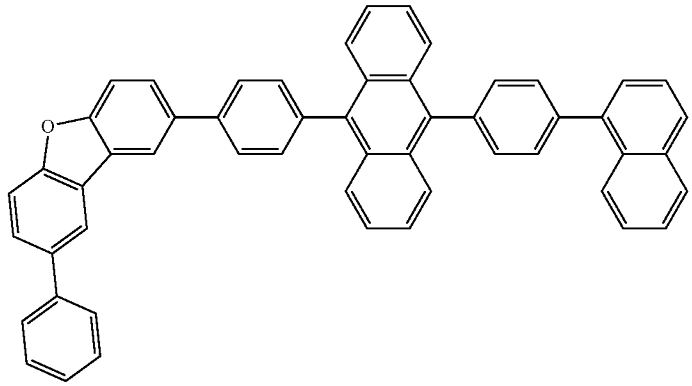
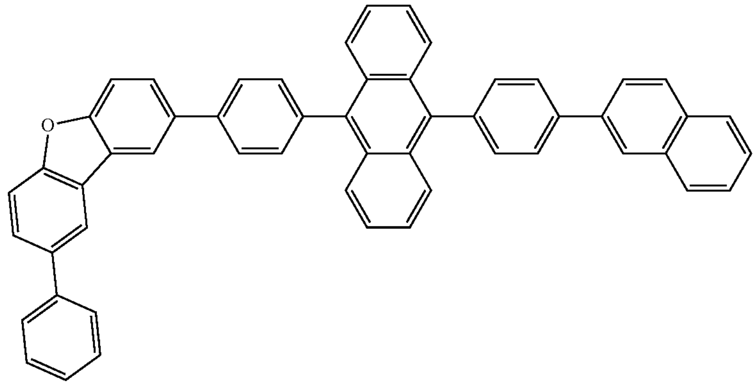
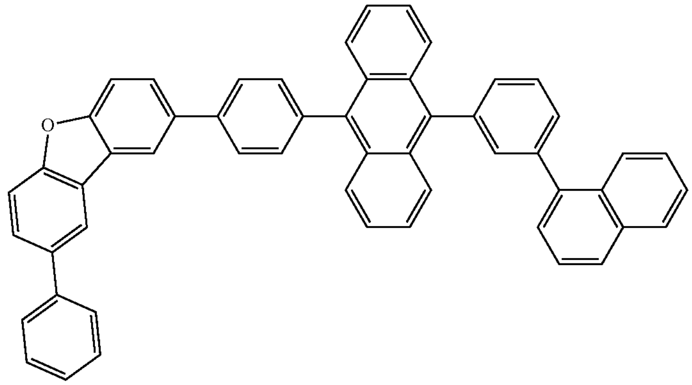
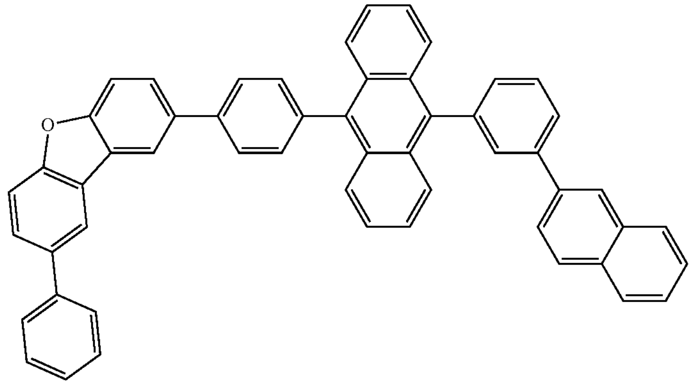

-continued
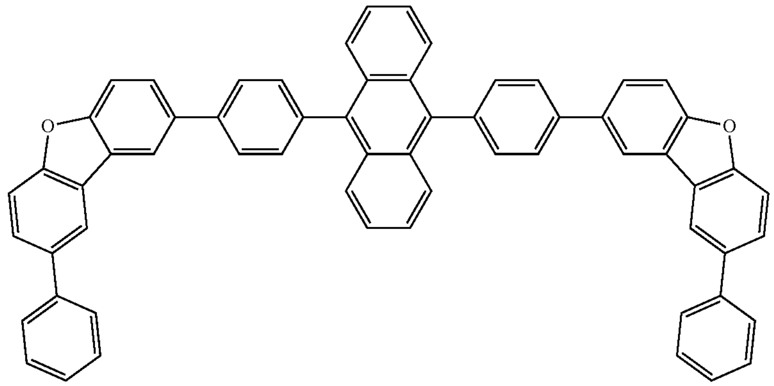
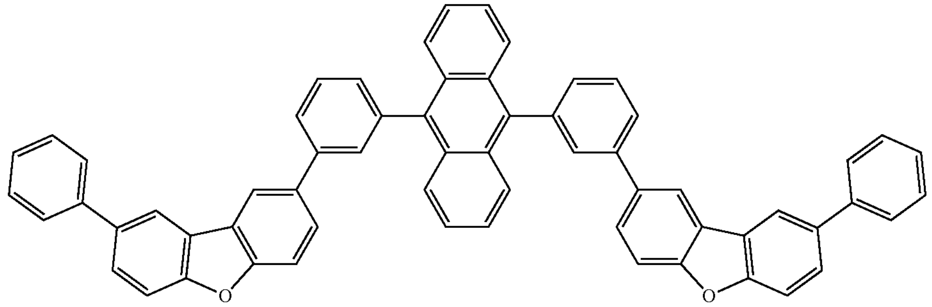
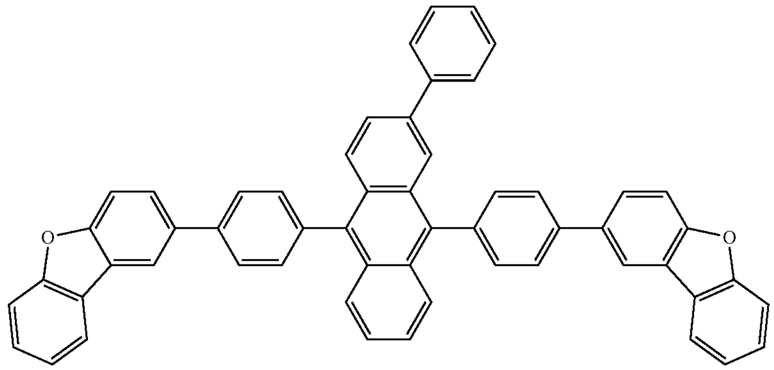
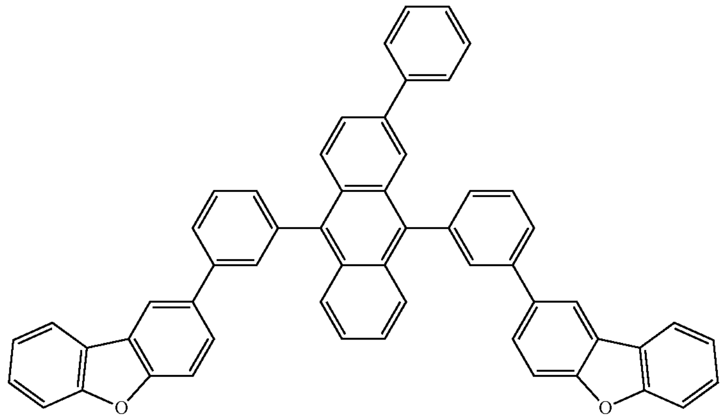

-continued
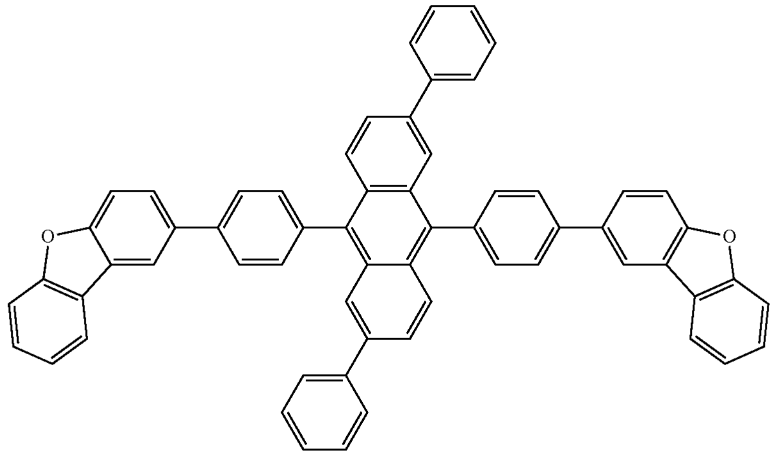
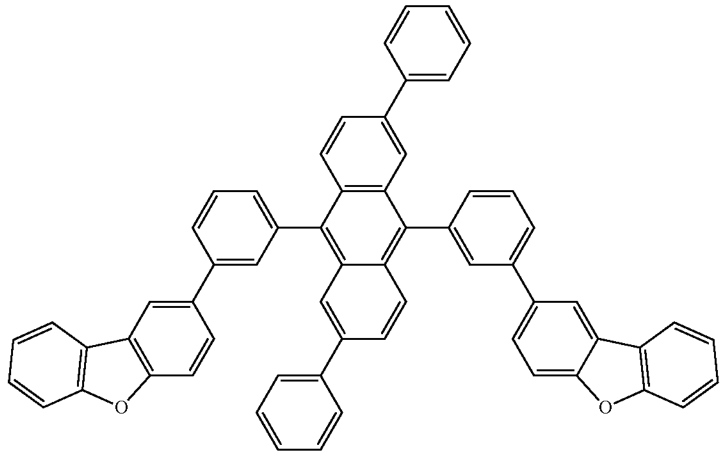
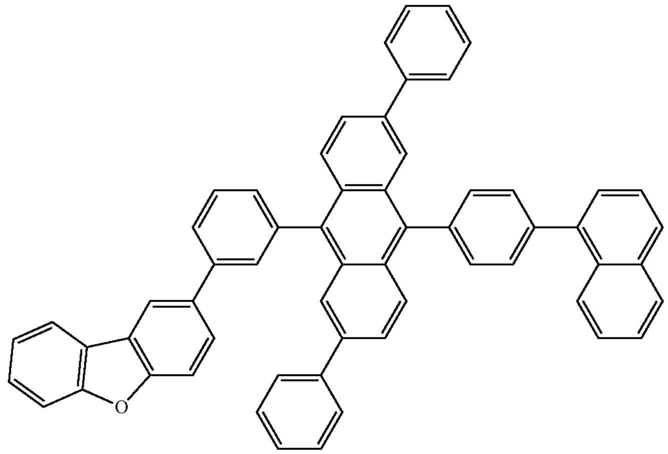

-continued
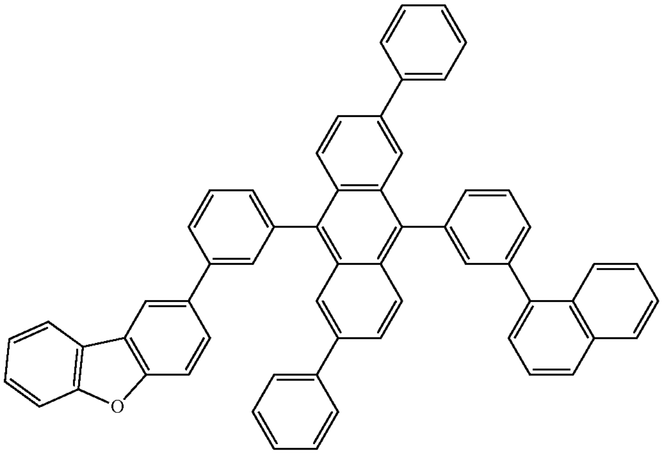
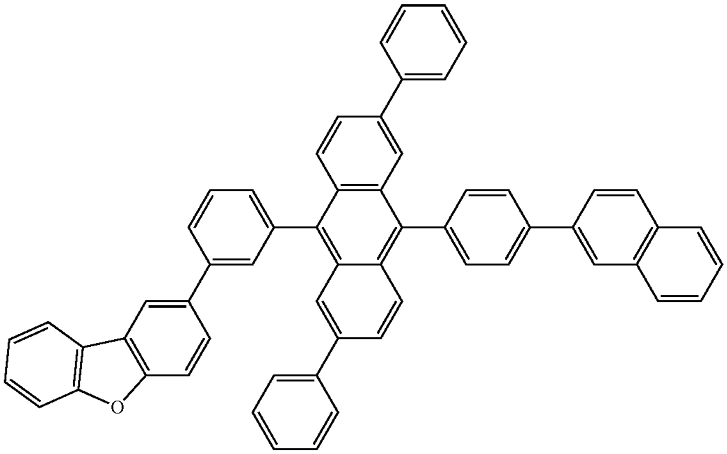
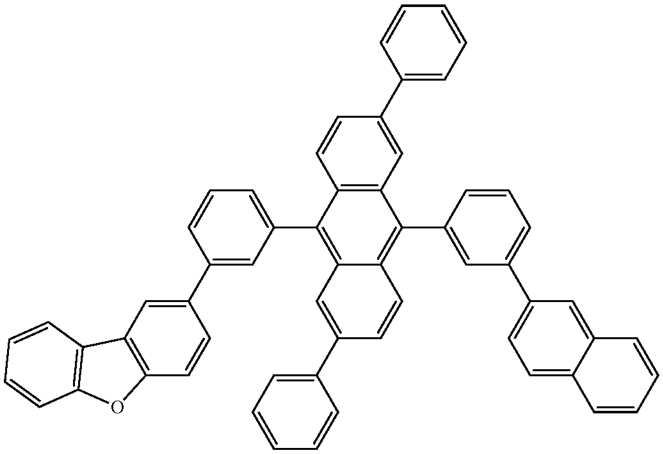

-continued
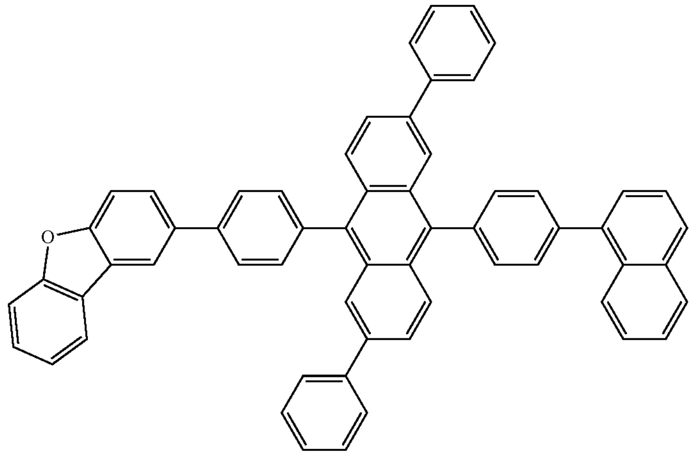
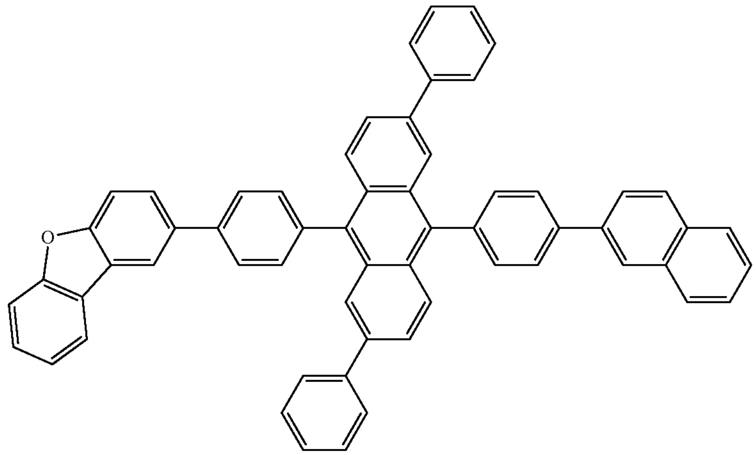
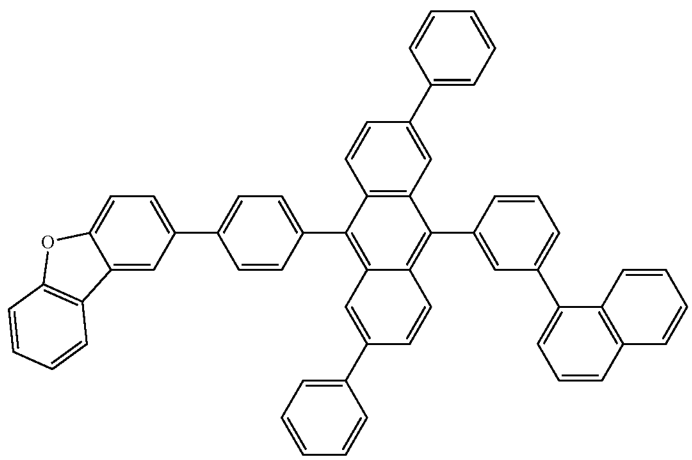

-continued
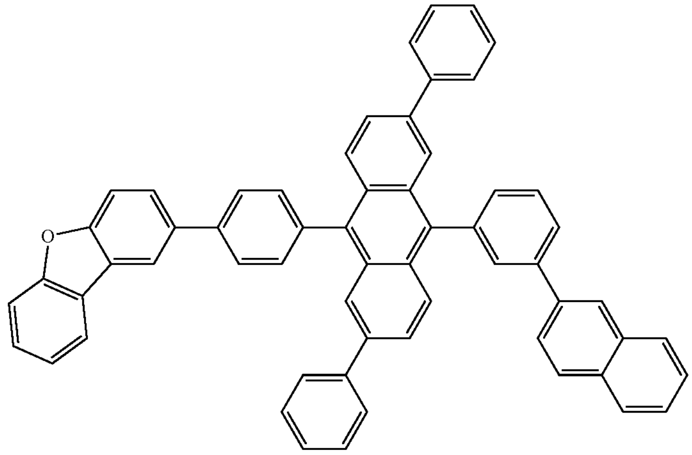
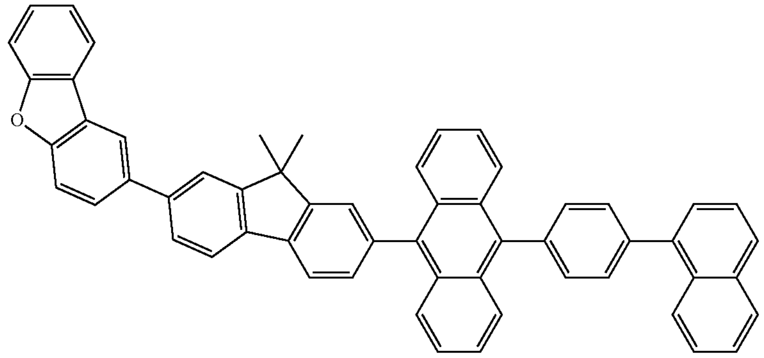
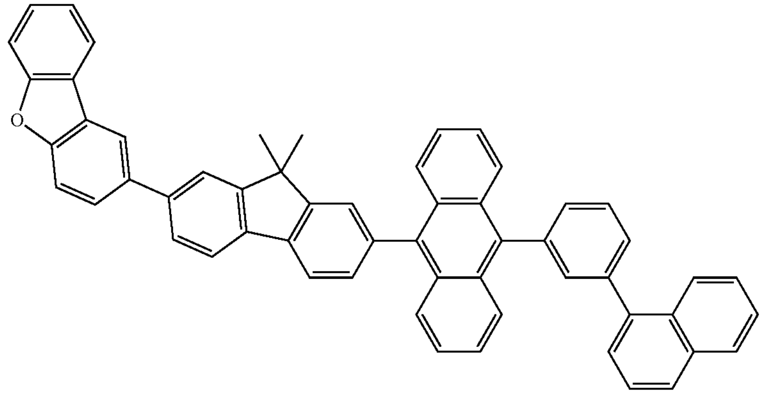
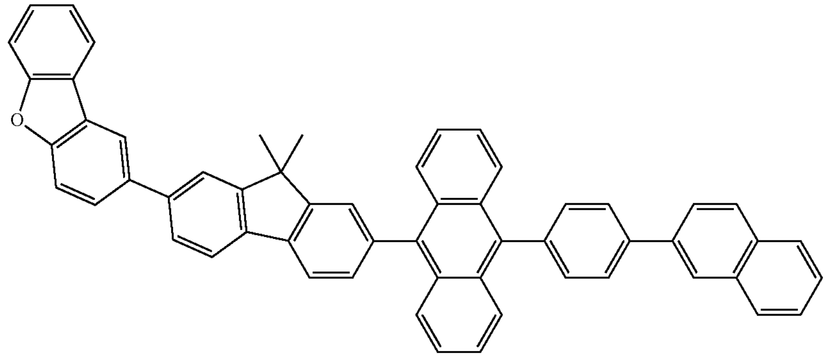

-continued
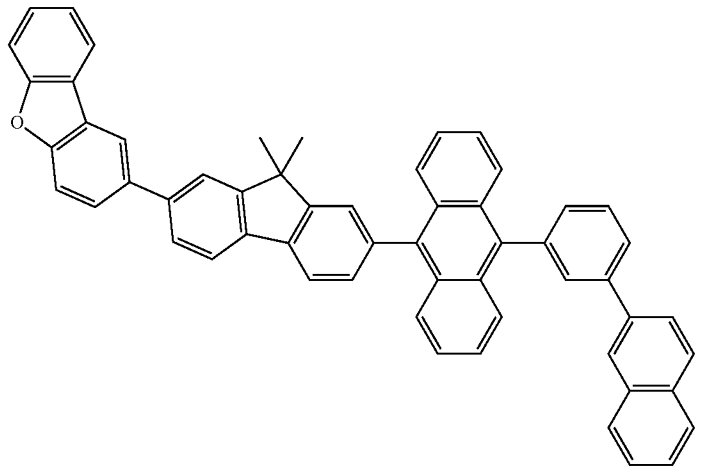
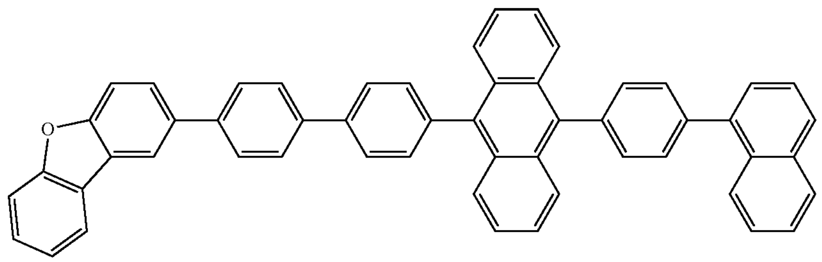
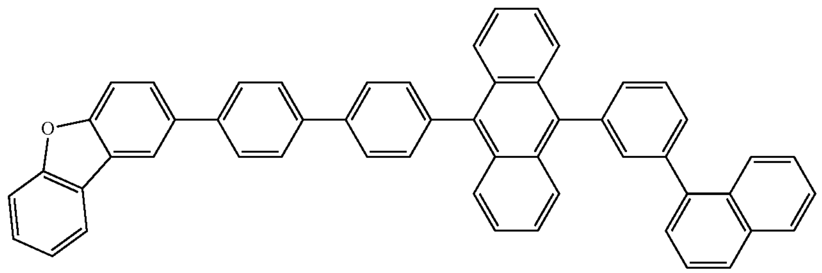
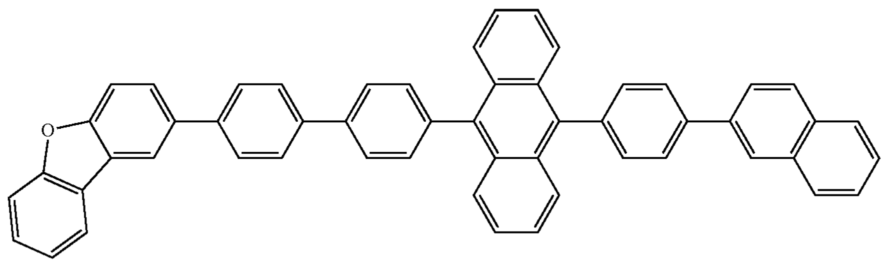
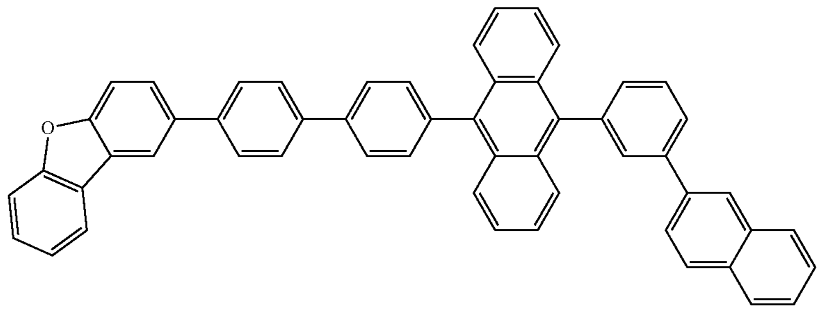

-continued
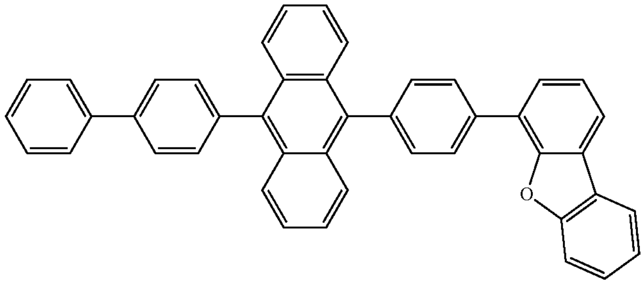
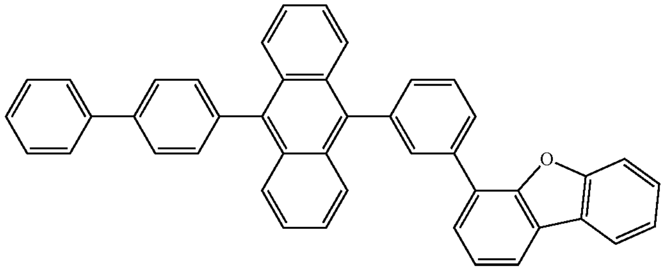
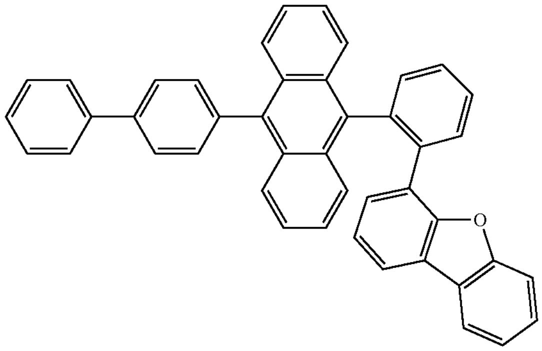
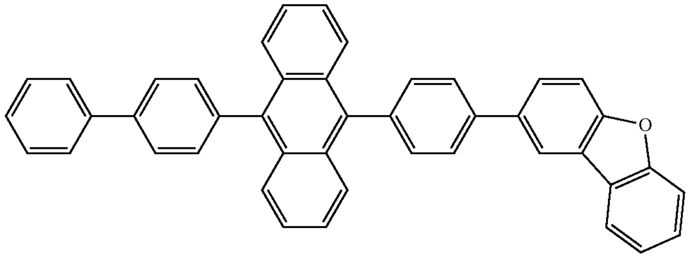
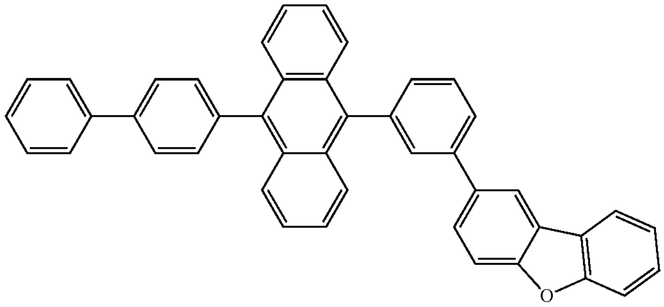

-continued
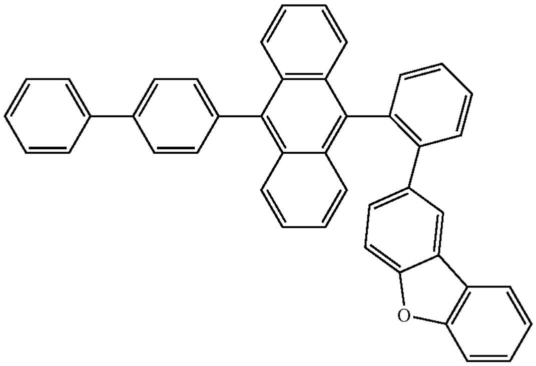
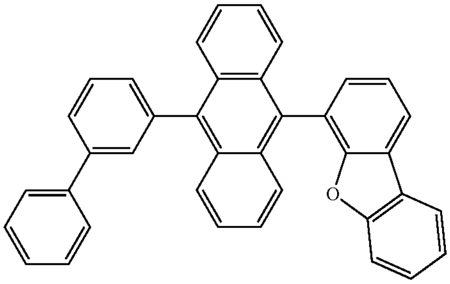
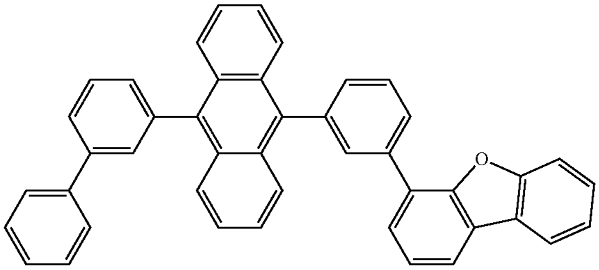
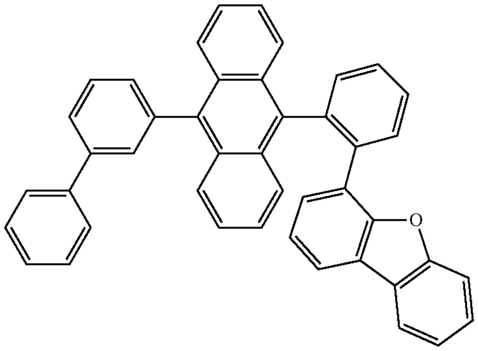
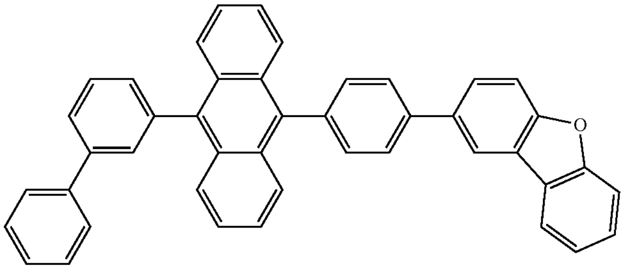
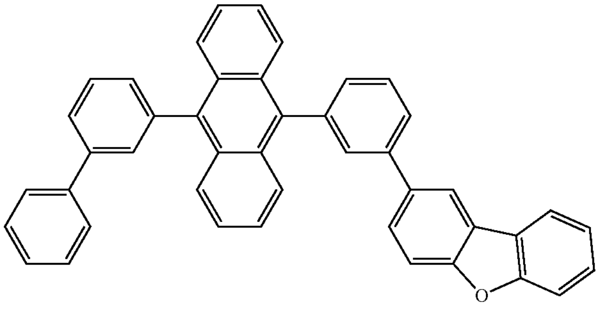
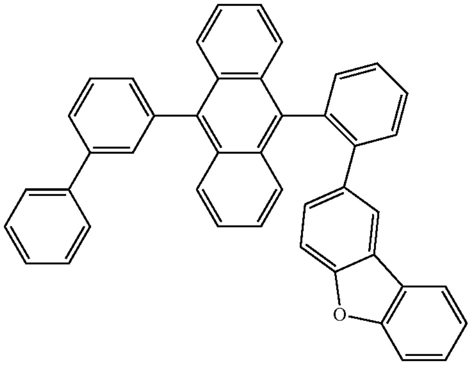
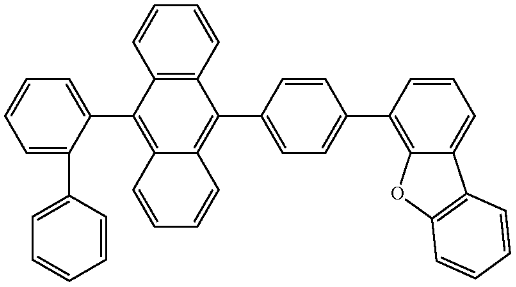
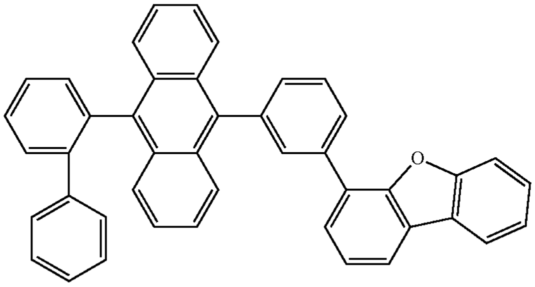

-continued
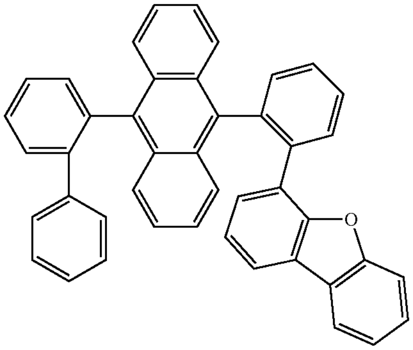
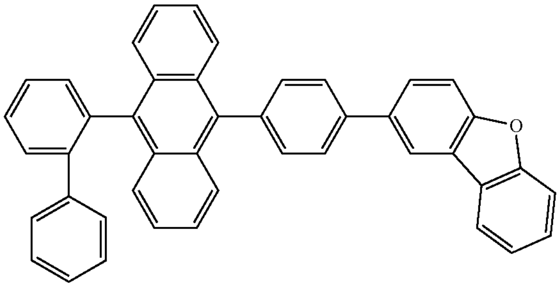
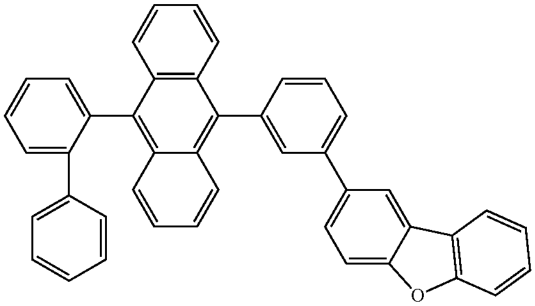
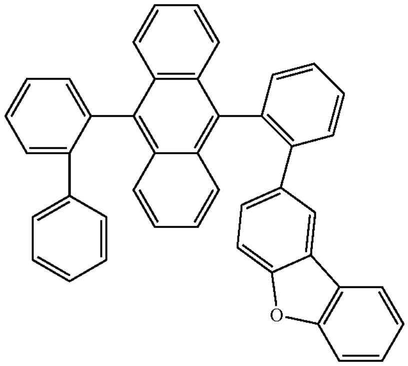
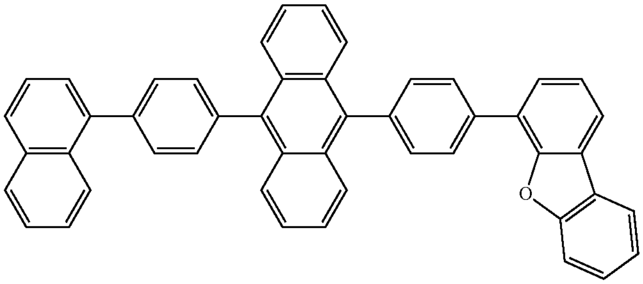
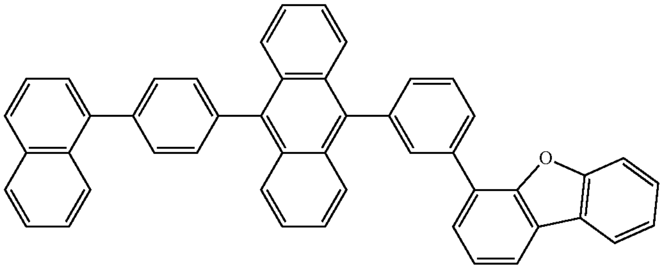
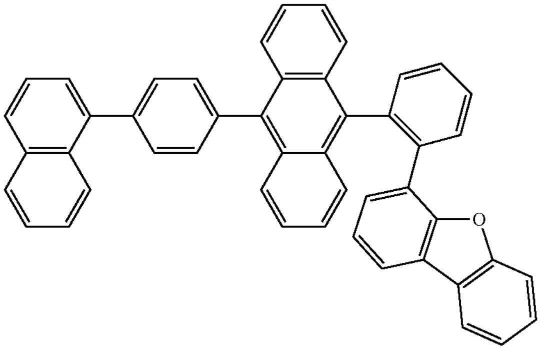

-continued
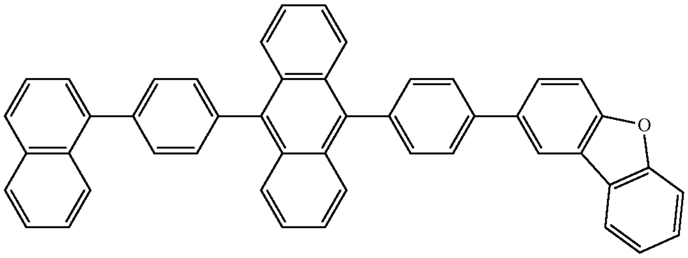
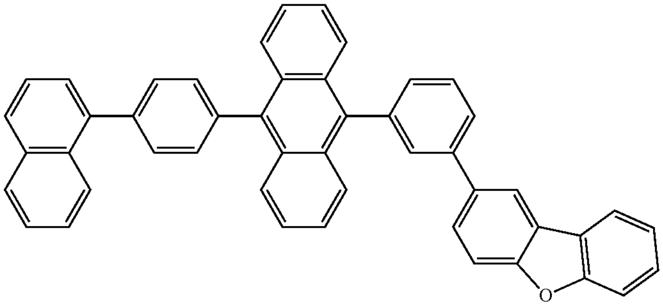
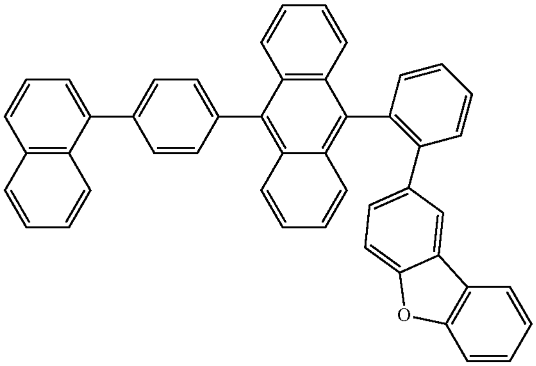
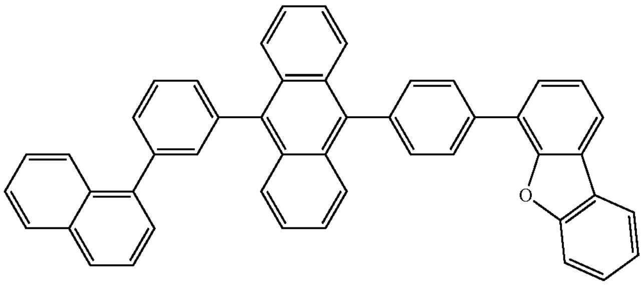
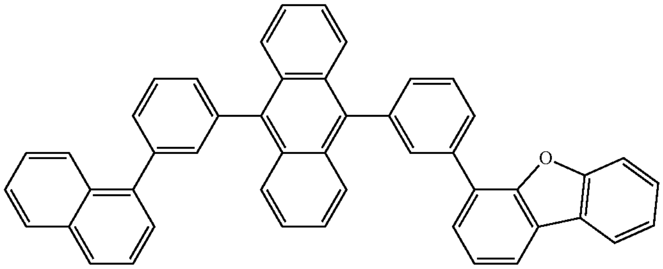

-continued
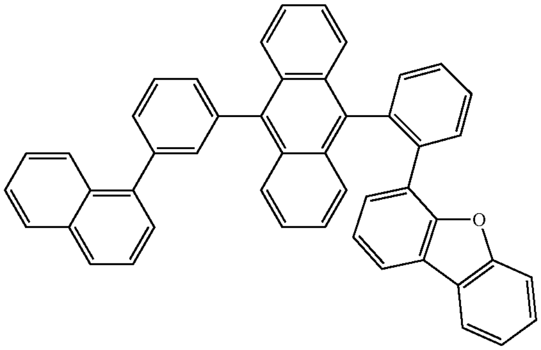
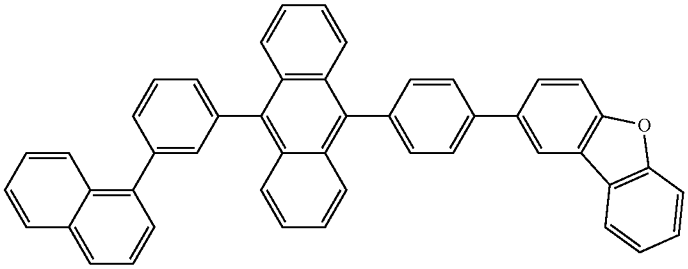
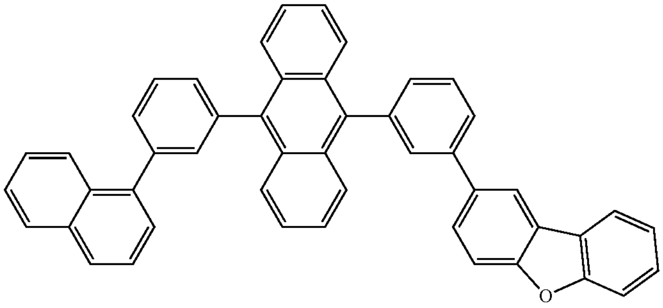
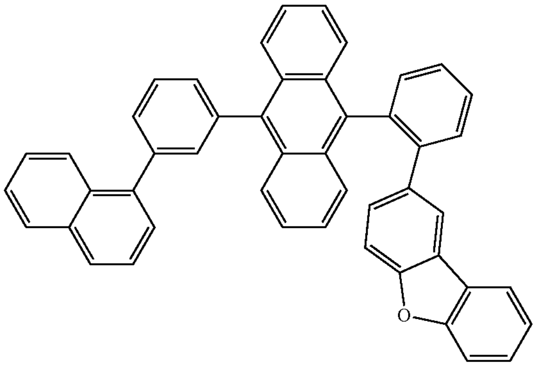
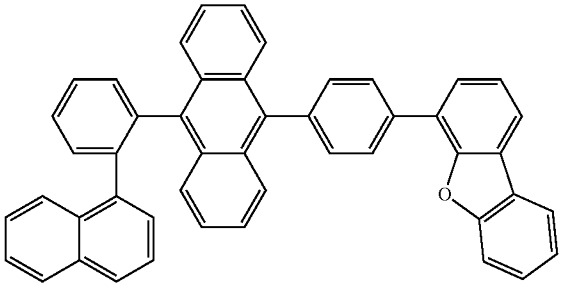
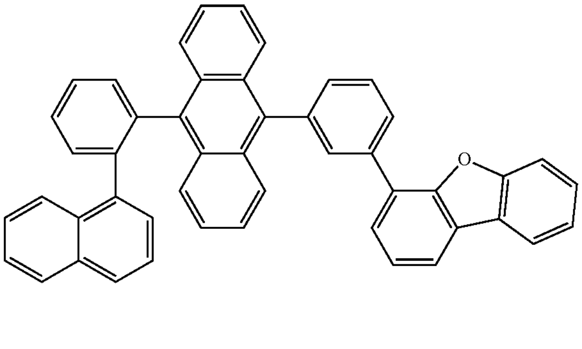
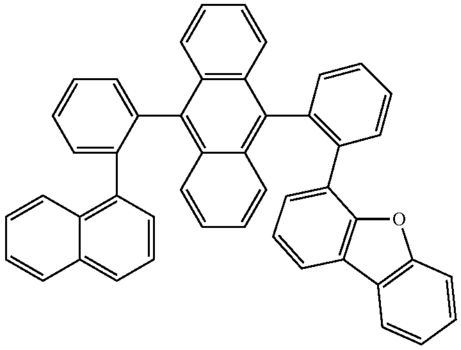

-continued
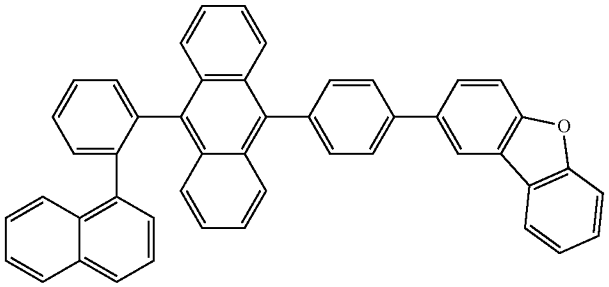
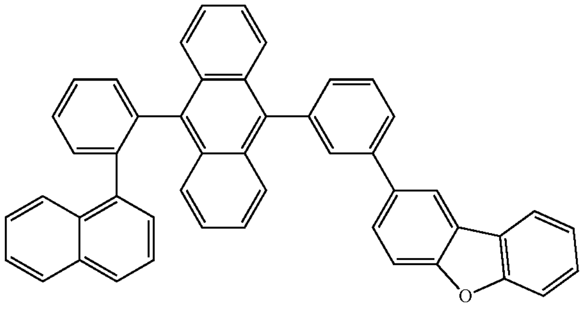
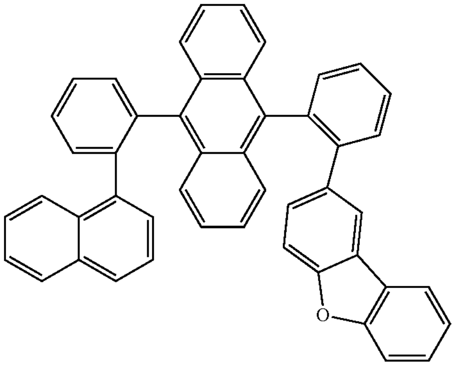
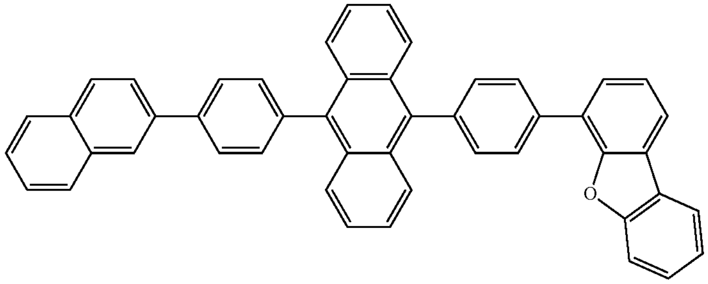
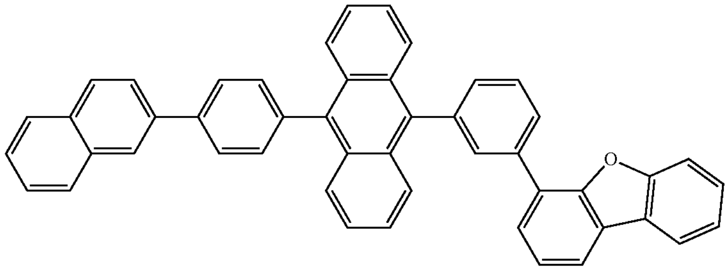
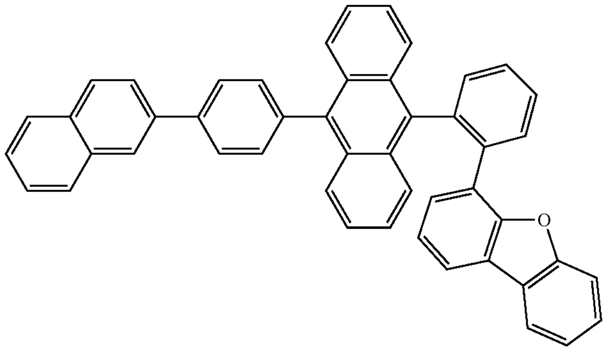

-continued
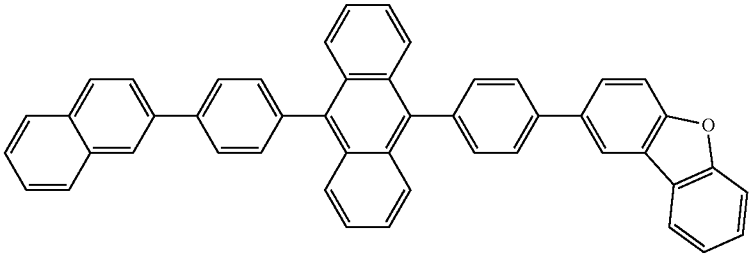
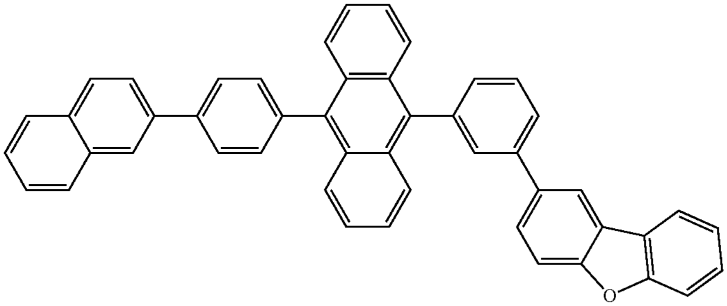
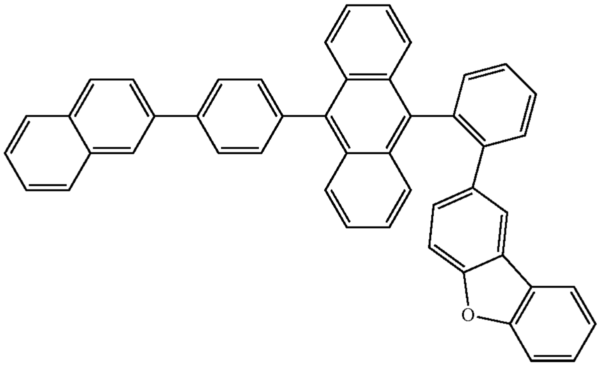
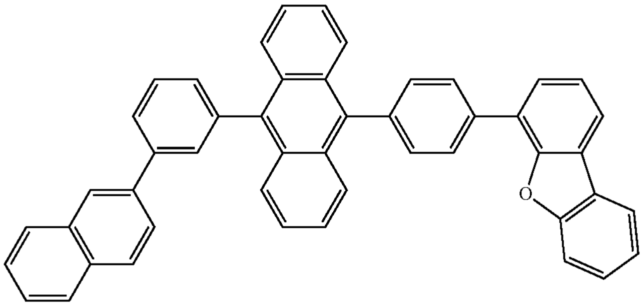
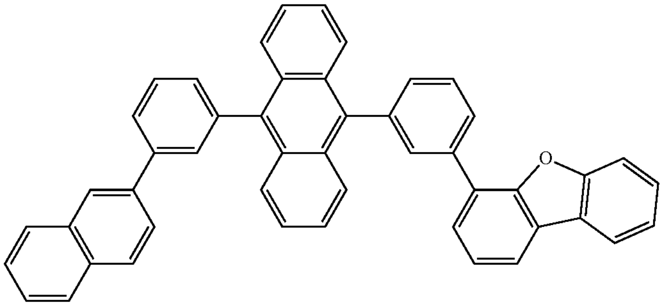

-continued
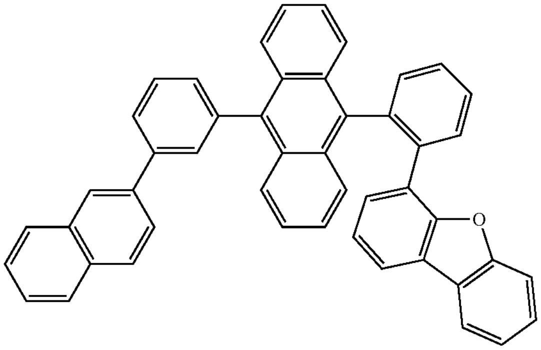
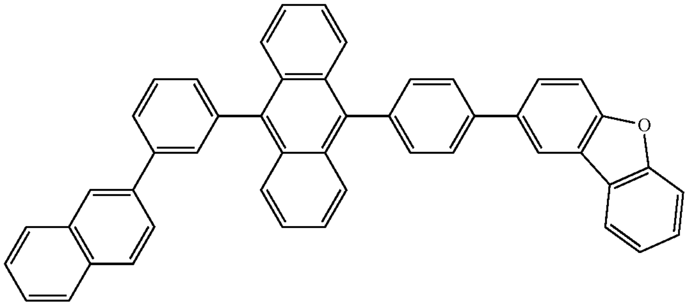
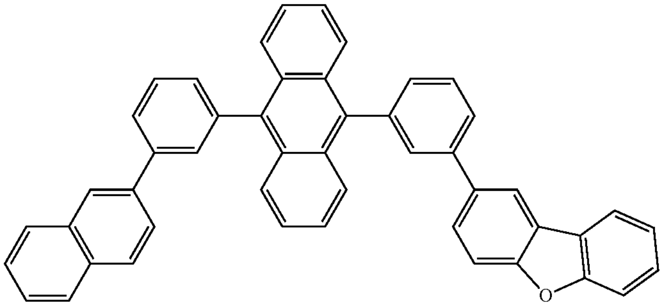
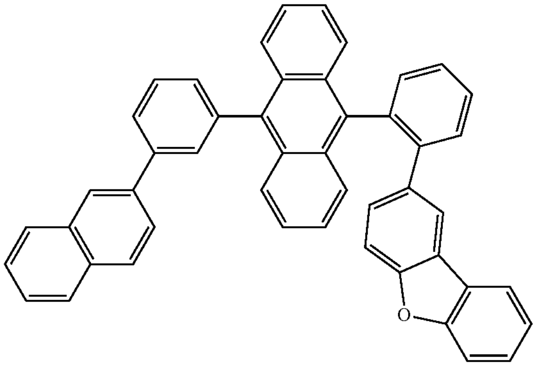
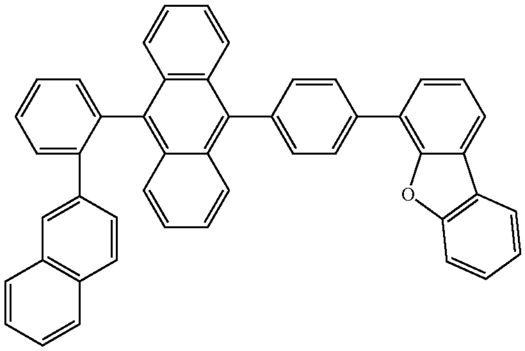
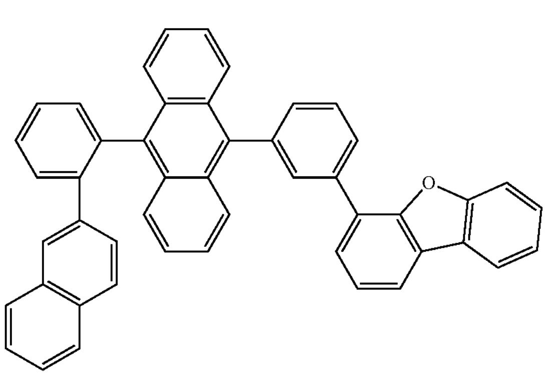
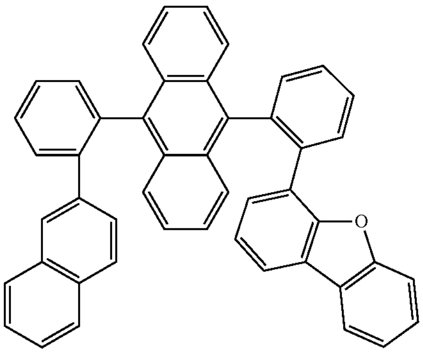

-continued
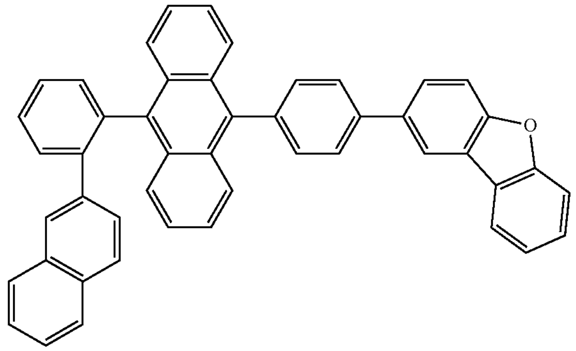
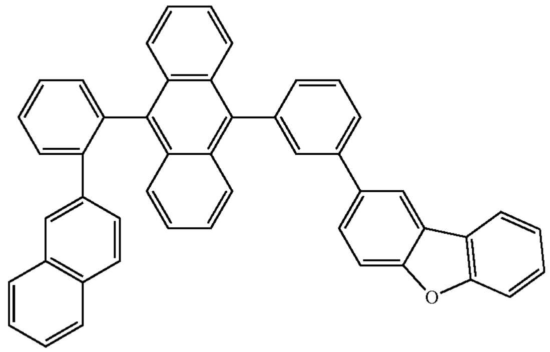
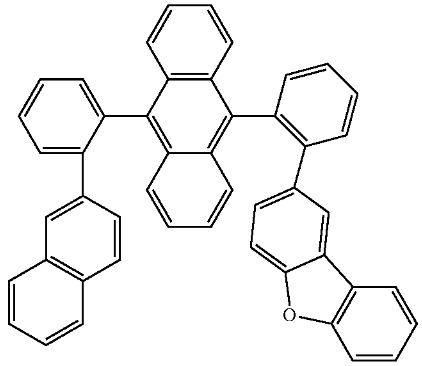
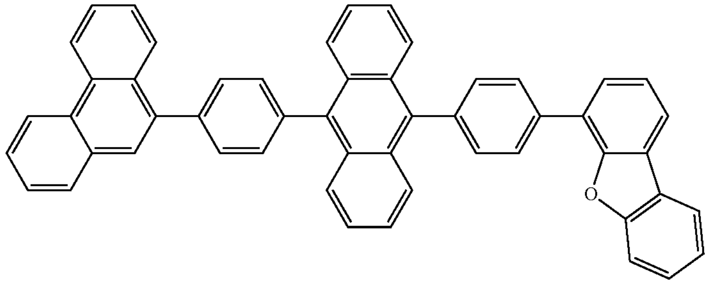
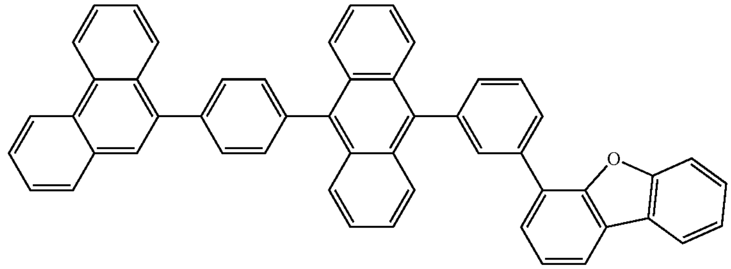
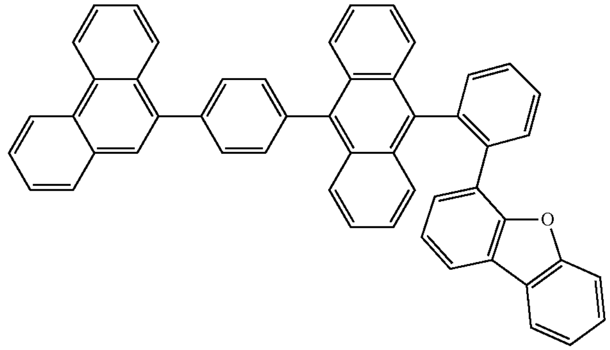
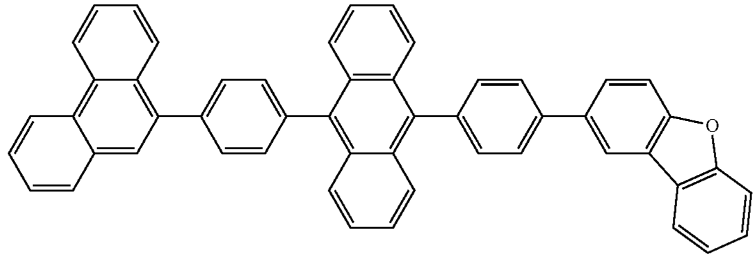

-continued
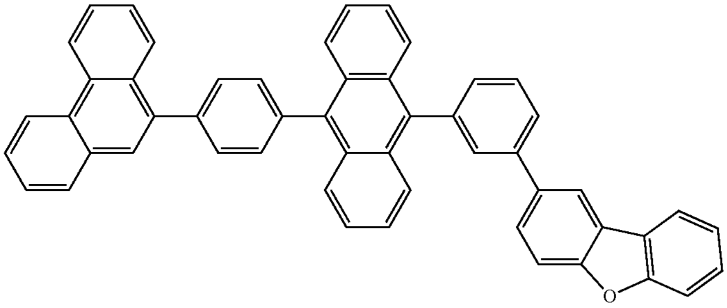
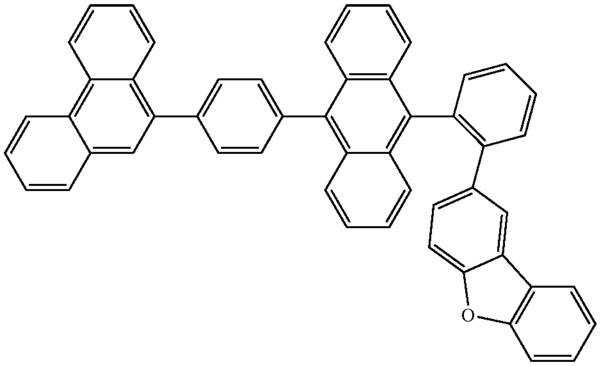
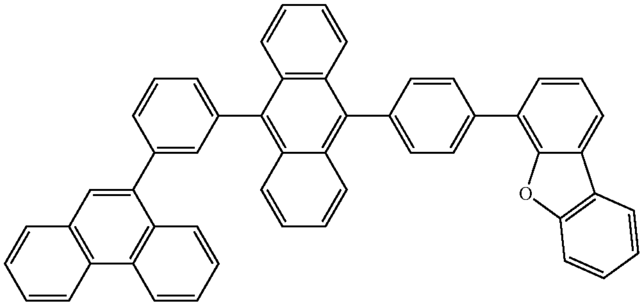
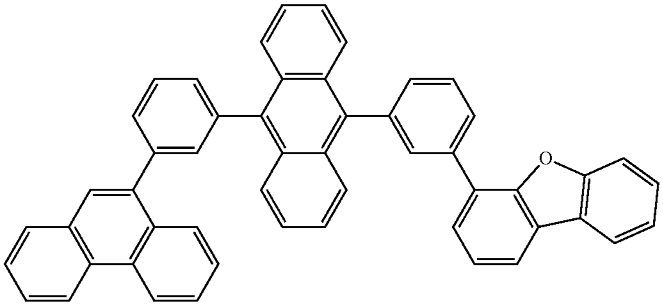
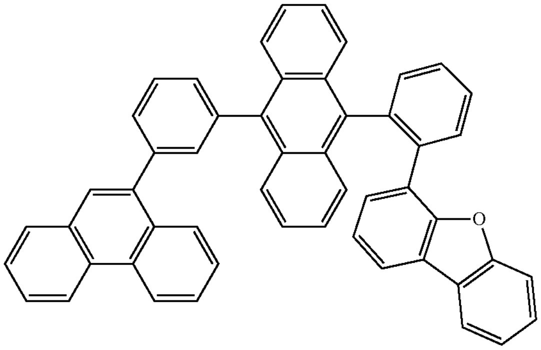

-continued
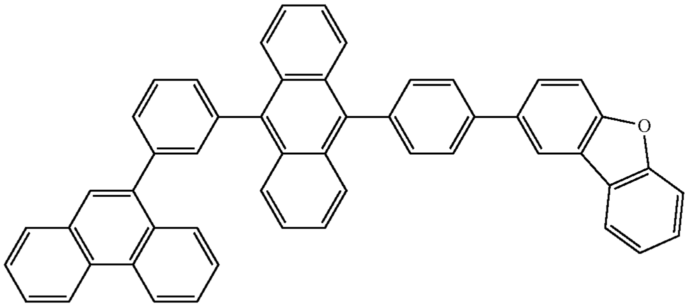
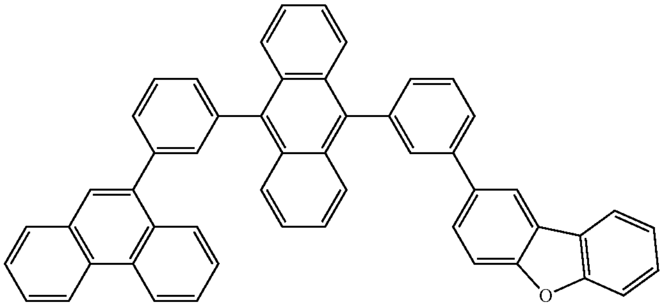
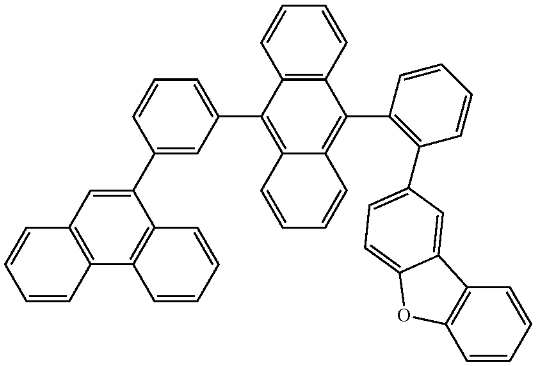
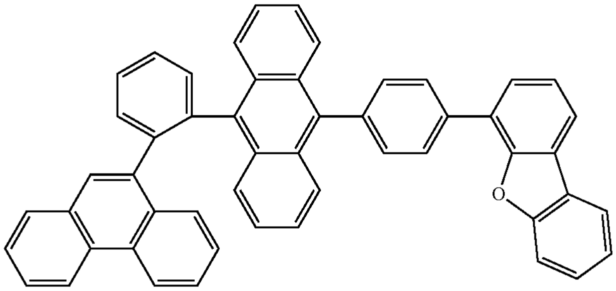
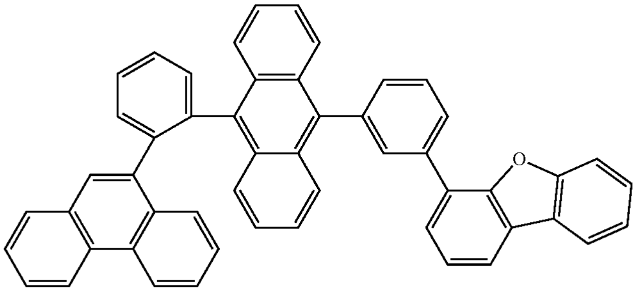
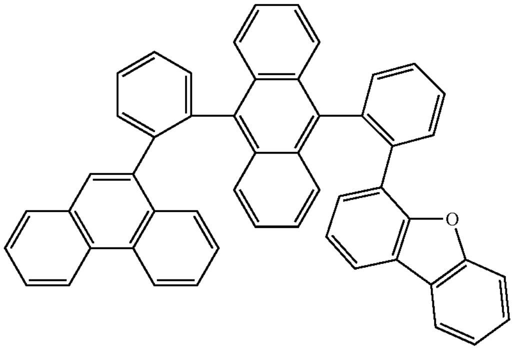
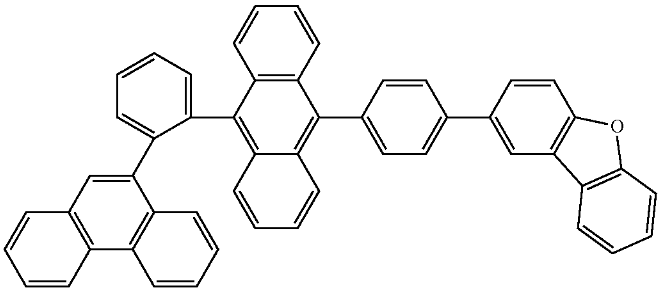

-continued
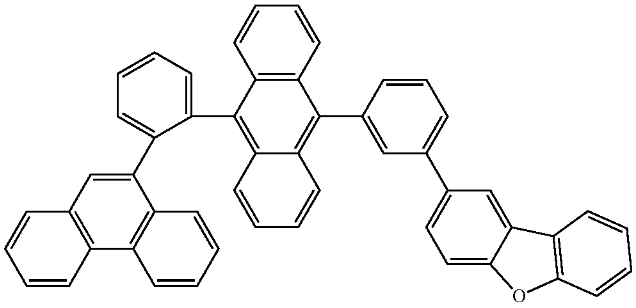
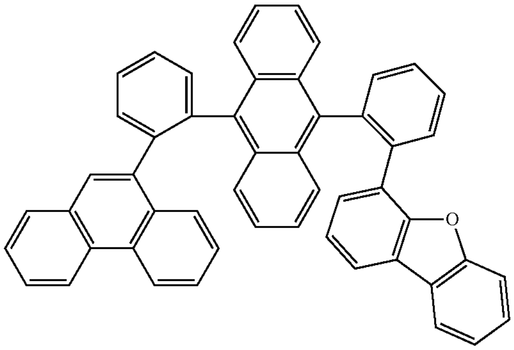
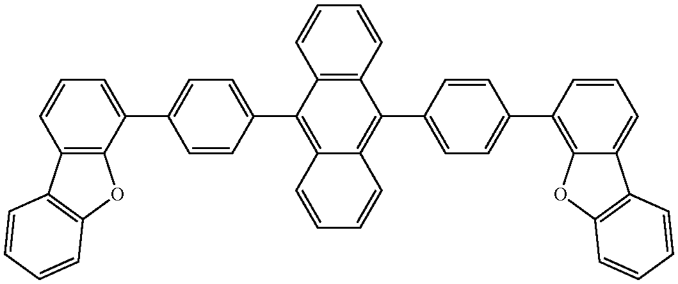
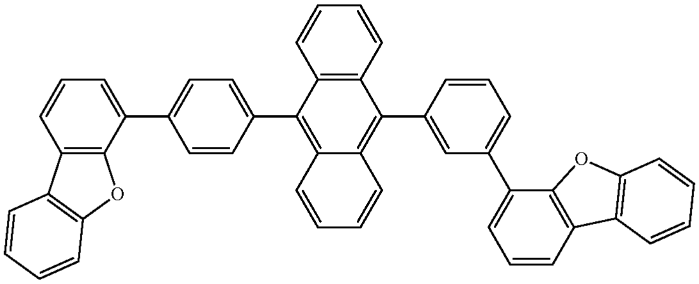
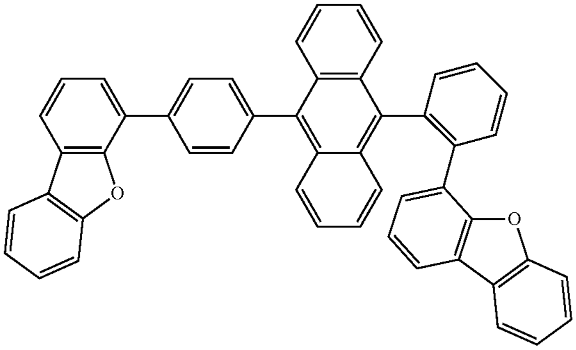
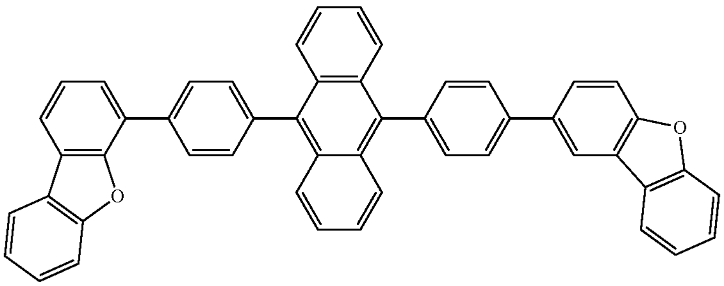

-continued
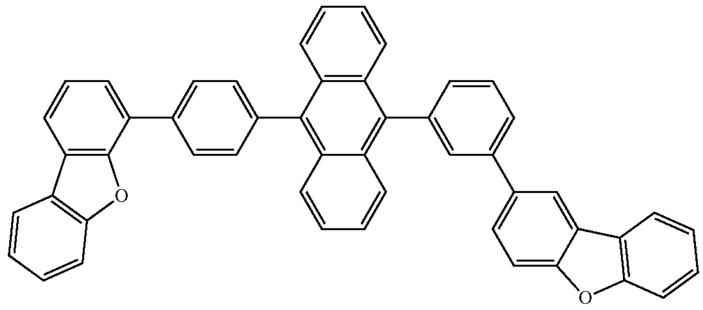
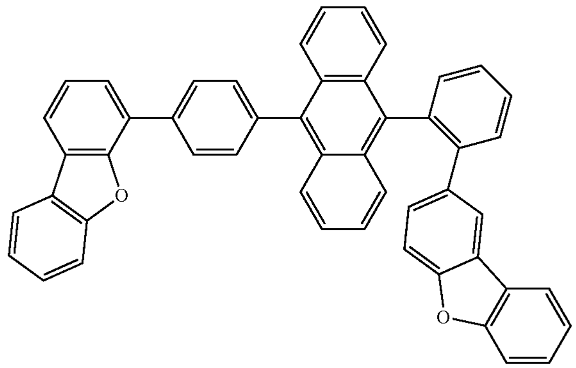
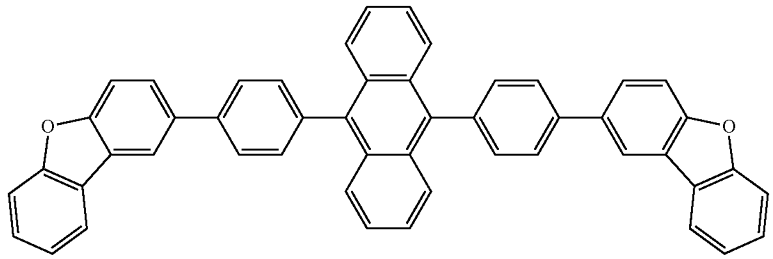
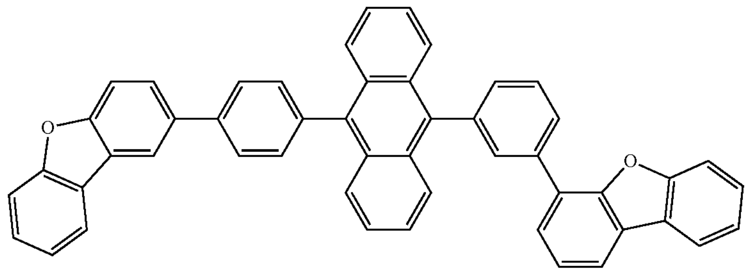
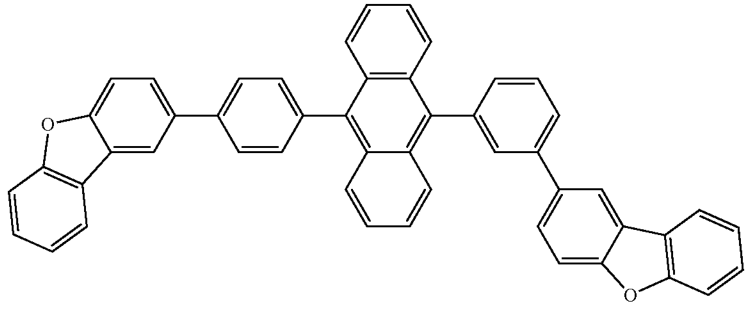

-continued
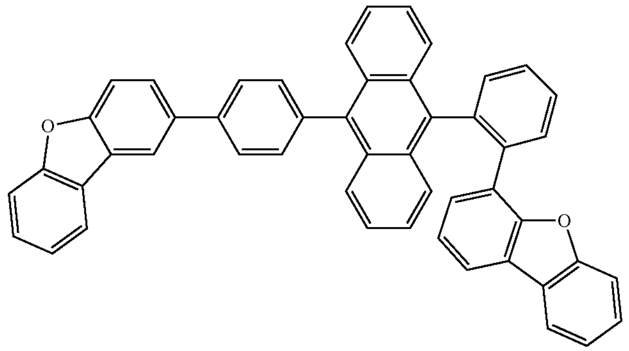
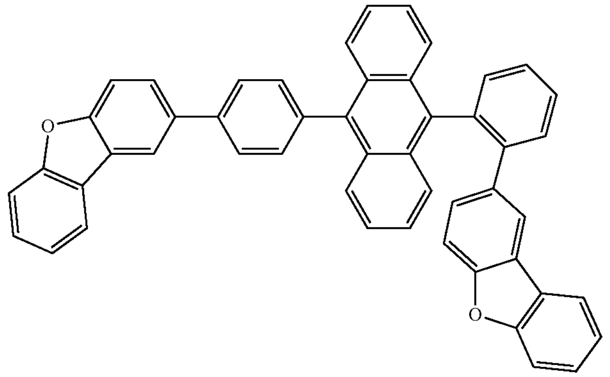
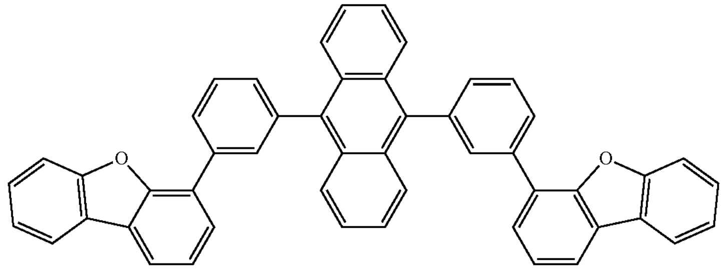
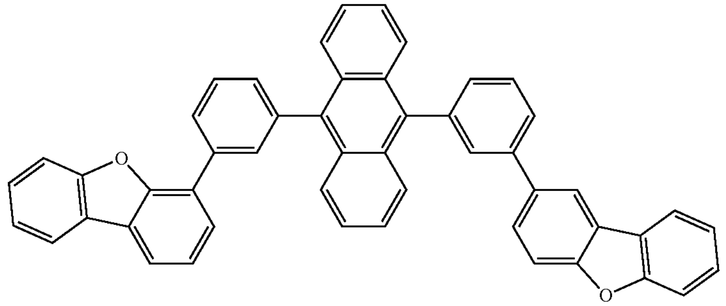
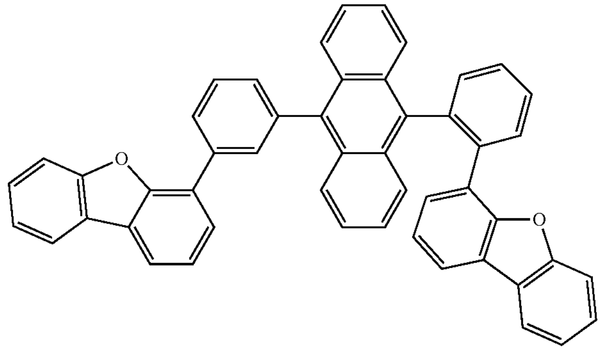

-continued
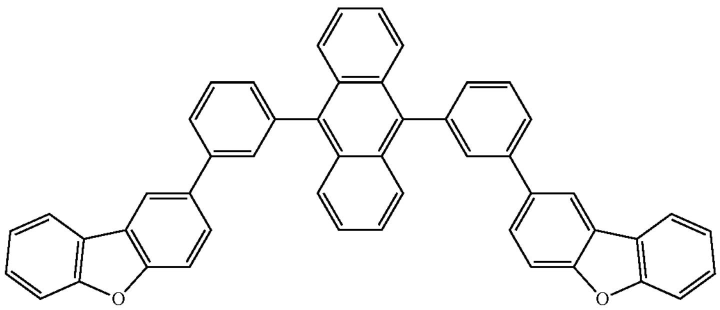
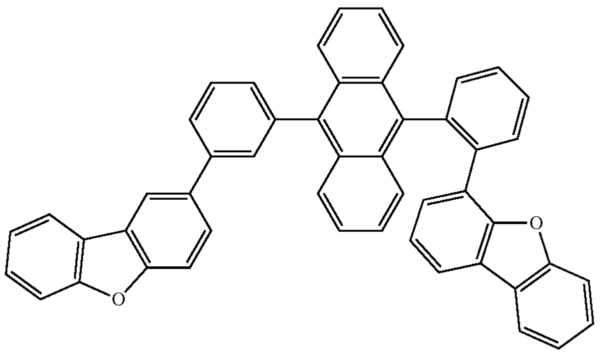
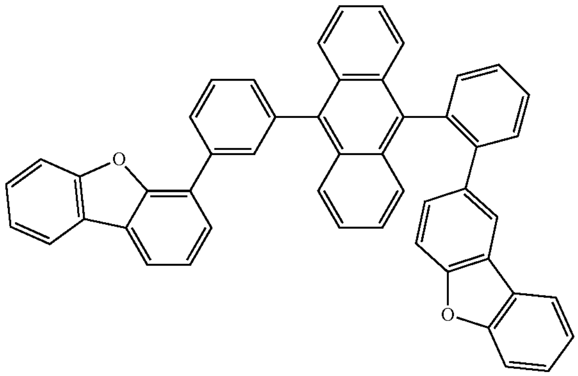
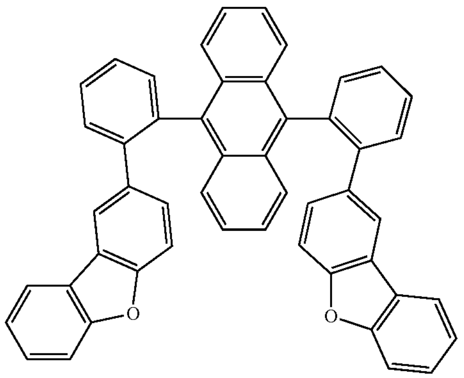
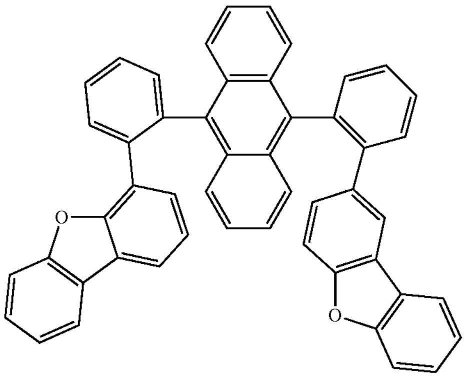
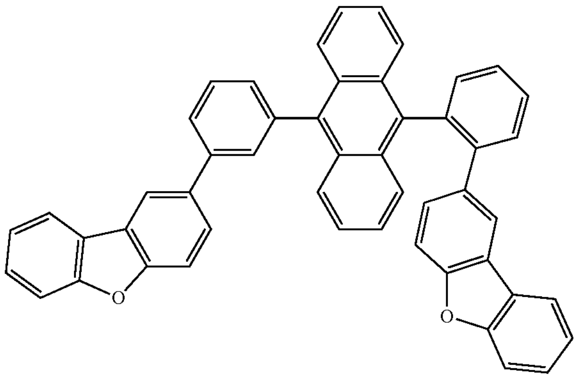
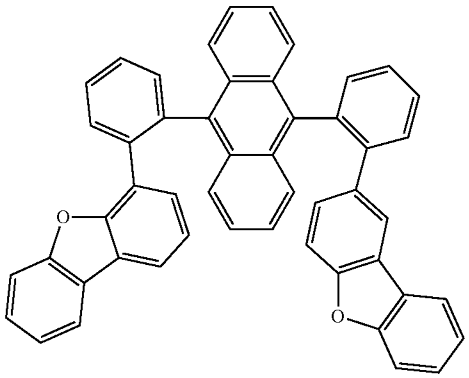
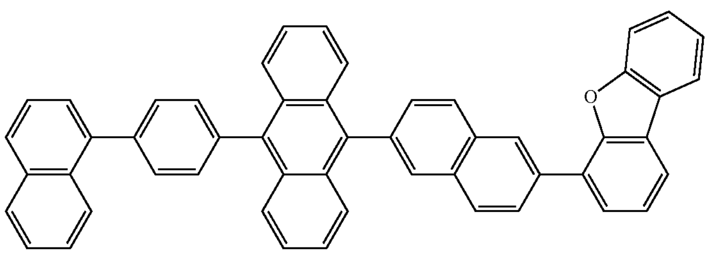

-continued
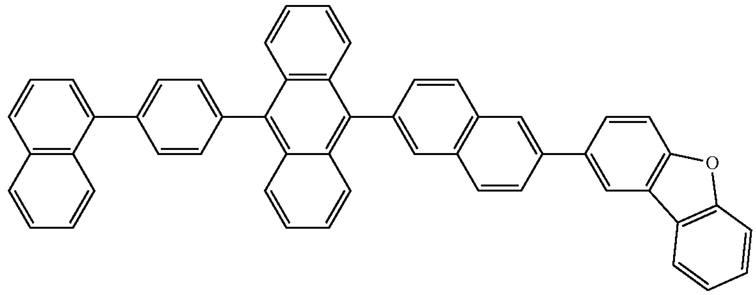
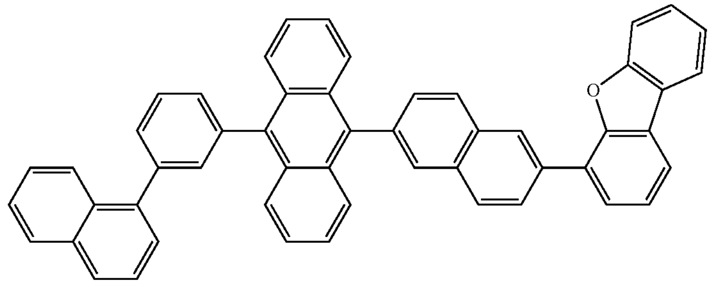
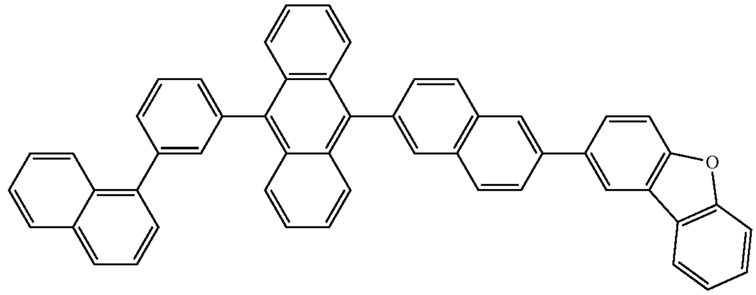
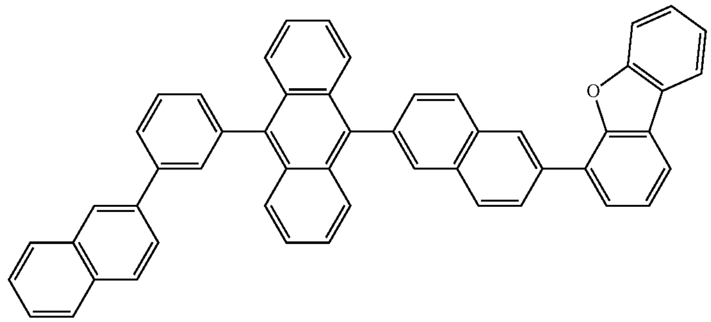
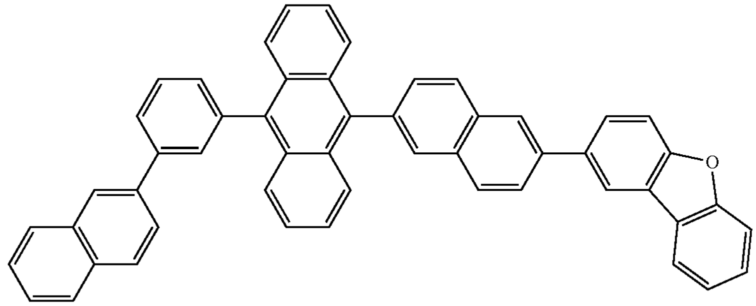

-continued
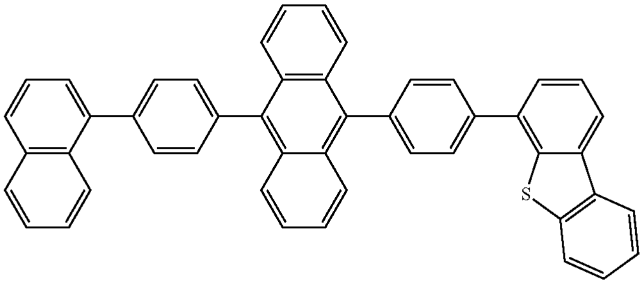
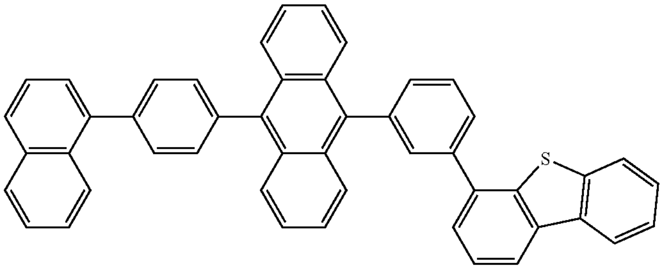
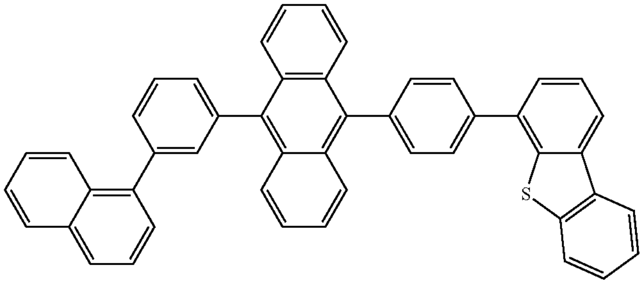
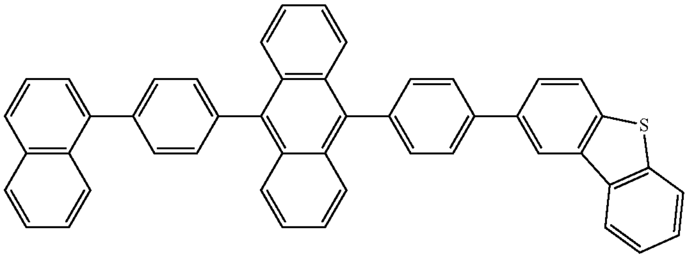
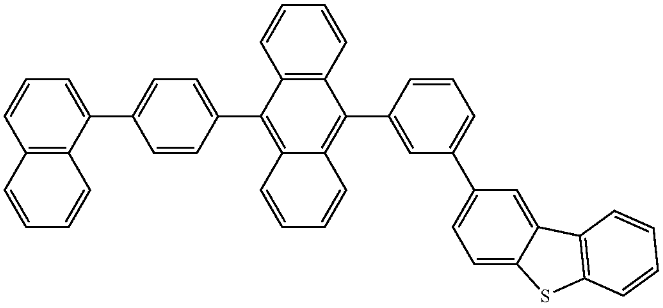
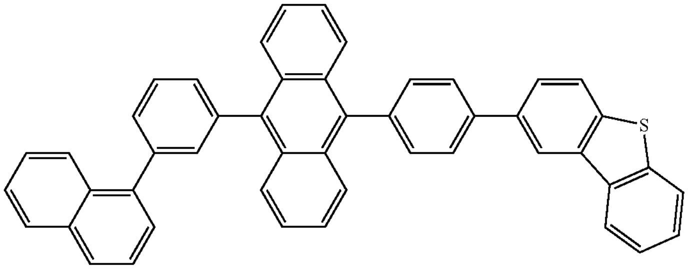

-continued
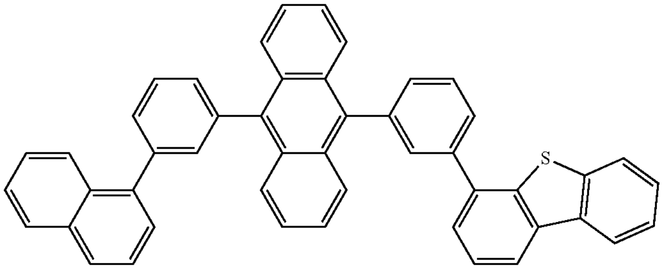
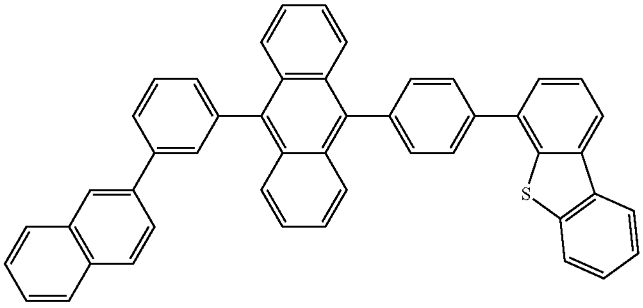
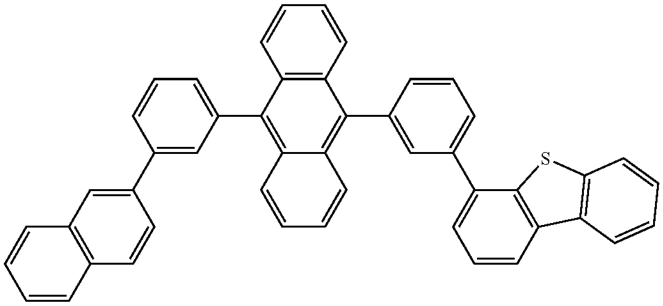
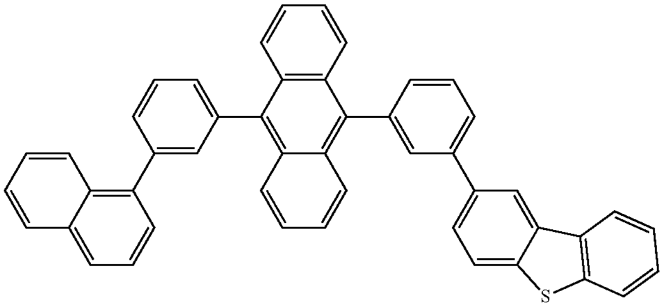
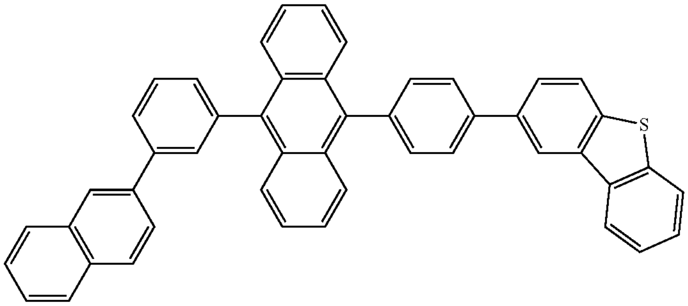

-continued
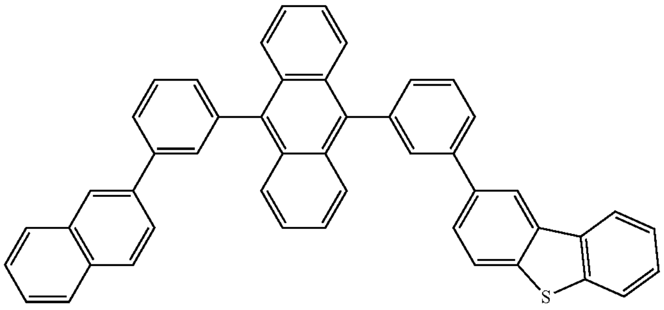
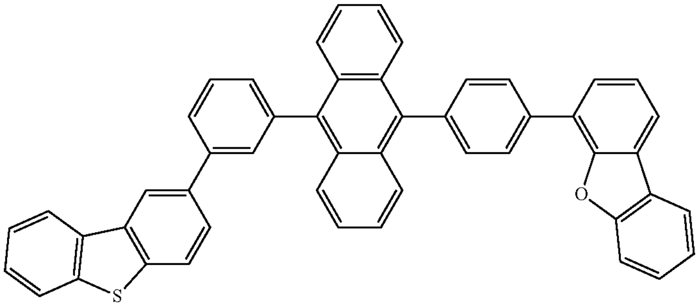
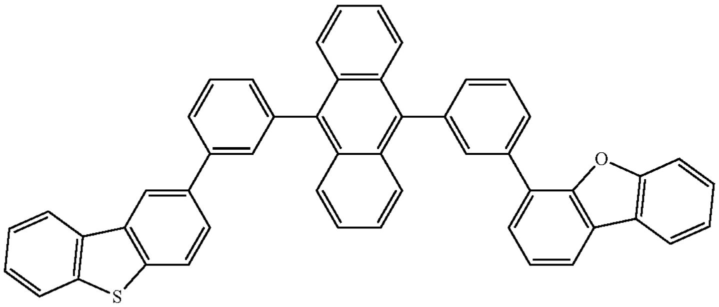
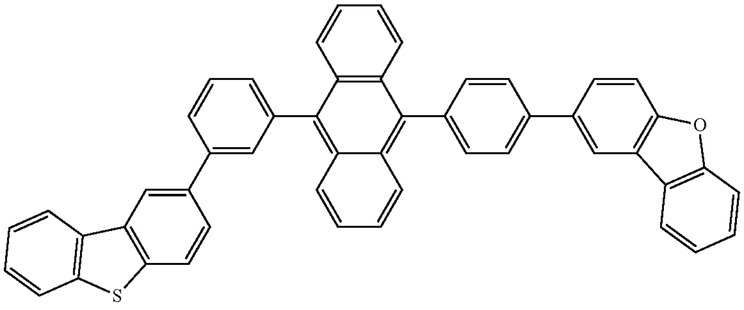
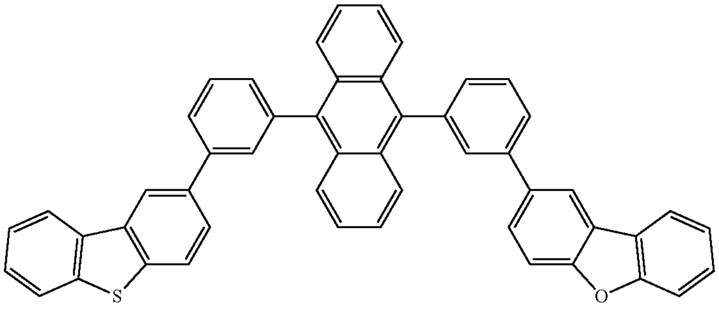

-continued
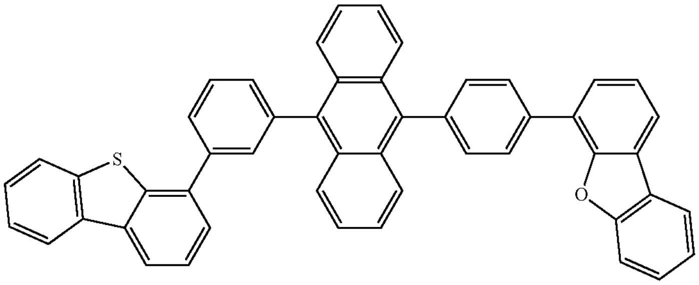
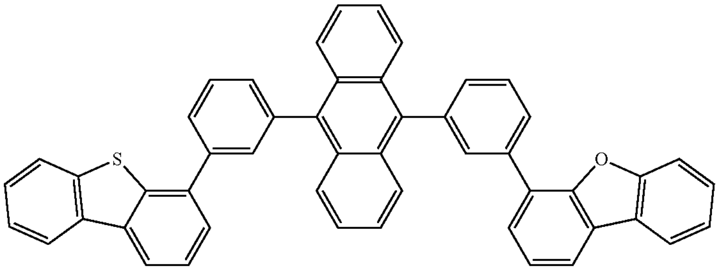
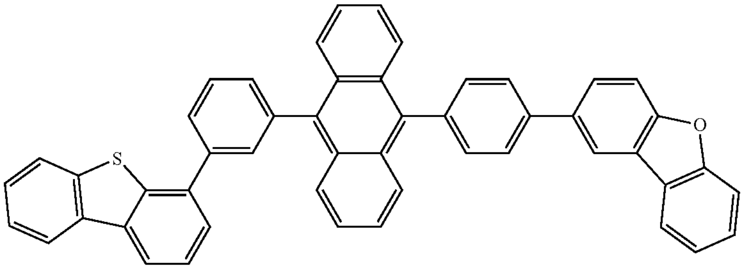
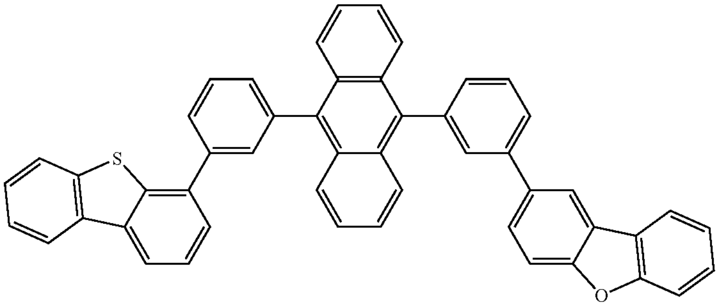
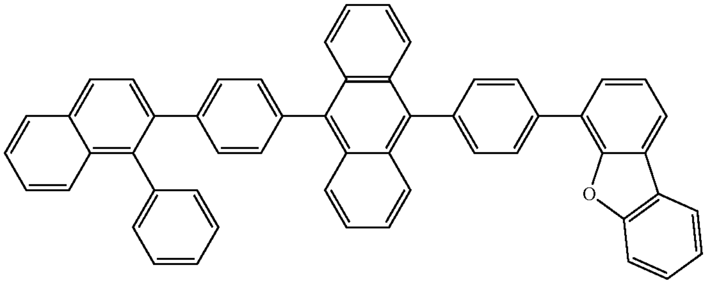
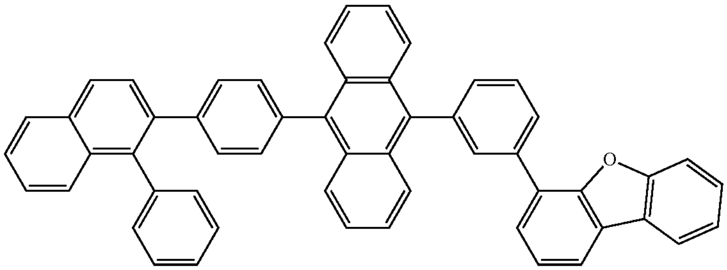

-continued
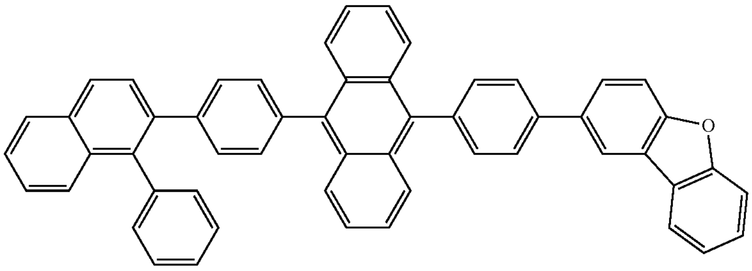
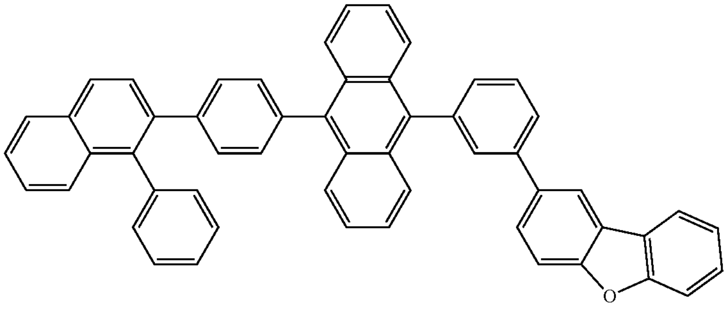
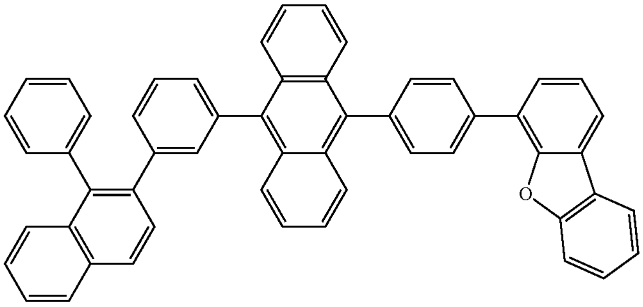
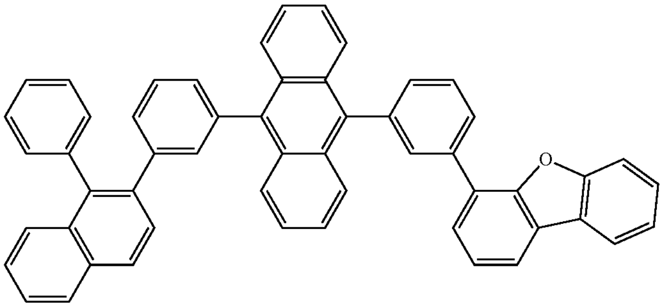
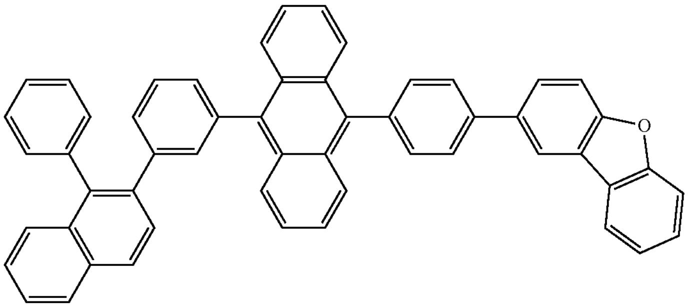

-continued

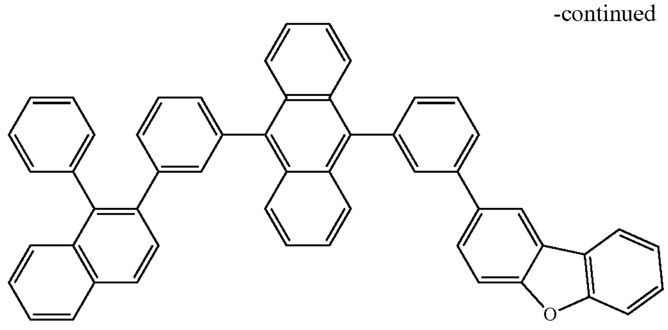

The anthracene derivative of the present invention can be incorporated alone or as a component of a mixture into each of an organic EL device and a material for an organic EL device, and a material for an organic EL device of the present invention and a light emitting material for an organic EL device of the present invention each contain the anthracene derivative.

An organic EL device of the present invention relates to an organic EL device including an organic thin film layer formed of one or more layers including at least a light emitting layer, the organic thin film layer being interposed between a cathode and an anode, in which at least one layer of the organic thin film layer contains the anthracene derivative of the present invention alone or as a component of a mixture.

The anthracene derivative of the present invention may be incorporated into any layer of the above organic thin film layer; the derivative is particularly preferably used in a light emitting zone, and is more preferably used in the light emitting layer because an excellent organic EL device is obtained. In addition, the anthracene derivative of the present invention is preferably incorporated as a light emitting material, and is more preferably incorporated as a host material. The light emitting layer contains the derivative at a content of preferably 10 to 100 wt %, or more preferably 50 to 99 wt %. In addition, the light emitting layer preferably further contains a fluorescent or phosphorescent dopant.

The fluorescent dopant is preferably a compound selected from, for example, an amine-based compound, an aromatic compound, a chelate complex such as a tris(8-quinolinolato) aluminum complex, a coumarin derivative, a tetraphenylbutadiene derivative, a bisstyrylarylene derivative, and an oxadiazole derivative in accordance with a requested luminescent color. An arylamine compound and an aryldiamine compound are particularly preferable examples of such compound; out of these compounds, a styrylamine compound, a styryldiamine compound, an aromatic amine compound, or an aromatic diamine compound is more preferable, and a fused polycyclic aromatic compound (excluding an amine compound) is still more preferable. One kind of those fluorescent dopants may be used alone, or two or more kinds of them may be used in combination.

Compounds each represented by the following general formula (A) are preferable as such styrylamine compound and styryldiamine compound as described above.

(A)

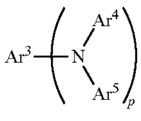

(In the formula, $Ar^3$ represents a group selected from a phenyl group, a naphthyl group, a biphenyl group, a terphenyl group, a stilbene group, and a distyrylaryl group, $Ar^4$ and $Ar^5$ each represent a hydrogen atom or an aromatic hydrocarbon group having 6 to 20 carbon atoms, and each of $Ar^3$, $Ar^4$, and $Ar^5$ may be substituted, p represents an integer of 1 to 4, or preferably 1 or 2, one of $Ar^3$ to $Ar^5$ represents a group containing a styryl group, and at least one of $Ar^4$ and $Ar^5$ is more preferably substituted by a styryl group.)

Here, examples of the aromatic hydrocarbon group having 6 to 20 carbon atoms include a phenyl group, a naphthyl group, an anthranyl group, a phenanthryl group, and a terphenyl group.

Compounds each represented by the following general formula (B) are preferable as the aromatic amine compound and the aromatic diamine compound.

(B)

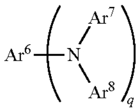

(In the formula, $Ar^6$ to $Ar^8$ each represent a substituted or unsubstituted aryl group having 5 to 40 ring carbon atoms, and q represents an integer of 1 to 4, or preferably 1 or 2.)

Here, examples of the aryl group having 5 to 40 ring carbon atoms include a phenyl group, a naphthyl group, an anthranyl group, a phenanthryl group, a pyrenyl group, a coronyl group, a biphenyl group, a terphenyl group, a pyrrolyl group, a furanyl group, a thiophenyl group, a benzothiophenyl group, an oxadiazolyl group, a diphenylanthranyl group, an indolyl group, a carbazolyl group, a pyridyl group, a benzoquinolyl group, a fluoranthenyl group, an acenaphtho fluoranthenyl group, a stilbene group, a perylenyl group, a chrysenyl group, a picenyl group, a triphenylenyl group, a rubicenyl group, a benzoanthracenyl group, a phenylanthracenyl group, a bisanthracenyl group, and aryl groups represented by the following general formulae (C) and (D). Preferred are a naphthyl group, an anthranyl group, a chrysenyl group, a pyrenyl group, and aryl groups represented by the general formula (D).

(C)

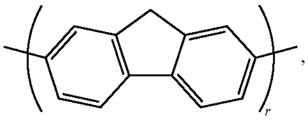

,

-continued (D)

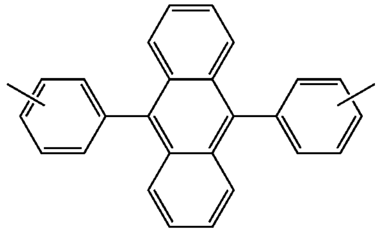

(In the general formula (C), r represents an integer of 1 to 3.)

Note that examples of preferred substituent which is substituted with substances on the aryl group include alkyl groups each having 1 to 6 carbon atoms (such as an ethyl group, a methyl group, an i-propyl group, an n-propyl group, an s-butyl group, a t-butyl group, a pentyl group, a hexyl group, a cyclopentyl group, and a cyclohexyl group), alkoxy groups having 1 to 6 carbon atoms (such as an ethoxy group, a methoxy group, an i-propoxy group, an n-propoxy group, an s-butoxy group, a t-butoxy group, a pentoxy group, a hexyloxy group, a cyclopentoxy group, and a cyclohexyloxy group), aryl groups having 5 to 40 ring carbon atoms, amino groups substituted by aryl groups having 5 to 40 ring carbon atoms, and ester groups containing an aryl group having 5 to 40 ring carbon atoms, ester groups containing an alkyl group having 1 to 6 carbon atoms, a cyano groups, a nitro group, and halogen atoms.

Examples of the fused polycyclic aromatic compound (excluding amine compounds) include fused polycyclic aromatic compounds such as naphthalene, anthracene, phenanthrene, pyrene, coronene, biphenyl, terphenyl, pyrrole, furan, thiophene, benzothiophene, oxadiazole, indole, carbazole, pyridine, benzoquinoline, fluoranthenine, benzofluoranthene, acenaphtho fluoranthenine, stilbene, perylene, chrysene, picene, triphenylenine, rubicene, and benzoanthracene, and derivatives thereof.

The phosphorescent dopant incorporated in the light emitting layer is preferably a metal complex compound containing at least one metal selected from the group consisting of Ir, Ru, Pd, Pt, Os, and Re. The ligand of the metal complex compound preferably include at least one skeleton selected from a phenylpyridine skeleton, a bipyridyl skeleton, and a phenanthroline skeleton. Specific examples of the metal complex include tris(2-phenylpyridine)iridium, tris(2-phenylpyridine)ruthenium, tris(2-phenylpyridine)palladium, bis(2-phenylpyridine)platinum, tris(2-phenylpyridine)osmium, tris(2-phenylpyridine)rhenium, octaethyl platinum porphyrin, octaphenyl platinum porphyrin, octaethyl palladium porphyrin, and octaphenyl palladium porphyrin. However, the metal complex is not limited thereto, and the appropriate complex is selected in terms of a desired luminescent color, a device performance, and a relationship with a host compound.

Hereinafter, the device constitution of the organic EL device of the present invention will be described.

The organic EL device of the present invention is a device obtained by forming an organic thin film layer formed of one or multiple layers between an anode and a cathode. When the device is of a one-layer type, a light emitting layer is provided between the anode and the cathode. The light emitting layer contains a light emitting material, and may further contain a hole injecting material for transporting a hole injected from the anode to the light emitting material or an electron injecting material for transporting an electron injected from the cathode to the light emitting material. However, the light emitting material is preferably as follows: the material brings together extremely high fluorescent quantum efficiency, a high hole transporting ability, and a high electron transporting ability, and can be formed into a uniform thin film.

A multi-layer type organic EL device is obtained by laminating multiple layers; the device is formed of an anode, a hole injecting layer, a light emitting layer, and a cathode, of an anode, a light emitting layer, an electron injecting layer, and a cathode, of an anode, a hole injecting layer, a light emitting layer, an electron injecting layer, and a cathode, or of an anode, a hole injecting layer, a hole transporting layer, a light emitting layer, an electron transporting layer, an electron injecting layer, and a cathode.

The light emitting layer may further use a known light emitting material, doping material, hole injecting material, or electron injecting material in addition to the light emitting material represented by any one of the general formulae of the present invention as required. Any heavy metal complex typified by phosphorescent iridium as well as a conventional fluorescent material can be used as the doping material. Reductions in luminance and lifetime of the organic EL device due to quenching can be prevented by providing the device with a multi-layer structure. A light emitting material, any other doping material, a hole injecting material, and an electron injecting material can be used in combination as required. In addition, the other doping material can: improve the emission luminance and luminous efficiency of the device; and cause the device to emit red or white light.

In addition, each of the hole injecting layer, the light emitting layer, and the electron injecting layer may be formed of two or more layers. At that time, in the case of the hole injecting layer, a layer that injects a hole from an electrode is referred to as a hole injecting layer, and a layer that receives the hole from the hole injecting layer and transports the hole to the light emitting layer is referred to as a hole transporting layer. Similarly, in the case of the electron injecting layer, a layer that injects an electron from an electrode is referred to as an electron injecting layer, and a layer that receives the electron from the electron injecting layer and transports the electron to the light emitting layer is referred to as an electron transporting layer. Each of those layers is selected and used depending on various factors such as the energy level of a material for the layer, the heat resistance of the layer, and the adhesiveness of the layer with the organic thin film layer or a metal electrode.

Examples of the light emitting material or host material that can be used in the light emitting layer together with anthracene derivatives represented by the general formula of the present invention include, but not limited to, anthracene derivatives, arylanthracene derivatives, naphthalene derivatives, phenanthrene derivatives, pyrene derivatives, tetracene derivatives, coronene derivatives, chrysene derivatives, fluorescein derivatives, perylene derivatives, phthaloperylene derivatives, naphthaloperylene derivatives, perinone derivatives, phthaloperinone derivatives, naphthaloperinone derivatives, diphenylbutadiene derivatives, tetraphenylbutadiene derivatives, cumarin derivatives, oxadiazole derivatives, aldazine derivatives, bisbenzoxazoline derivatives, bisstyryl derivatives, pyrazine derivatives, cyclopentadiene derivatives, quinoline metal complex derivatives, aminoquinoline metal complex derivatives, benzoquinoline metal complex derivatives, imine derivatives, diphenylethylene derivatives, vinylanthracene derivatives, diaminocarbazole derivatives, pyran derivatives, thiopyran derivatives, polymethine derivatives, merocyanine derivatives, imidazole chelated oxynoid compounds, quinacridone derivatives, rubrene derivatives, stilbene-based derivatives, and fluorescent dyes.

A compound having the following characteristics is a preferable hole injecting/transporting material: the compound has an ability to transport a hole, exerts a hole injecting effect from the anode and an excellent hole injecting effect on the light emitting layer or the light emitting material, prevents the transfer of an exciton produced in the light emitting layer toward the electron injecting layer or the electron injecting material, and is excellent in ability to form a thin film. Specific examples thereof include, but not limited to, phthalocyanine derivatives, naphthalocyanine derivatives, porphyrine derivatives, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, a bendizine type triphenylamine, a styrylamine type triphenylamine, a diamine type triphenylamine, derivatives thereof, polyvinyl carbazole, polysilane, and polymer materials such as conductive polymers.

Of the hole injecting or transporting materials that can be used in the organic EL device of the present invention, further effective materials are aromatic tertiary amine derivatives and phthalocyanine derivatives.

Specific examples of the aromatic tertiary amine derivatives include, but not limited to, triphenylamine, tritolylamine, tolyldiphenylamine, N,N'-diphenyl-N,N-'(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, N,N'-(methylphenyl)-N,N'-(4-n-butylphenyl)-phenanthrene-9,10-diamine, N,N-bis(4-di-4-tolylaminophenyl)-4-phenylcyclohexane, and oligomers and polymers each having one of those aromatic tertiary amine skeletons.

Specific examples of the phthalocyanine (Pc) derivative include, but not limited to, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc-O-GaPc, and naphthalocyanine derivatives.

A compound having the following characteristics is a preferable electron injecting/transporting material: the compound has an ability to transport an electron, exerts an electron injecting effect from the cathode and an excellent electron injecting effect on the light emitting layer or the light emitting material, prevents the transfer of an exciton produced in the light emitting layer toward the electron injecting layer, and is excellent in ability to form a thin film. Specific examples include, but not limited to, fluorenone, anthraquinodimethane, diphenoquinone, thipyrandioxide, oxazole, oxadiazole, triazole, imidazole, perylenetetracarboxylic acid, fluorenylidene methane, anthraquinodimethane, anthrone, and derivatives thereof. Alternatively, the property with which charge is injected can be improved by adding an electron accepting substance to the hole injecting material and an electron donating substance to the electron injecting material.

An additionally effective electron injecting material in the organic EL device of the present invention is a metal complex compound or a nitrogen-containing five-membered ring derivative.

Specific examples of the metal complex compound include, but not limited to, 8-hydroxyquinolinate lithium, bis(8-hydroxyquinolinate)zinc, bis(8-hydroxyquinolinate)copper, bis(8-hydroxyquinolinate)manganese, tris(8-hydroxyquinolinate)aluminum, tris(2-methyl-8-hydroxyquinolinate)aluminum, tris(8-hydroxyquinolinate)gallium, bis(10-hydroxybenzo[h]quinolinate)beryllium, bis(10-hydroxybenzo[h]quinolinate)zinc, bis(2-methyl-8-quinolinate)chlorogallium, bis(2-methyl-8-quinolinate)(o-cresolate)gallium, bis(2-methyl-8-quinolinate)(1-naphtholate)aluminum, and bis(2-methyl-8-quinolinate)(2-naphtholate)gallium.

In addition, the nitrogen-containing 5-membered derivative is preferably an oxazole, thiazole, oxadiazole, thiadiazole, or triazole derivative. Specific examples thereof include 2,5-bis(1-phenyl)-1,3,4-oxazole, dimethylPOPOP, 2,5-bis(1-phenyl)-1,3,4-thiazole, 2,5-bis(1-phenyl)-1,3,4-oxadiazole, 2-(4'-tert-butylphenyl)-5-(4"-biphenyl)1,3,4-oxadiazole, 2,5-bis(1-naphthyl)-1,3,4-oxadiazole, 1,4-bis[2-(5-phenyloxadiazolyl)]benzene, 1,4-bis[2-(5-phenylozadiazolyl)-4-tert-butylbenzene], 2-(4'-tertbutylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, and 2,5-bis(1-naphthyl)-1,3,4-triazole, 1,4-bis[2-(5-phenyltriazolyl)]benzene.

In addition, as an electron injecting material, compounds represented by the following general formulae (A) to (F) may be used as well.

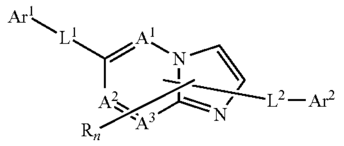

(A)

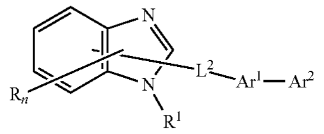

(B)

A nitrogen-containing heterocyclic derivative represented by the general formulae (A) and (B)

(In the general formulae (A) and (B), $A^1$ to $A^3$ each independently represent a nitrogen atom or a carbon atom;

$Ar^1$ represents a substituted or unsubstituted aryl group having 6 to 60 ring carbon atoms, or a substituted or unsubstituted heterocyclic group having 5 to 60 ring atoms, $Ar^2$ represents a hydrogen atom, a substituted or unsubstituted aryl group having 6 to 60 ring carbon atoms, a substituted or unsubstituted heterocyclic group having 5 to 60 ring atoms, a substituted or unsubstituted alkyl group having 1 to 20 carbon atoms, or a substituted or unsubstituted alkoxy group having 1 to 20 carbon atoms, or a divalent group of any one of those;

provided that one of $Ar^1$ and $Ar^2$ represents a substituted or unsubstituted fused ring group having 10 to 60 ring carbon atoms, or a substituted or unsubstituted monohetero fused ring group having 5 to 60 ring atoms;

$L^1$, $L^2$, and L each independently represent a single bond, a substituted or unsubstituted arylene group having 6 to 60 ring carbon atoms, a substituted or unsubstituted heteroarylene group having 5 to 60 ring atoms, or a substituted or unsubstituted fluorenylene group;

R represents a hydrogen atom, a substituted or unsubstituted aryl group having 6 to 60 ring carbon atoms, a substituted or unsubstituted heterocyclic group having 5 to 60 ring atoms, a substituted or unsubstituted alkyl group having 1 to 20 carbon atoms, or a substituted or unsubstituted alkoxy group having 1 to 20 carbon atoms, n represents an integer of 0 to 5, and, when n represents 2 or more, multiple R's may be identical to or different from one another, and multiple R groups adjacent to each other may be bonded to each other to form a carbocyclic aliphatic ring or a carbocyclic aromatic ring; and $R^1$ represents a hydrogen atom, a substituted or unsubstituted aryl group having 6 to 60 ring carbon atoms, a substituted or unsubstituted heteroaryl group having 3 to 60 ring carbon atoms, a substituted or unsubstituted alkyl group having 1 to 20 carbon atoms, a substituted or unsubstituted alkoxy group having 1 to 20 carbon atoms, or $-L^1-Ar^1-Ar^2$).

$$HAr-L-Ar^1—Ar^2 \quad (C)$$

A nitrogen-containing heterocyclic derivative represented by the formula (C) (In the formula: HAr represents a nitrogen-containing heterocyclic ring having 3 to 40 carbon atoms and may have a substituent; L represents a single bond, an arylene group having 6 to 60 ring carbon atoms and may have a substituent, a heteroarylene group having 5 to 60 ring atoms and may have a substituent, or a fluorenylene group which may have a substituent;

$Ar^1$ represents a divalent aromatic hydrocarbon group which has 6 to 60 ring carbon atoms and may have a substituent; and $Ar^2$ represents an aryl group having 6 to 60 ring carbon atoms and may have a substituent or a heterocyclic group having 5 to 60 ring atoms and may have a substituent).

(D)

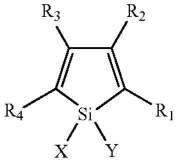

A silacyclopentadiene derivative represented by the general formula (D) (In the formula: X and Y each independently represent a saturated or unsaturated hydrocarbon group having 1 to 6-carbon atoms, an alkoxy group, an alkenyloxy group, an alkynyloxy group, a hydroxy group, a substituted or unsubstituted aryl group, or a substituted or unsubstituted heterocycle, or X and Y are bonded to each other to form a structure as a saturated or unsaturated ring; and $R_1$ to $R_4$ each independently represent hydrogen, a halogen atom, a substituted or unsubstituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, or, when two or more of $R_1$ to $R_4$ are adjacent to each other, they form a structure in which a substituted or unsubstituted ring is condensed).

(E)

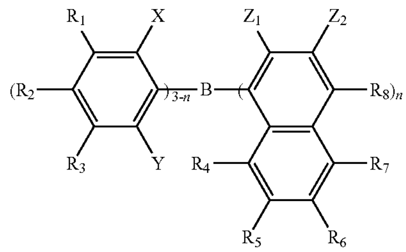

A boron derivative represented by the formula (E) (I n the formula: $R_1$ to $R_8$ and $Z_2$ each independently represent a hydrogen atom, a saturated or unsaturated hydrocarbon group, an aromatic hydrocarbon group, a heterocyclic group, a substituted amino group, a substituted boryl group, an alkoxy group, or an aryl oxy group;

X, Y, and $Z_1$ each independently represent a saturated or unsaturated hydrocarbon group, an aromatic hydrocarbon group, a heterocyclic group, a substituted amino group, an alkoxy group, or an aryloxy group;

substituents of $Z_1$ and $Z_2$ may be bonded to each other to form a fused ring; and n represents an integer of 1 to 3, and, when n represents 2 or more, $Z_1$'s may be different from each other;

provided that the case where n represents 1, X, Y, and $R_2$ each represent a methyl group, $R_8$ represents a hydrogen atom or a substituted boryl group and the case where n represents 3 and $Z_1$'s each represent a methyl group are excluded).

(F)

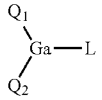

(In the formula: $Q^1$ and $Q^2$ each independently represent a ligand represented by the following general formula (G); and L represents a halogen atom, a substituted or unsubstituted alkyl group, a substituted or unsubstituted cycloalkyl group, a substituted or unsubstituted aryl group, a substituted or unsubstituted heterocyclic group, $—OR^1$ (where $R^1$ represents a hydrogen atom, a substituted or unsubstituted alkyl group, a substituted or unsubstituted cycloalkyl group, a substituted or unsubstituted aryl group, or a substituted or unsubstituted heterocyclic group), or a ligand represented by $—O—Ga-Q^3(Q^4)$ (where $Q^3$ and $Q^4$ are identical to $Q^1$ and $Q^2$, respectively).)

(G)

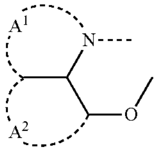

(In the formula: rings $A^1$ and $A^2$ are six-membered aryl ring structures which are condensed with each other and each of which may have a substituent.) The metal complex behaves strongly as an n-type semiconductor, and has a large electron inject ing ability. Further, generation energy upon formation of the complex is low. As a result, the metal and the ligand of the formed metal complex are bonded to each other so strongly that the fluorescent quantum efficiency of the complex as a light emitting material improves.

Specific examples of a substituent in the rings $A^1$ and $A^2$ which each form a ligand in the general formula (G) include: a halogen atom such as chlorine, bromine, iodine, or fluorine; a substituted or unsubstituted alkyl group such as a methyl group, an ethyl group, a propyl group, a butyl group, an s-butyl group, a t-butyl group, a pentyl group, a hexyl group, a heptyl group, an octyl group, a stearyl group, or trichloromethyl group; a substituted or unsubstituted aryl group such as a phenyl group, a naphthyl group, a 3-methylphenyl group, a 3-methoxyphenyl group, a 3-fluorophenyl group, a 3-trichloromethylphenyl group, a 3-trifluoromethylphenyl group, or a 3-nitrophenyl group; a substituted or unsubstituted alkoxy group such as a methoxy group, an n-butoxy group, a t-butoxy group, a trichloromethoxy group, a trifluoroethoxy group, a pentafluoropropoxy group, a 2,2,3,3-tetrafluoropropoxy group, a 1,1,1,3,3,3-hexafluoro-2-propoxy group, or a 6-(perfluoroethyl)hexyloxy group; a substituted or unsubstituted aryloxy group such as a phenoxy group, a p-nitrophenoxy group, p-t-butylphenoxy group, a 3-fluorophenoxy group, a pentafluorophenyl group, or a 3-trifluoromethylphenoxy group; a substituted or unsubstituted alkylthio group such as a methylthio group, an ethylthio group, a t-butylthio group, a hexylthio group, an octylthio group, or a trifluoromethylthio group; a substituted or unsubstituted arylthio group such as a phenylthio group, a p-nitrophenylthio group, a p-t-butylphenylthio group, a 3-fluorophenylthio group, a pentafluorophenylthio group, or a 3-trifluoromethylphenylthio group; a mono-substituted or di-substituted amino group such as a cyano group, a nitro group, an amino group, a methylamino group, a diethylamino group, an ethylamino group, a diethylamino group, a dipropylamino group, a dibutylamino group, or a diphenylamino group; an acylamino group such as a bis(acetoxymethyl)amino group, a bis(acetoxyethyl)amino group, a bisacetoxypropyl)amino group, or a bis(acetoxybutyl) amino group; a carbamoyl group such as a hydroxyl group, a siloxy group, an acyl group, a methylcarbamoyl group, a dimethylcarbamoyl group, an ethylcarbamoyl group, a diethylcarbamoyl group, a propylcarbamoyl group, a butylcarbamoyl group, or a phenylcarbamoyl group; a cycloalkyl group such as a carboxylic acid group, a sulfonic acid group, an imide group, a cyclopentane group, or a cyclohexyl group; an aryl group such as a phenyl group, a naphthyl group, a biphenyl group, an anthranyl group, a phenanthryl group, a fluorenyl group, or a pyrenyl group; and a heterocyclic group such as a pyrizinyl group, a pyrazinyl group, a pyrimidinyl group, a pyridazinyl group, a triazinyl group, an indolinyl group, a quinolinyl group, an acridinyl group, a pyrrolidinyl group, a dioxanyl group, a piperidinyl group, a morpholidinyl group, a piperazinyl group, a triathinyl group, a carbazolyl group, a furanyl group, a thiophenyl group, an oxazolyl group, an oxadiazolyl group, a benzooxazolyl group, a thiazolyl group, a thiadiazolyl group, a benzothiazolyl group, a triazolyl group, an imidazolyl group, a benzoimidazolyl group, or a puranyl group. In addition, the above-mentioned substituents may be bound to each other to further form a six-membered aryl ring or a heterocyclic ring.

At least one kind of a light emitting material, a doping material, a hole injecting material, and an electron injecting material may be present in the same layer of the organic thin film layer in the organic EL device of the present invention as the layer in which the anthracene derivative represented by any one of the general formulae of the present invention is present. Alternatively, the surface of the organic EL device obtained by the present invention can be provided with a protective layer, or the entirety of the device can be protected with, for example, a silicone oil or a resin in order that the stability of the device against a temperature, humidity, atmosphere, or the like may be improved.

A material having a work function in excess of 4 eV is a suitable conductive material to be used in the anode of the organic EL device, and examples of the material to be used include: carbon, aluminum, vanadium, iron, cobalt, nickel, tungsten, silver, gold, platinum, and palladium, and alloys of them; metal oxides for use in an ITO substrate and an NESA substrate such as tin oxide and indium oxide; and organic conductive resins such as polythiophene and polypyrrole.

A substance having a work function of less than 4 eV is a suitable conductive substance to be used in the cathode, and examples of the substance to be used include, but not limited to, magnesium, calcium, tin, lead, titanium, yttrium, lithium, ruthenium, manganese, and aluminum, and alloys of them. Representative examples of the alloys include, but not limited to, a magnesium/silver alloy, a magnesium/indium alloy, and a lithium/aluminum alloy. The compounding ratio of any such alloy is controlled depending on, for example, the temperature of a vapor deposition source, an atmosphere in which the alloy is formed, and the degree of vacuum of the atmosphere, and an appropriate ratio is selected for the alloy.

Each of the anode and the cathode may be formed of two or more layers as required. At least one surface, that is, at least one of the anode and cathode, of the organic EL device is desirably transparent in the luminous wavelength region of the device to a sufficient extent in order that the device may emit light efficiently.

In addition, the substrate of the device is also desirably transparent. A transparent electrode is set with any one of the above conductive materials by a method such as vapor deposition or sputtering in order that predetermined translucency may be secured. An electrode on the light emitting surface of the device desirably has a light transmittance of 10% or more. The substrate is not limited as long as the substrate has a mechanical strength, a thermal strength, and transparency; a glass substrate and a transparent resin film are each a desirable substrate. Examples of the transparent resin film include polyethylene, an ethylene-vinyl acetate copolymer, an ethylene-vinyl alcohol copolymer, polypropylene, polystyrene, polymethyl methacrylate, polyvinyl chloride, polyvinyl alcohol, polyvinyl butyral, nylon, polyether ether ketone, polysulphone, polyether sulphone, a tetrafluoroethylene-perfluoroalkylvinylether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyimide, polyether imide, polyimide, and polypropylene.

Any one of dry film formation methods such as vacuum vapor deposition, sputtering, plasma, and ion plating and wet film formation methods such as spin coating, dipping, and flow coating is applicable to the formation of each layer of the organic EL device according to the present invention. The thickness of each layer is not particularly limited, but must be set to an appropriate thickness. When the thickness is excessively large, a large voltage must be applied in order that a certain optical output may be obtained, with the result that the efficiency with which the optical output is obtained deteriorates. When the thickness is excessively small, a pinhole or the like is produced, so sufficient emission luminance cannot be obtained even when an electric field is applied to the device. In ordinary cases, a thickness in the range of 5 nm to 10 μm is suitable; a thickness in the range of 10 nm to 0.2 μm is more preferable. In the case of a wet film formation method, a thin film is formed by dissolving or dispersing a material of which each layer is formed in an appropriate solvent such as ethanol, chloroform, tetrahydrofuran, or dioxane; any solvent is permitted as long as the material is soluble in the solvent. In addition, an appropriate resin or additive may be used in any layer of the organic thin film layer for the purposes of, for example, improving film formability and preventing a pinhole in a film. Examples of the resin that can be used include: insulating resins such as polystyrene, polycarbonate, polyallylate, polyester, polyamide, polyurethane, polysulfone, polymethyl methacrylate, polymethyl acrylate, and cellulose, and copolymers of them; photoconductive resins such as poly-N-vinylcarbazole and polysilane; and conductive resins such as polythiophene and polypyrrole. In addition, examples of the additive include an antioxidant, a UV absorber, and a plasticizer.

The organic EL device of the present invention can be utilized in, for example, a flat light emitting body such as a flat panel display of a wall television, a light source for, for example, the backlight or meters of a copying machine, printer, or liquid crystal display, a display board, or an identification lamp.

EXAMPLES

Next, the present invention will be described in more detail by way of examples. However, the present invention is not limited to these examples.

Synthesis Example X-1

Synthesis of Compound X-1

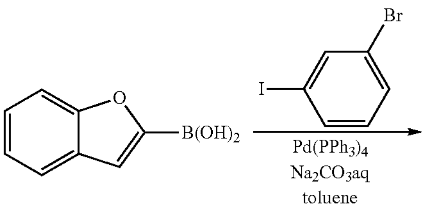

-continued

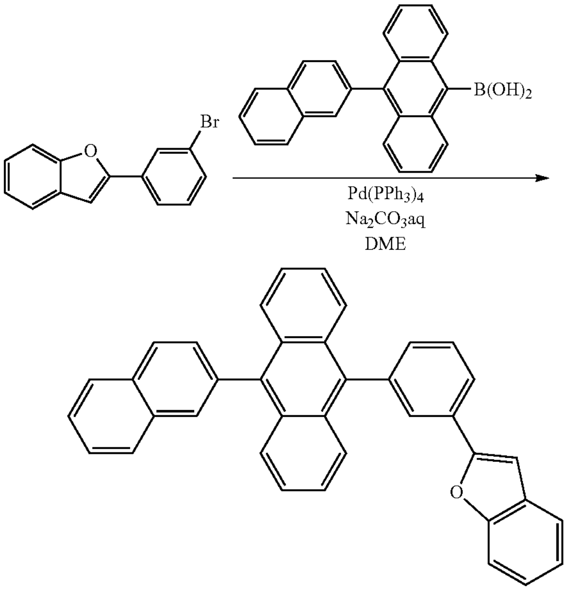

X-1

(1-1) Synthesis of 2-(3-bromophenyl)benzo[b]furan

Under an argon atmosphere, 300 mL of toluene and 150 mL of a 2-M aqueous solution of sodium carbonate were added to 28.3 g (100 mmol) of 4-iodobromobenzene, 17.0 g (105 mmol) of benzofuran-2-boronic acid, and 2.31 g (2.00 mmol) of tetrakis(triphenylphosphine)palladium(0), and the mixture was refluxed under heat for 10 hours.

Immediately after the completion of the reaction, the resultant was filtrated, and then the water layer was removed. The organic layer was dried with sodium sulfate, and was then concentrated. The residue was purified by silica gel column chromatography, whereby 22.1 g of the white crystal of 2-(3-bromophenyl)benzo[b]furan were obtained (81% yield).

(1-2) Synthesis of Compound X-1

Under an argon atmosphere, 30 mL of dimethoxyethane (DME) and 15 mL of a 2-M aqueous solution of sodium carbonate were added to 2.73 g (10.0 mmol) of 2-(3-bromophenyl)benzo[b]furan, 3.83 g (11.0 mmol) of 10-(2-naphthyl)anthracene-9-boronic acid, 0.231 g (0.200 mmol) of tetrakis(triphenylphosphine)palladium(0), and the mixture was refluxed under heat for 10 hours. After the completion of the reaction, the resultant was cooled to room temperature. The precipitated solid was taken by filtration, washed with methanol, water, and methanol in the stated order, and dried under reduced pressure. The resultant solid was recrystallized with toluene, whereby 4.20 g of a pale yellow crystal were obtained. Mass spectral analysis confirmed the following: the crystal was the target product and had an m/e of 496, which was indicative of the molecular weight of the target product, i.e., 496.18.

Synthesis Example X-2

Synthesis of Compound X-2

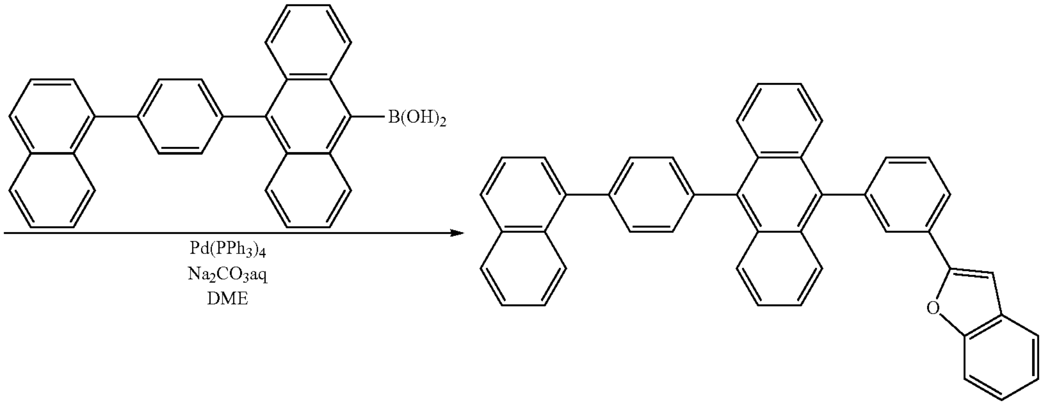

X-2

Compound X-2 was synthesized in the same manner as in Synthesis Example X-1 except that 10-[4-(1-naphthyl)phenyl]anthracene-9-boronic acid was used instead of 10-(2-naphthyl)anthracene-9-boronic acid. Mass spectral analysis confirmed the following: the product was the target product and had an m/e of 572, which was indicative of the molecular weight of the target product, i.e., 572.21.

Synthesis Example X-3

Synthesis of Compound X-3

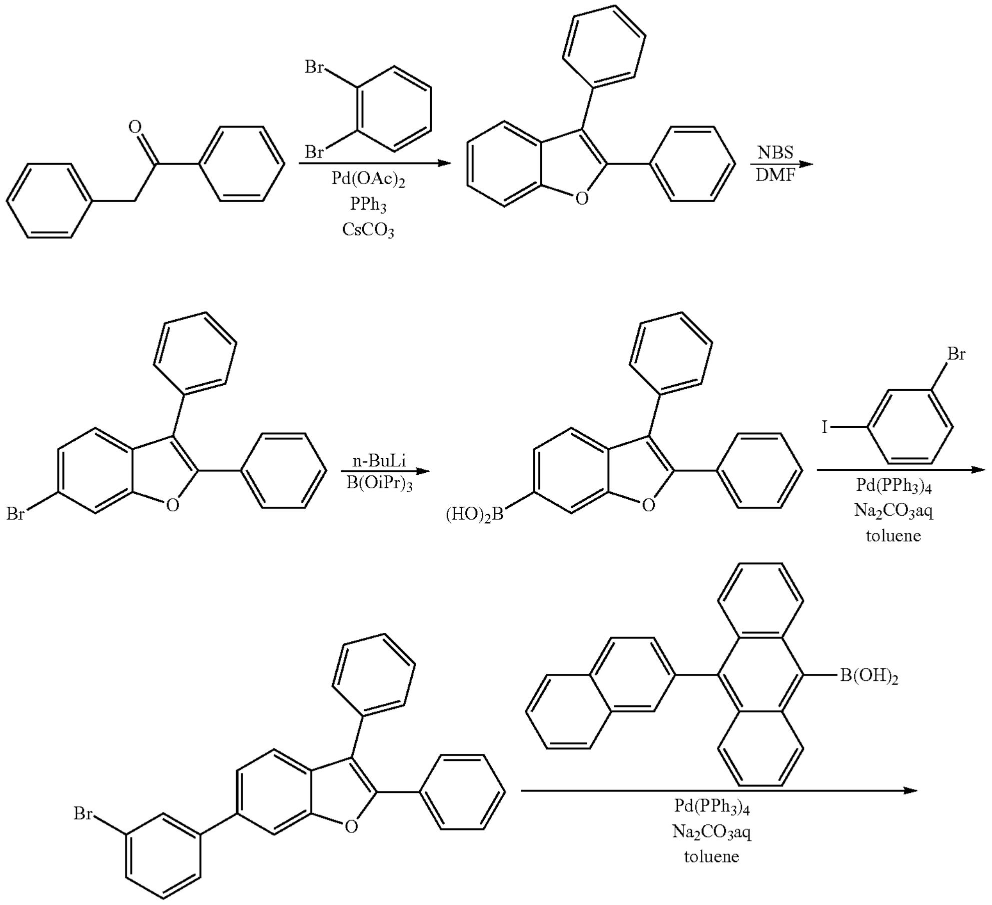

-continued

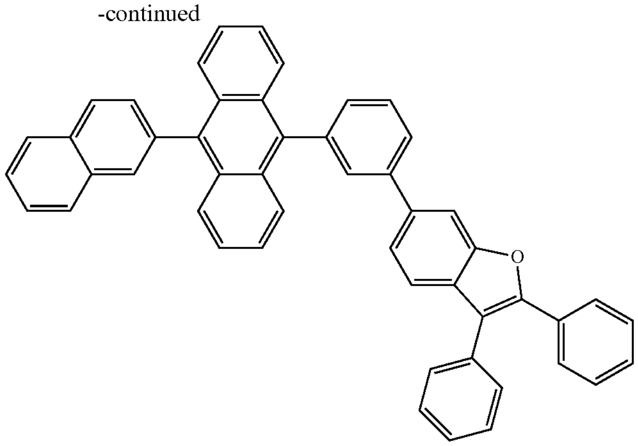

X-3

(3-1) Synthesis of 2,3-diphenylbenzo[b]furan 39.2 g of benzyl phenyl ketone, 46.7 g of 1,2-dibromobenzene, 2.24 g of palladium acetate, 10.5 g of triphenylphosphine, 77.2 g of cesium carbonate, and 900 mL of o-xylene were loaded into a flask, and the mixture was refluxed and stirred under heat under an argon atmosphere for 8 hours. After the completion of the reaction, the reaction solution was filtrated while being extracted with ether. The filtrate was dried with magnesium sulfate, and was then concentrated. The residue was purified by silica gel column chromatography, whereby 43.2 g of a white crystal were obtained (80% yield).

(3-2) Synthesis of 6-bromo-2,3-diphenylbenzo[b]furan 43.2 g of 2,3-diphenylbenzo[b]furan, 31.3 g of N-bromosuccinimide, and 400 mL of N, N-dimethylformamide were loaded into a flask, and the mixture was stirred under heat at 70° C. for 8 hours. After having been cooled to room temperature, the reaction solution was poured into 2 L of water. The precipitated crystal was separated by filtration, washed with methanol, water, and methanol in the stated order, and purified by silica gel column chromatography, whereby 40.2 g of a pale yellow crystal were obtained (72% yield).

(3-3) Synthesis of 2,3-diphenylbenzo[b]furan-6-boronic acid

Under an argon atmosphere, 400 mL of anhydrous THF were added to 40.2 g of 6-bromo-2,3-diphenylbenzo[b]furan, and the mixture was stirred at −40° C. During the stirring, 72 mL of a 1.6-M solution of n-butyllithium in hexane were added to the mixture. The reaction solution was stirred for 1 hour while being heated to 0° C. The reaction solution was cooled to −78° C. again, and a solution of 59.0 g (250 mmol) of trimethyl borate in 50 mL of dry THF was dropped to the solution. The reaction solution was stirred at room temperature for 5 hours. 200 mL of 1N hydrochloric acid were added to the reaction solution, and the mixture was stirred for 1 hour. After that, the water layer was removed. The organic layer was dried with magnesium sulfate, and the solvent was removed by distillation under reduced pressure. The resultant solid was washed with toluene, whereby 21.7 g of 2,3-diphenylbenzo[b]furan-6-boronic acid were obtained (60% yield).

(3-4) Synthesis of 6-(3-bromophenyl)-2,3-diphenylbenzo[b]furan

Under an argon atmosphere, 220 mL of toluene and 110 mL of a 2-M aqueous solution of sodium carbonate were added to 19.6 g of 4-iodobromobenzene, 21.7 g of dibenzofuran-4-boronic acid, and 1.59 g (2.00 mmol) of tetrakis (triphenylphosphine)palladium(0), and the mixture was refluxed under heat for 10 hours.

Immediately after the completion of the reaction, the resultant was filtrated, and then the water layer was removed. The organic layer was dried with sodium sulfate, and was then concentrated. The residue was purified by silica gel column chromatography, whereby 23.5 g of the white crystal of 6-(3-bromophenyl)-2,3-diphenylbenzo[b]furan were obtained (80% yield).

(3-5) Synthesis of Compound X-3

Compound X-3 was synthesized in the same manner as in Synthesis Example X-1 except that 6-(3-bromophenyl)-2,3-diphenylbenzo[b]furan was used instead of 2-(3-bromophenyl)benzo[b]furan. Mass spectral analysis confirmed the following: the product was the target product and had an m/e of 648, which was indicative of the molecular weight of the target product, i.e., 648.25.

Synthesis Example X-4

Synthesis of Compound X-4

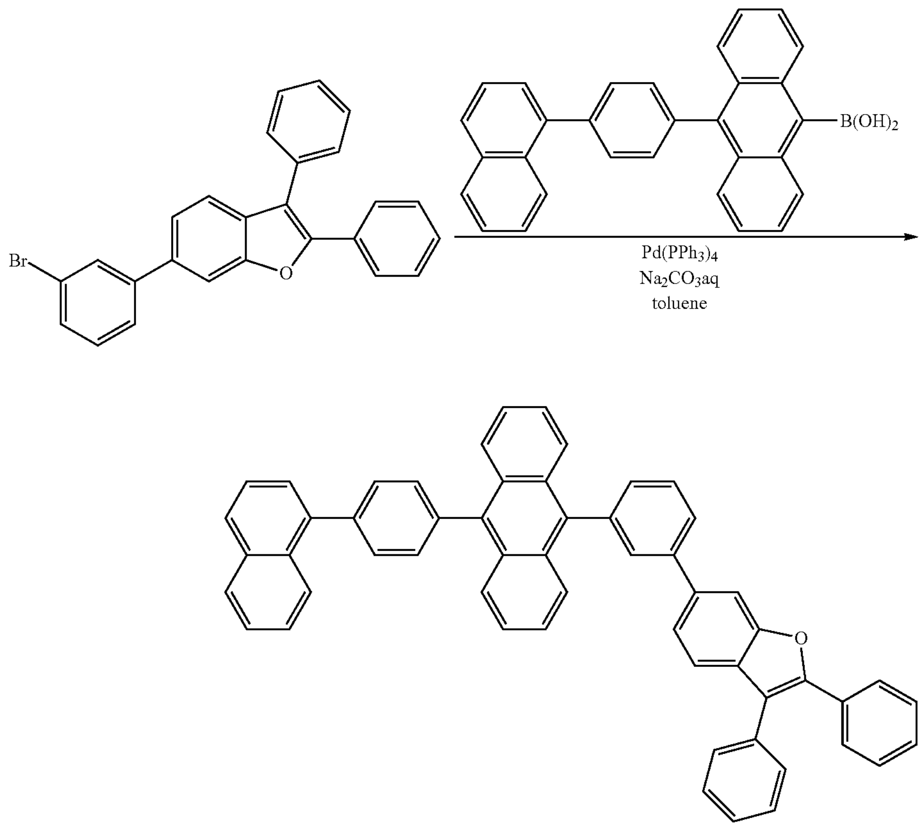

X-4

Compound X-4 was synthesized in the same manner as in Synthesis Example X-1 except that: 6-(3-bromophenyl)-2,3-diphenylbenzo[b]furan was used instead of 2-(3-bromophenyl)benzo[b]furan; and 10-[4-(1-naphthyl)phenyl]anthracene-9-boronic acid was used instead of 10-(2-naphthyl) anthracene-9-boronic acid. Mass spectral analysis confirmed the following: the product was the target product and had an m/e of 724, which was indicative of the molecular weight of the target product, i.e., 724.28.

Example 1

A glass substrate measuring 25 mm wide by 75 mm long by 1.1 mm thick and provided with an ITO transparent electrode (anode) (manufactured by GEOMATEC Co., Ltd.) was subjected to ultrasonic cleaning in isopropyl alcohol for 5 minutes, and was then subjected to UV/ozone cleaning for 30 minutes. The glass substrate with the transparent electrode line after the cleaning was mounted on a substrate holder of a vacuum vapor deposition apparatus. First, Compound A-1 shown below was formed into a film having a thickness of 60 nm on the surface on the side where the transparent electrode line was formed so as to cover the transparent electrode. Subsequently, Compound A-2 shown below was formed into a film having a thickness of 20 nm on the A-1 film.

Further, Compound X-1 shown above of the present invention and Styrylamine Derivative D-1 shown below were formed into a film having a thickness of 40 nm at a thickness ratio of 40:2 on the A-2 film, whereby a bluish light emitting layer was obtained. Compound X-1 functions as a host while Styrylamine Derivative D-1 functions as a dopant.

Alq having the following structure was formed into a film having a thickness of 20 nm by vapor deposition on the film so as to serve as an electron transporting layer. After that, LiF was formed into a film having a thickness of 1 nm. Metal aluminum was deposited from the vapor onto the LiF film so that a metal cathode having a thickness of 150 nm was formed. Thus, an organic EL device was formed.

The device performance of the resultant organic EL device when the device was driven at a current density of 10 $mA/cm^2$, and a lifetime required for an initial luminance of 1,000 $cd/m^2$ to reduce in half were measured. Table 1 shows the results.

Examples 2 to 4 and Comparative Examples 1 to 8

In each of the examples and the comparative examples, the measurement was performed in the same manner as in Example 1 except that a compound shown in Table 1 was used instead of Compound X-1 in Example 1. Table 1 shows the results.

D-1
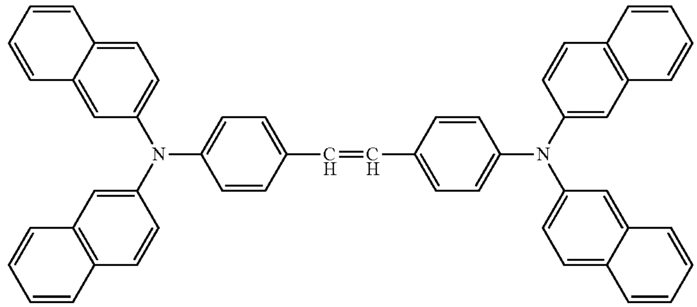
Alq
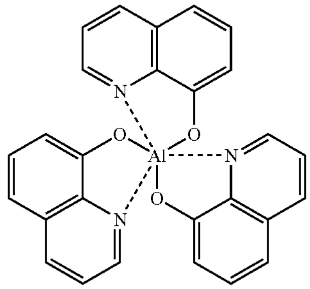
A-1
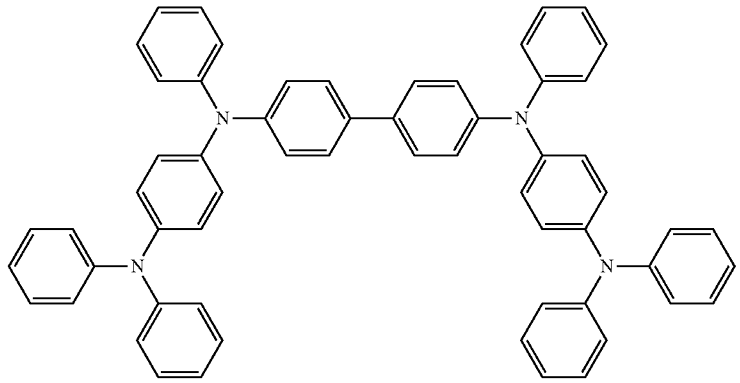
A-2
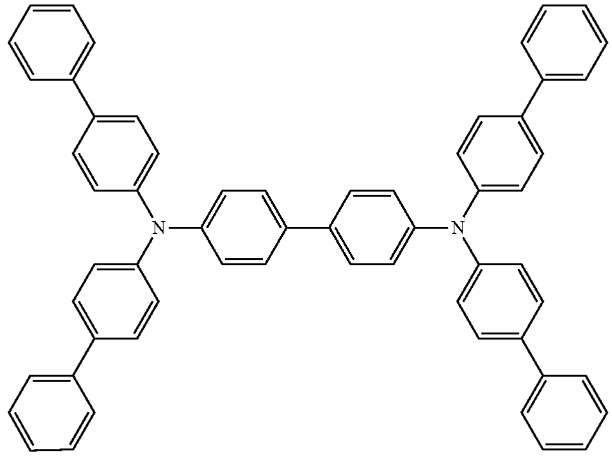

-continued
A
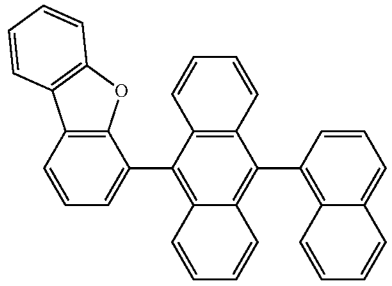
B
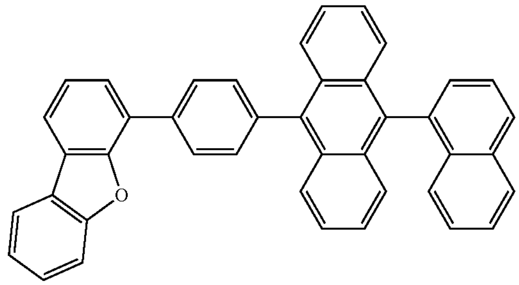
C
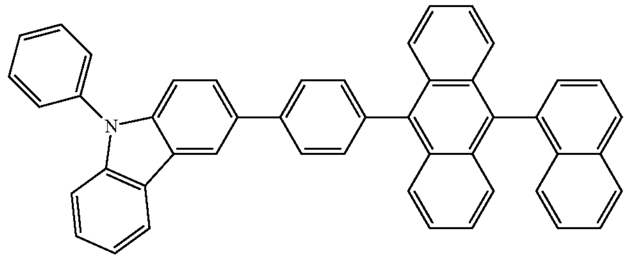
D
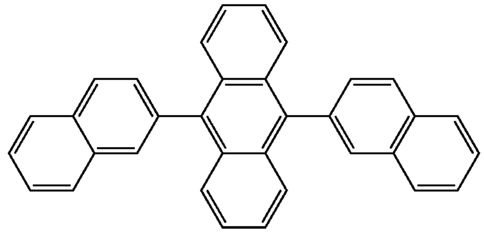
E
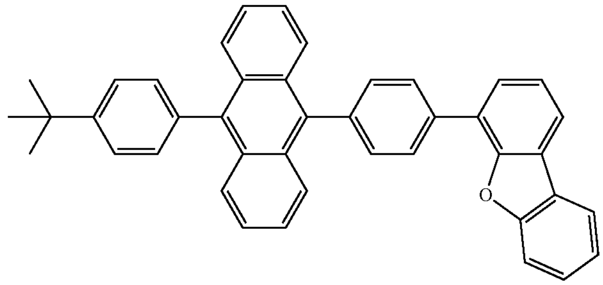
F
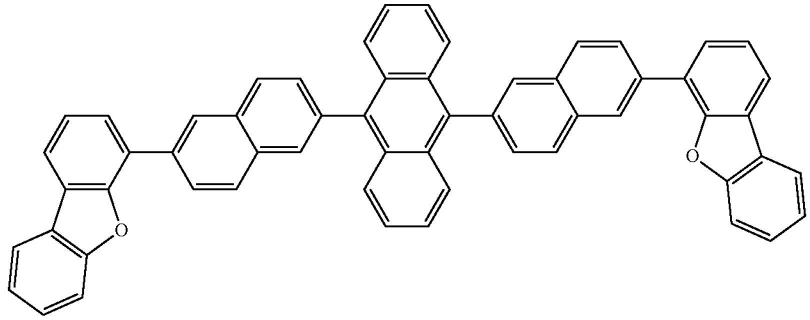

-continued

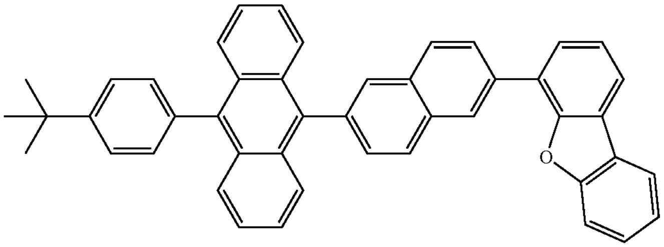

G

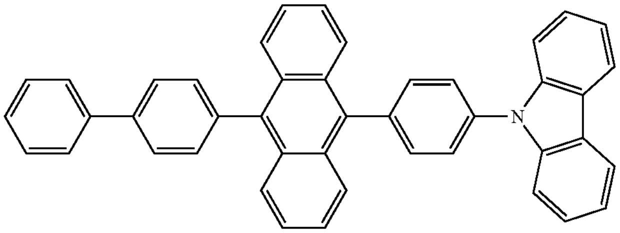

H

TABLE 1

| | Host | Dopant | Voltage (V) | Current efficiency (cd/A) | Luminescent color | Lifetime |
|---|---|---|---|---|---|---|
| Example 1 | Compound X-1 | D-1 | 6.6 | 7.2 | Blue | 7,000 |
| Example 2 | Compound X-2 | D-1 | 6.6 | 7.2 | Blue | 7,000 |
| Example 3 | Compound X-3 | D-1 | 6.5 | 7.3 | Blue | 8,000 |
| Example 4 | Compound X-4 | D-1 | 6.5 | 7.3 | Blue | 8,000 |
| Comparative Example 1 | Compound A | D-1 | 6.6 | 6.5 | Blue | 4,000 |
| Comparative Example 2 | Compound B | D-1 | 6.7 | 6.6 | Blue | 5,000 |
| Comparative Example 3 | Compound C | D-1 | 7.0 | 5.5 | Bluish green | 500 |
| Comparative Example 4 | Compound D | D-1 | 7.3 | 6.0 | Blue | 4,000 |
| Comparative Example 5 | Compound E | D-1 | 7.3 | 6.0 | Blue | 2,000 |
| Comparative Example 6 | Compound F | D-1 | 7.3 | 6.0 | Blue | 2,000 |
| Comparative Example 7 | Compound G | D-1 | 7.3 | 6.0 | Blue | 2,000 |
| Comparative Example 8 | Compound H | D-1 | 7.3 | 6.0 | Blue | 1,000 |

[Synthesis Scheme]

Intermediates to be used in Examples-of-Synthesis were produced on the basis of Synthesis Schemes (A-1) to (A-4) and Production Examples 1 to 6.

[Synthesis Scheme (A-1)] Synthesis of Anthracene Boronic Acid Derivative

An anthracene boronic acid derivative was synthesized in accordance with the following scheme by a known method.

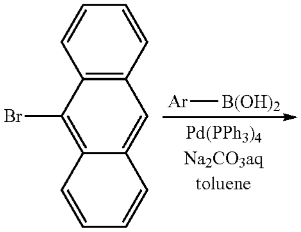

-continued

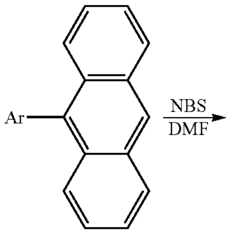

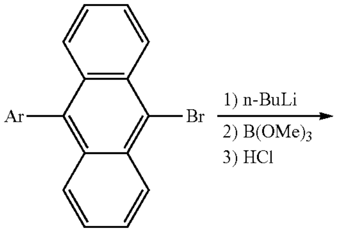

-continued

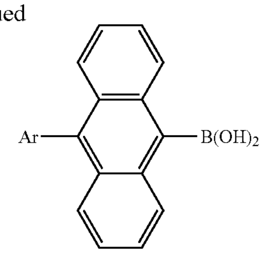

It should be noted that Ar represents $R_9$ or $R_{10}$ in the general formula (1), Ph represents a phenyl group, NBS represents N-bromosuccinimide, DMF represents dimethylformamide, and Me represents a methyl group. The same holds true for the following.

[Synthesis Scheme (A-2)] Synthesis of 4-(bromophenyl)dibenzofuran

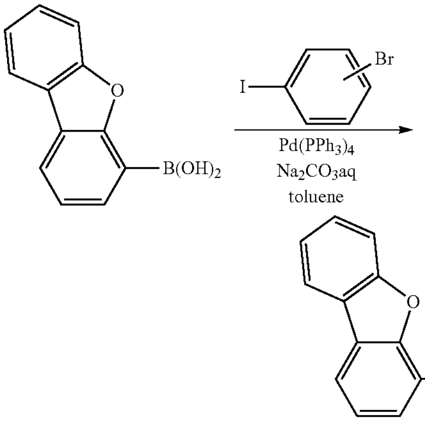

Production Example 1

Synthesis of 4-(4-bromophenyl)dibenzofuran

Under an argon atmosphere, 300 mL of toluene and 150 mL of a 2-M aqueous solution of sodium carbonate were added to 28.3 g (100 mmol) of 4-iodobromobenzene, 22.3 g (105 mmol) of dibenzofuran-4-boronic acid, and 2.31 g (2.00 mmol) of tetrakis(triphenylphosphine)palladium(0), and the mixture was refluxed under heat for 10 hours.

Immediately after the completion of the reaction, the resultant was filtrated, and then the water layer was removed. The organic layer was dried with sodium sulfate, and was then concentrated. The residue was purified by silica gel column chromatography, whereby 26.2 g of the white crystal of 4-(4-bromophenyl)dibenzofuran were obtained (81% yield).

Production Example 2

Synthesis of 4-(3-bromophenyl)dibenzofuran

Under an argon atmosphere, 300 mL of toluene and 150 mL of a 2-M aqueous solution of sodium carbonate were added to 28.3 g (100 mmol) of 3-iodobromobenzene, 22.3 g (105 mmol) of dibenzofuran-4-boronic acid, and 2.31 g (2.00 mmol) of tetrakis(triphenylphosphine)palladium(0), and the mixture was refluxed under heat for 10 hours.

Immediately after the completion of the reaction, the resultant was filtrated, and then the water layer was removed. The organic layer was dried with sodium sulfate, and was then concentrated. The residue was purified by silica gel column chromatography, whereby 24.2 g of the white crystal of 4-(3-bromophenyl)dibenzofuran were obtained (75% yield).

[Synthesis Scheme (A-3)] Synthesis of 2-(bromophenyl)dibenzofuran

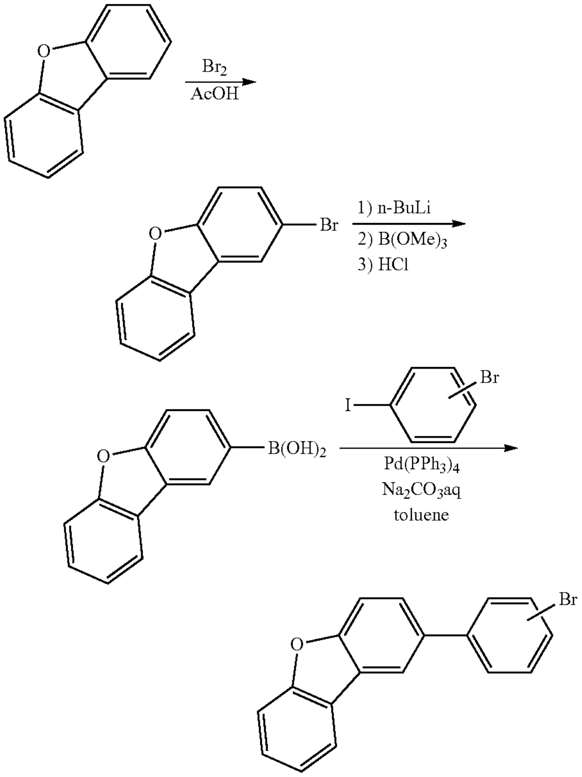

Production Example 3

Synthesis of dibenzofuran-2-boronic acid (i) Synthesis of 2-bromodibenzofuran 150 g (892 mmol) of dibenzofuran and 1 L of acetic acid were loaded into a flask. Air in the flask was replaced with nitrogen, and dibenzofuran was dissolved in acetic acid under heat. 188 g (1.18 mol) of bromine were dropped to the solution while the solution was sometimes cooled with water. After that, the mixture was stirred for 20 hours while being cooled with air. The precipitated crystal was separated by filtration, washed with acetic acid and water in the stated order, and dried under reduced pressure. The resultant crystal was purified by distillation under reduced pressure. After that, the resultant was repeatedly recrystallized with methanol several times, whereby 66.8 g of 2-bromodibenzofuran were obtained (31% yield).

(ii) Synthesis of dibenzofuran-2-boronic acid

Under an argon atmosphere, 400 mL of anhydrous tetrahydrofuran (THF) were added to 24.7 g (100 mmol) of 2-bromodibenzofuran, and the mixture was stirred at −40° C. During the stirring, 63 mL (100 mmol) of a 1.6-M solution of n-butyllithium in hexane were added to the mixture. The reaction solution was stirred for 1 hour while being heated to 0° C. The reaction solution was cooled to −78° C. again, and a solution of 26.0 g (250 mmol) of trimethyl borate in 50 mL of dry THF was dropped to the solution. The reaction solution was stirred at room temperature for 5 hours. 200 mL of 1 N hydrochloric acid were added to the reaction solution, and the mixture was stirred for 1 hour. After that, the water layer was removed. The organic layer was dried with magnesium sulfate, and the solvent was removed by distillation under reduced pressure. The resultant solid was washed with toluene, whereby 15.2 g of dibenzofuran-2-boronic acid were obtained (72% yield).

Production Example 4

Synthesis of 2-(4-bromophenyl)dibenzofuran 2-(4-bromophenyl)dibenzofuran was synthesized by using dibenzofuran-2-boronic acid instead of dibenzofuran-4-boronic acid in Production Example 1.

Production Example 5

Synthesis of 2-(3-bromophenyl)dibenzofuran 2-(3-bromophenyl)dibenzofuran was synthesized by using dibenzofuran-2-boronic acid instead of dibenzofuran-4-boronic acid in Production Example 2.

[Synthesis Scheme (A-4)] Synthesis of 4-(bromophenyl)dibenzothiophene

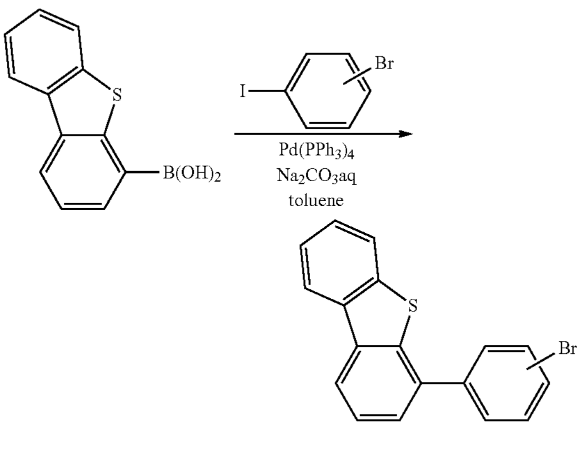

Production Example 6

Synthesis of 4-(4-bromophenyl)dibenzothiophene 4-(4-bromophenyl)dibenzothiophene was synthesized by using dibenzothiophene-4-boronic acid instead of dibenzofuran-4-boronic acid in Production Example 1.

Production Example 7

Synthesis of 4-(3-bromophenyl)dibenzothiophene 4-(3-bromophenyl)dibenzothiophene was synthesized by using dibenzothiophene-4-boronic acid instead of dibenzofuran-4-boronic acid in Production Example 2.

Example-of-Synthesis 1

Synthesis of Compound 1

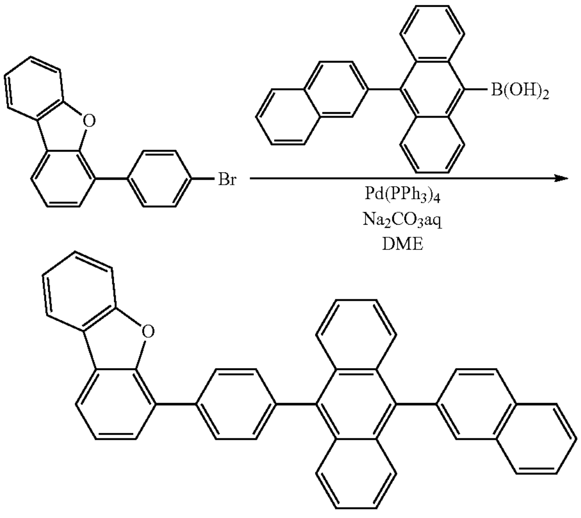

1

Under an argon atmosphere, 30 mL of dimethoxyethane (DME) and 15 mL of a 2-M aqueous solution of sodium carbonate were added to 3.22 g (10.0 mmol) of 4-(4-bromophenyl)dibenzofuran, 3.83 g (11.0 mmol) of 10-(2-naphthyl)anthracene-9-boronic acid, and 0.231 g (0.200 mmol) of tetrakis(triphenylphosphine)palladium(0), and the mixture was refluxed under heat for 10 hours. After the completion of the reaction, the resultant was cooled to room temperature. The precipitated solid was taken by filtration, washed with methanol, water, and methanol in the stated order, and dried under reduced pressure. The resultant solid was recrystallized with toluene, whereby 4.20 g of a pale yellow crystal were obtained. Mass spectral analysis confirmed the following: the crystal was the target product and had an m/e of 546, which was indicative of the molecular weight of the target product, i.e., 546.20.

Example-of-Synthesis 2

Synthesis of Compound 2

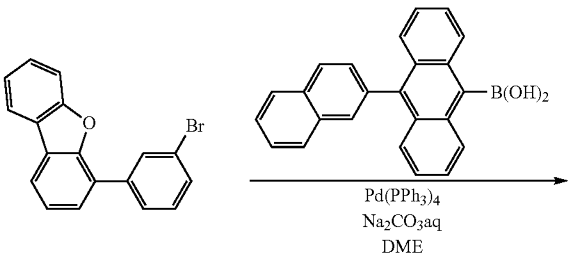

-continued

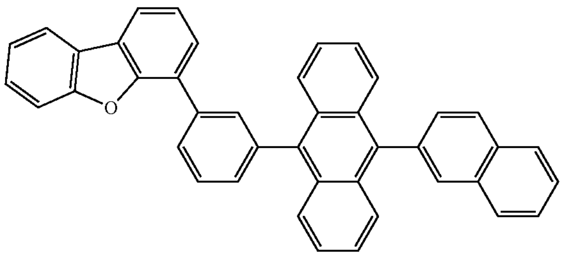

2

Compound 2 was synthesized in the same manner as in Example-of-Synthesis 1 except that 4-(3-bromophenyl) dibenzofuran was used instead of 4-(4-bromophenyl)dibenzofuran. Mass spectral analysis confirmed the following: the product was the target product and had an m/e of 546, which was indicative of the molecular weight of the target product, i.e., 546.20.

Example-of-Synthesis 3

Synthesis of Compound 3

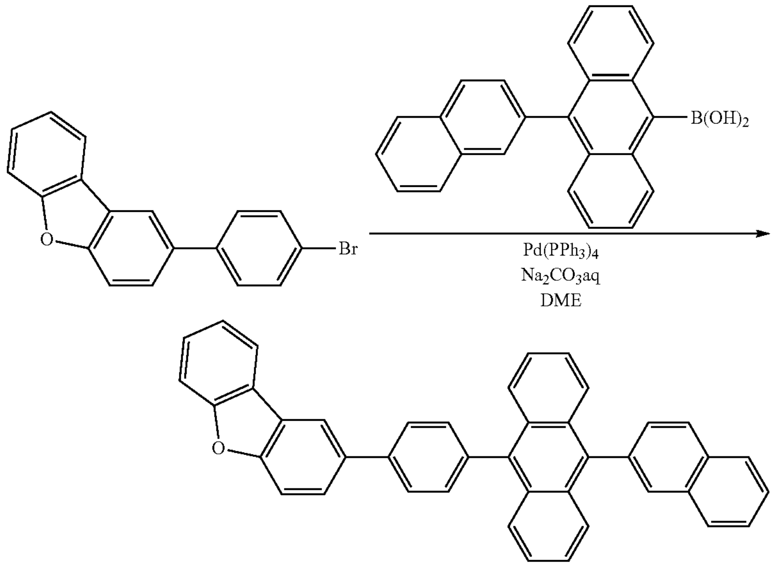

3

Compound 3 was synthesized in the same manner as in Example-of-Synthesis 1 except that 2-(4-bromophenyl) dibenzofuran was used instead of 4-(4-bromophenyl)dibenzofuran. Mass spectral analysis confirmed the following: the product was the target product and had an m/e of 546, which was indicative of the molecular weight of the target product, i.e., 546.20.

Example-of-Synthesis 4

Synthesis of Compound 4

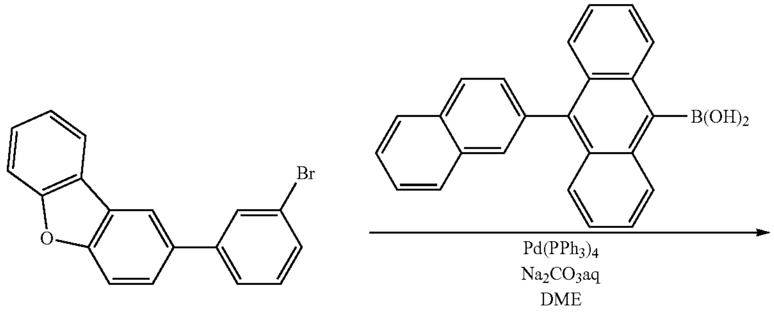

-continued

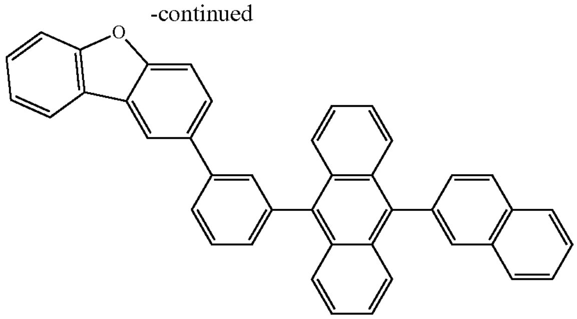

4

Compound 4 was synthesized in the same manner as in Example-of-Synthesis 1 except that 2-(3-bromophenyl)dibenzofuran was used instead of 4-(4-bromophenyl)dibenzofuran. Mass spectral analysis confirmed the following: the product was the target product and had an m/e of 546, which was indicative of the molecular weight of the target product, i.e., 546.20.

Example-of-Synthesis 5

Synthesis of Compound 5

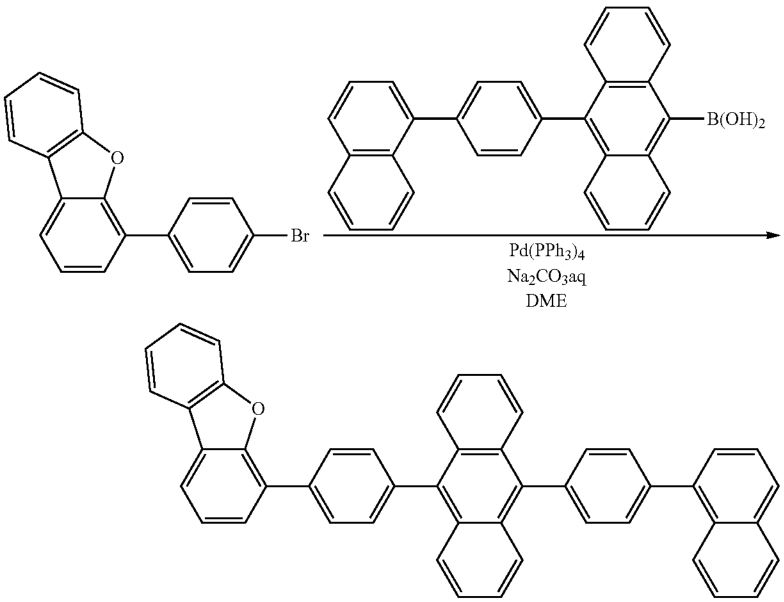

5

Compound 5 was synthesized in the same manner as in Example-of-Synthesis 1 except that 10-[4-(1-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 6

Synthesis of Compound 6

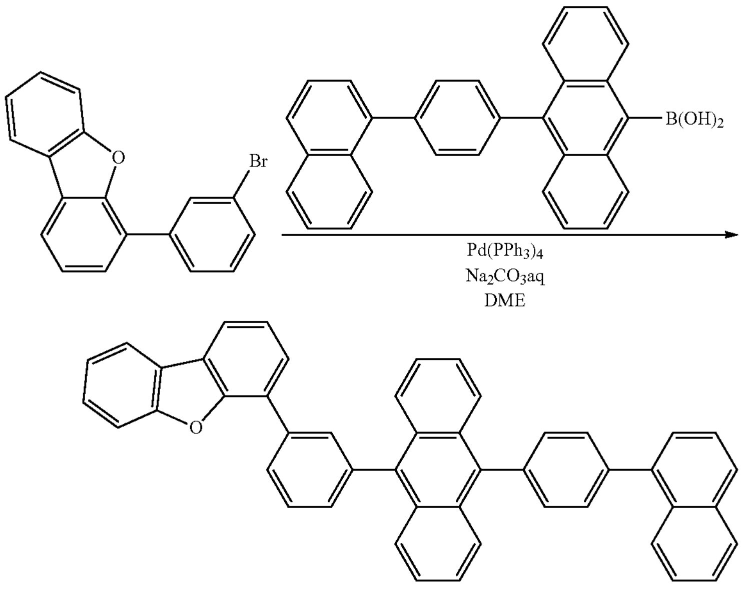

6

Compound 6 was synthesized in the same manner as in Example-of-Synthesis 1 except that: 4-(3-bromophenyl) dibenzofuran was used instead of 4-(4-bromophenyl)dibenzofuran; and 10-[4-(1-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 7

Synthesis of Compound 7

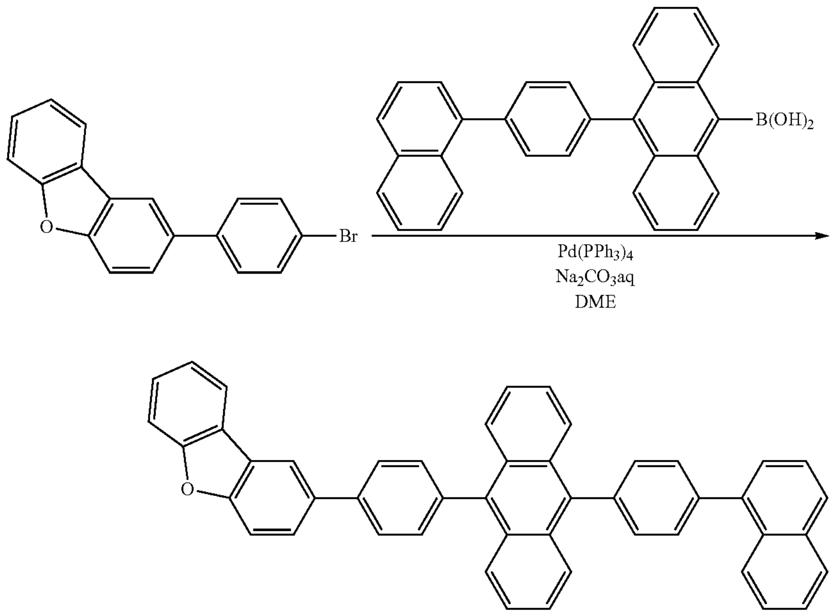

7

Compound 7 was synthesized in the same manner as in Example-of-Synthesis 1 except that: 2-(4-bromophenyl)dibenzofuran was used instead of 4-(4-bromophenyl)dibenzofuran; and 10-[4-(1-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 8

Synthesis of Compound 8

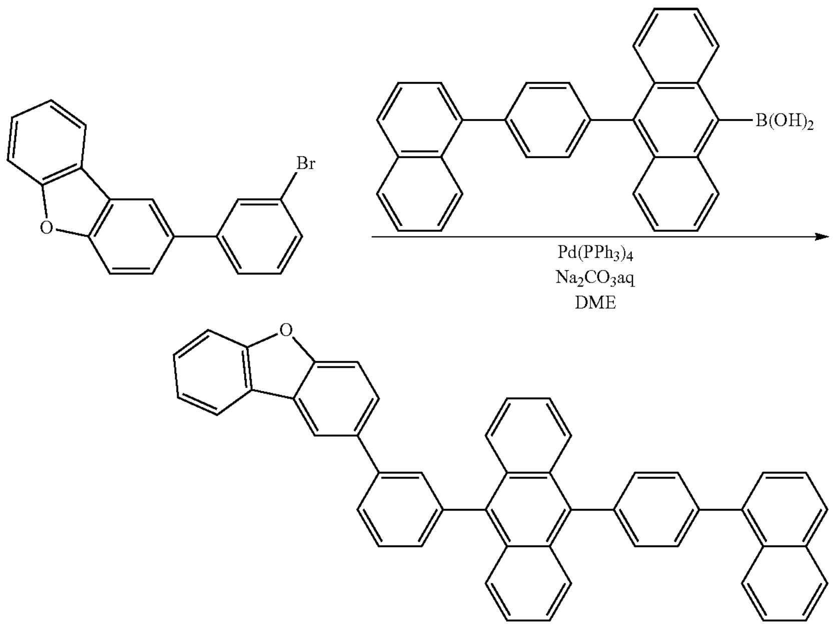

8

Compound 8 was synthesized in the same manner as in Example-of-Synthesis 1 except that: 2-(3-bromophenyl)dibenzofuran was used instead of 4-(4-bromophenyl)dibenzofuran; and 10-[4-(1-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 9

Synthesis of Compound 9

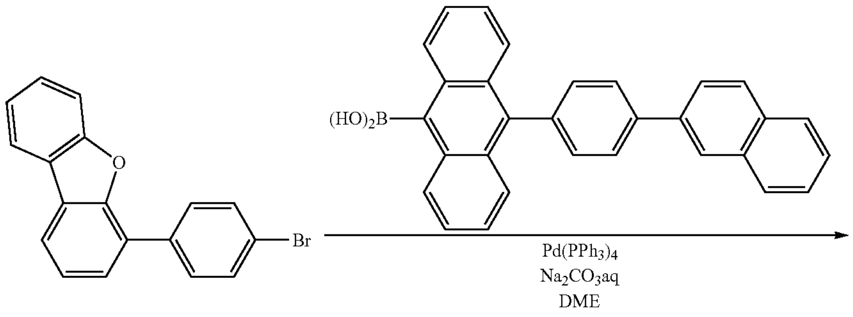

-continued

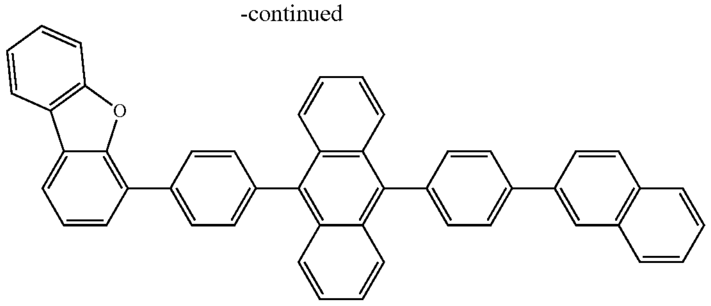

9

Compound 9 was synthesized in the same manner as in Example-of-Synthesis 1 except that 10-[4-(2-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 10

Synthesis of Compound 10

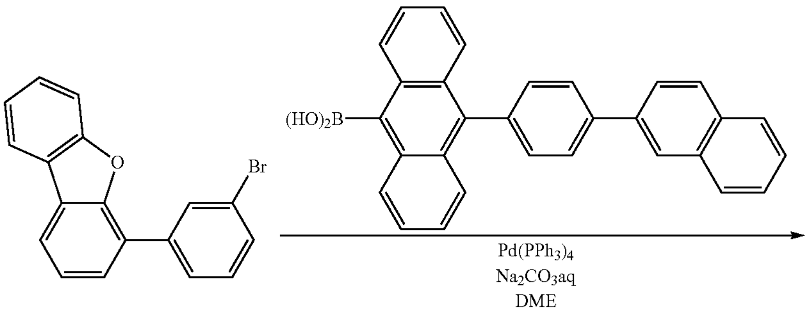

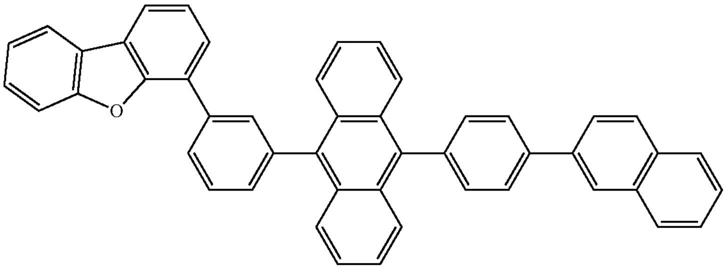

10

Compound 10 was synthesized in the same manner as in Example-of-Synthesis 1 except that: 4-(3-bromophenyl) dibenzofuran was used instead of 4-(4-bromophenyl)dibenzofuran; and 10-[4-(2-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 11

Synthesis of Compound 11

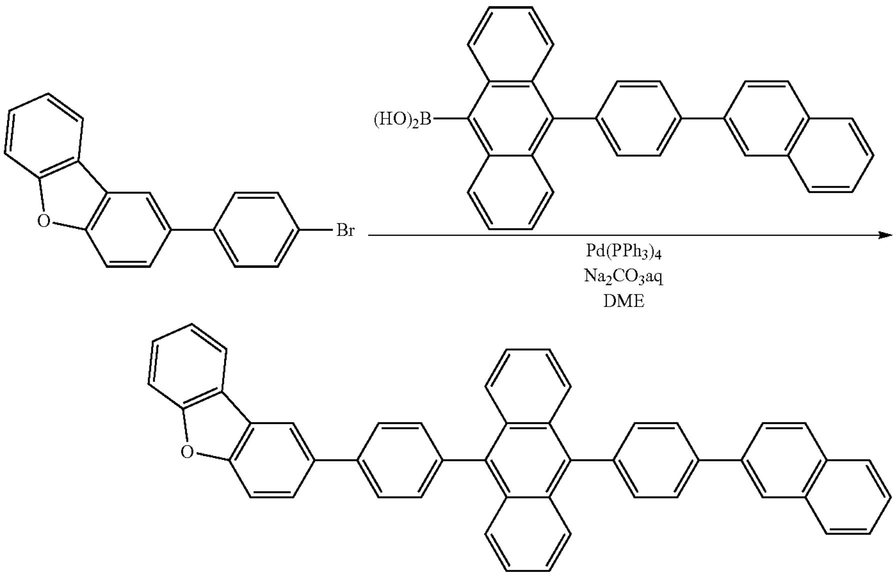

11

Compound 11 was synthesized in the same manner as in Example-of-Synthesis 1 except that: 2-(4-bromophenyl)dibenzofuran was used instead of 4-(4-bromophenyl)dibenzofuran; and 10-[4-(2-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 12

Synthesis of Compound 12

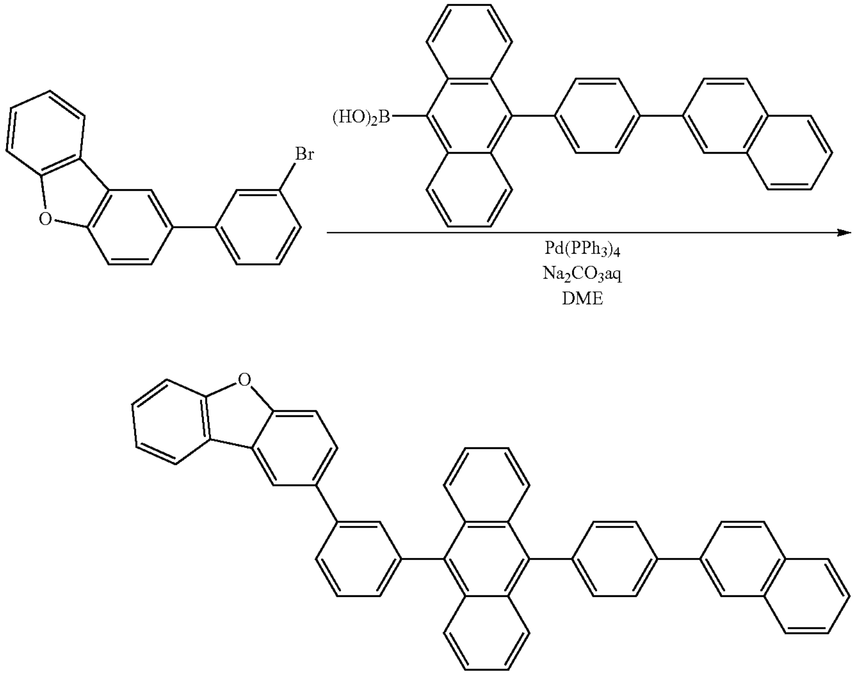

12

Compound 12 was synthesized in the same manner as in Example-of-Synthesis 1 except that: 2-(3-bromophenyl) dibenzofuran was used instead of 4-(4-bromophenyl)dibenzofuran; and 10-[4-(2-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 13

Synthesis of Compound 13

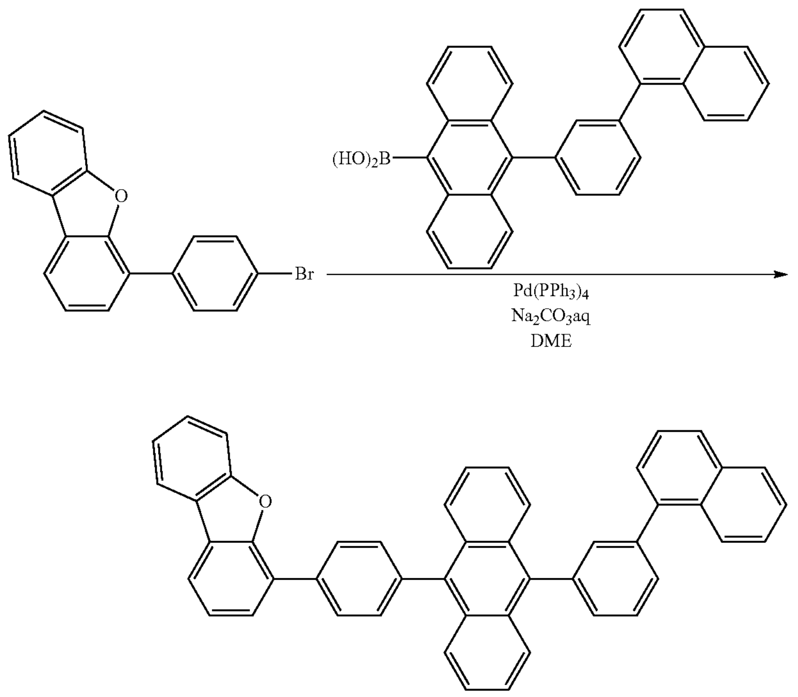

13

Compound 13 was synthesized in the same manner as in Example-of-Synthesis 1 except that 10-[3-(1-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 14

Synthesis of Compound 14

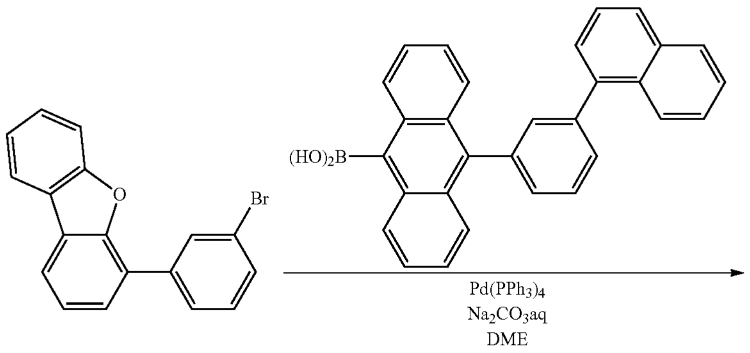

-continued

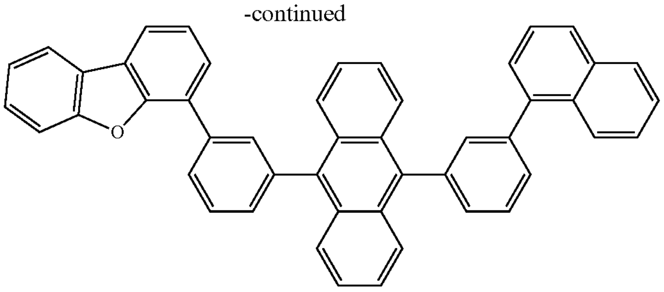

14

Compound 14 was synthesized in the same manner as in Example-of-Synthesis 1 except that: 4-(3-bromophenyl) dibenzofuran was used instead of 4-(4-bromophenyl)dibenzofuran; and 10-[3-(1-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 15

Synthesis of Compound 15

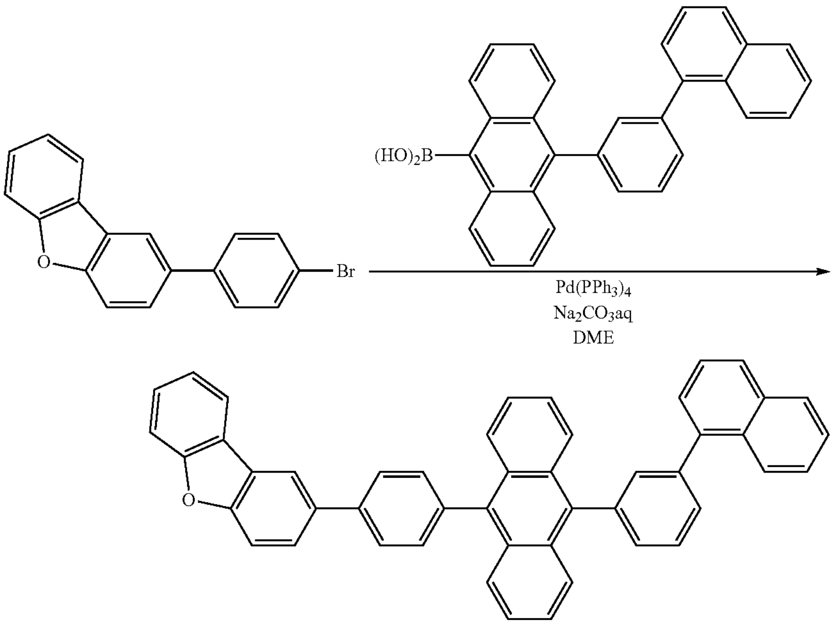

15

Compound 15 was synthesized in the same manner as in Example-of-Synthesis 1 except that: 2-(4-bromophenyl) dibenzofuran was used instead of 4-(4-bromophenyl)dibenzofuran; and 10-[3-(1-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 16

Synthesis of Compound 16

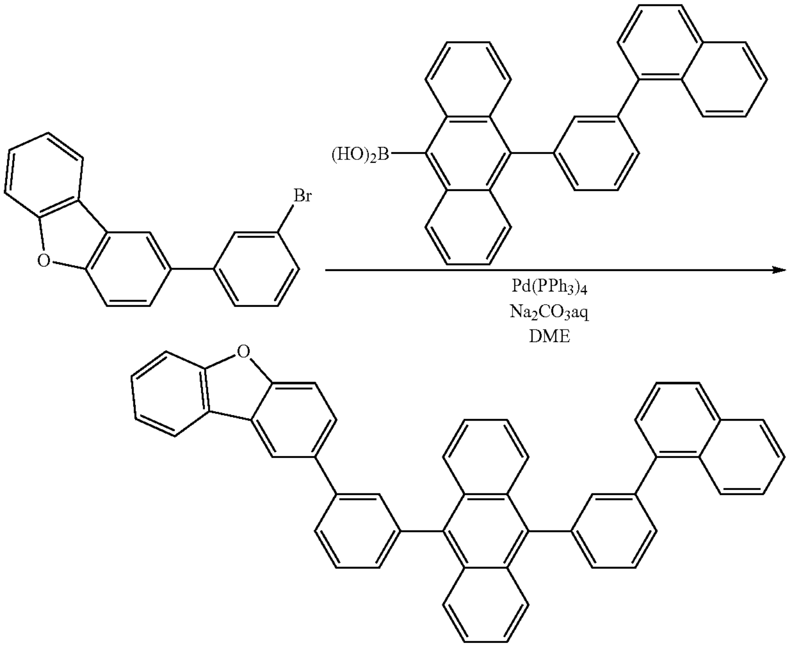

16

Compound 16 was synthesized in the same manner as in Example-of-Synthesis 1 except that: 2-(3-bromophenyl) dibenzofuran was used instead of 4-(4-bromophenyl)dibenzofuran; and 10-[3-(1-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 17

Synthesis of Compound 17

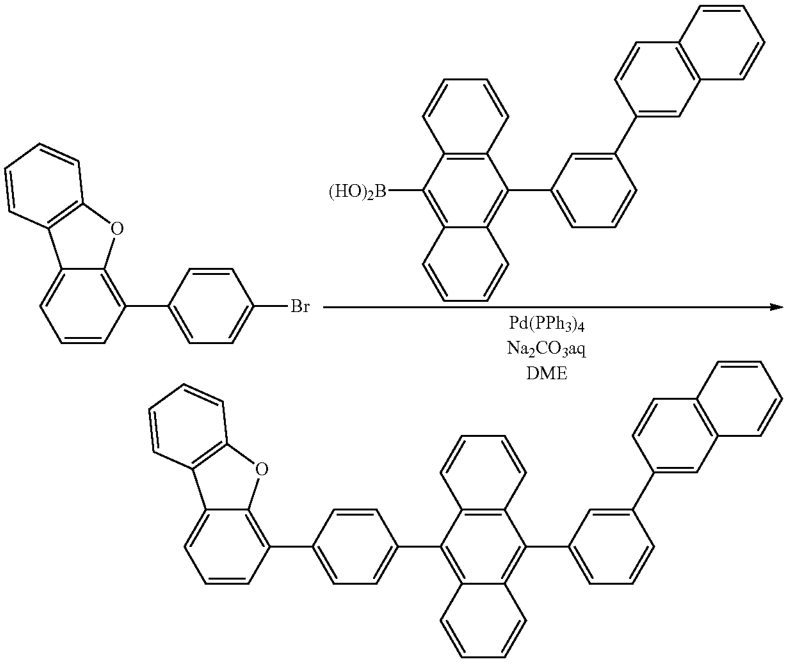

17

Compound 17 was synthesized in the same manner as in Example-of-Synthesis 1 except that 10-[3-(2-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 18

Synthesis of Compound 18

Compound 18 was synthesized in the same manner as in Example-of-Synthesis 1 except that: 4-(3-bromophenyl)dibenzofuran was used instead of 4-(4-bromophenyl)dibenzofuran; and 10-[3-(2-naphthyl)phenyl]anthracene-9-boronic acid was used instead of 10-(2-naphthyl)anthracene-9-boronic acid.

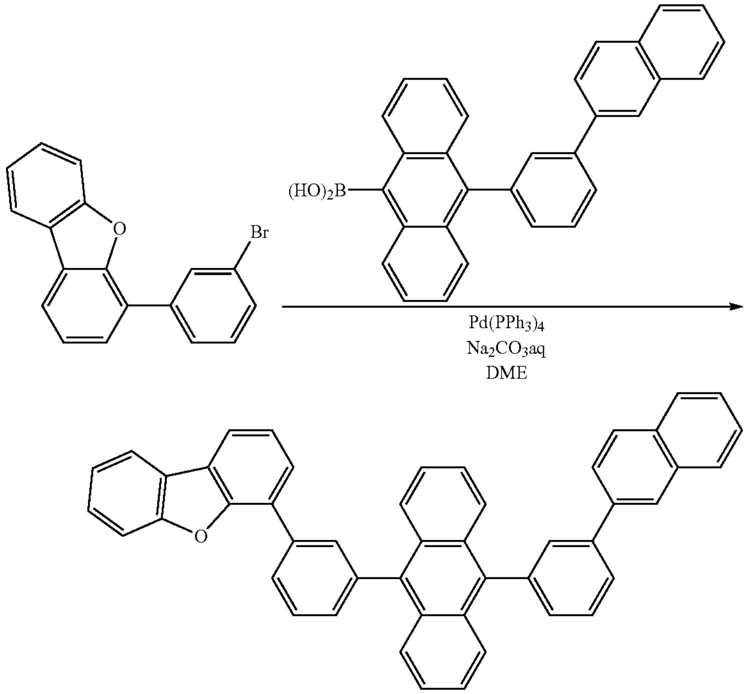

18

Mass spectral analysis confirmed the following: the product was the target product and had an m/e of 622, which was indicative of the molecular weight of the target product, i.e., 622.23.

Example-of-Synthesis 19

Synthesis of Compound 19

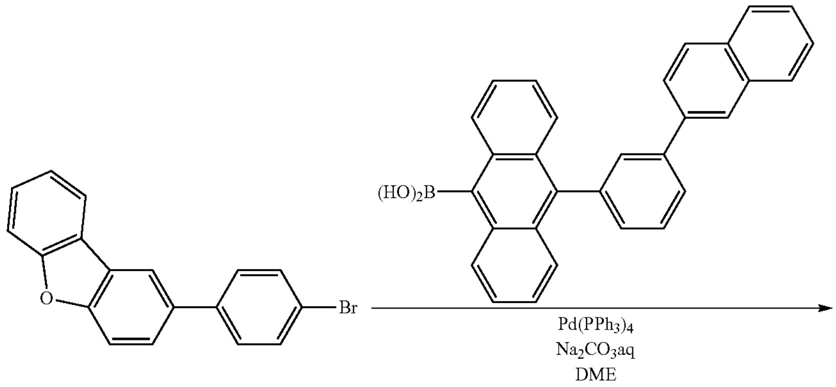

-continued

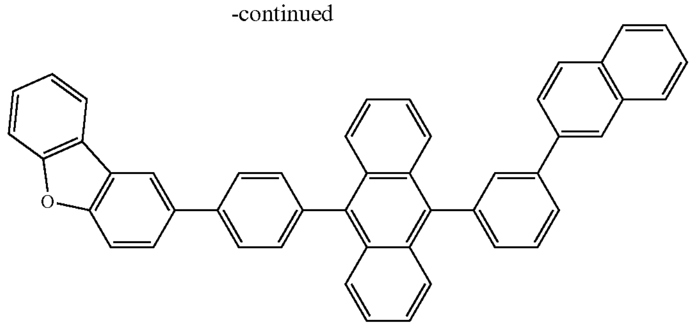

19

Compound 19 was synthesized in the same manner as in Example-of-Synthesis 1 except that: 2-(4-bromophenyl) dibenzofuran was used instead of 4-(4-bromophenyl)dibenzofuran; and 10-[3-(2-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 20

Synthesis of Compound 20

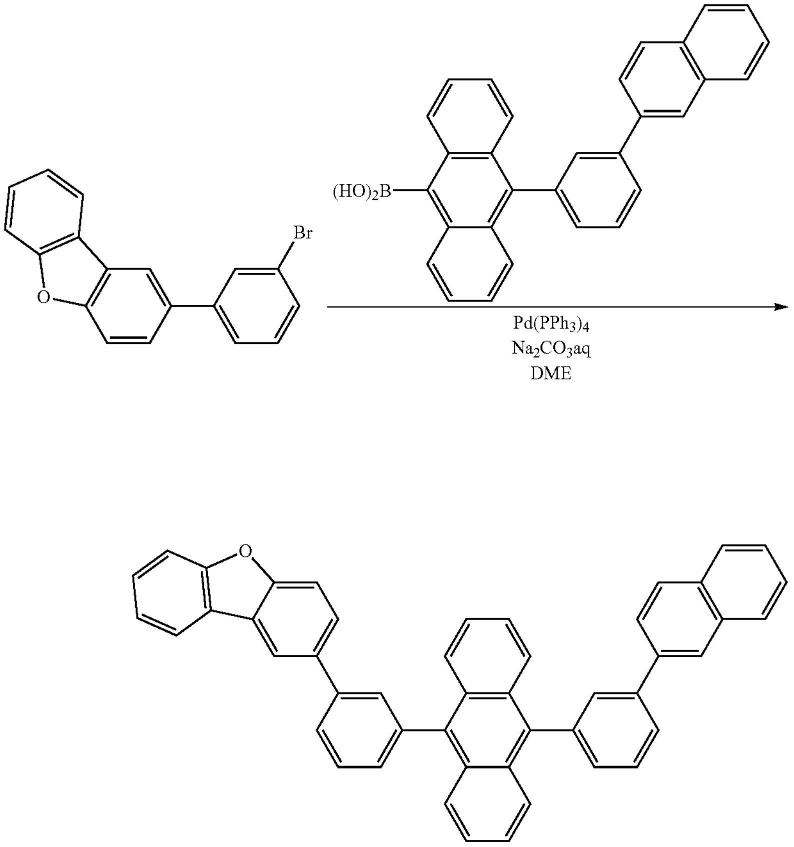

20

Compound 20 was synthesized in the same manner as in Example-of-Synthesis 1 except that: 2-(3-bromophenyl) dibenzofuran was used instead of 4-(4-bromophenyl)dibenzofuran; and 10-[3-(2-naphthyl)phenyl]anthracene-9-boronic acid was used instead of 10-(2-naphthyl)anthracene-9-boronic acid. Mass spectral analysis confirmed the following: the product was the target product and had an m/e of 622, which was indicative of the molecular weight of the target product, i.e., 622.23.

Example-of-Synthesis 21

Synthesis of Compound 21

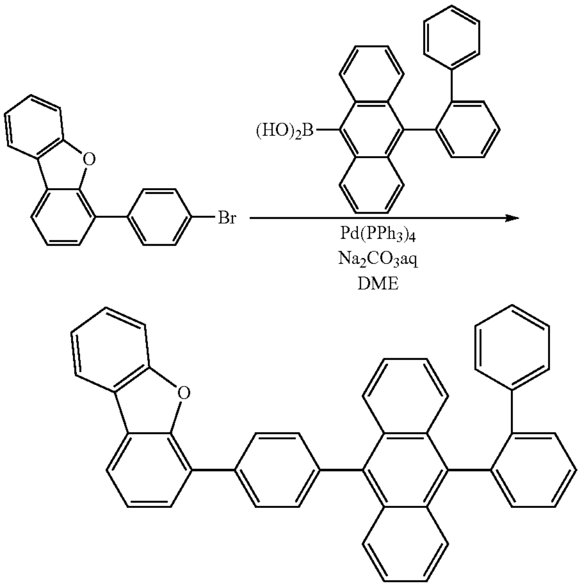

21

Compound 21 was synthesized in the same manner as in Example-of-Synthesis 1 except that: 4-(3-bromophenyl) dibenzofuran was used instead of 4-(4-bromophenyl)dibenzofuran; and 10-(2-biphenyl)anthracene-9-boronic acid was used instead of 10-(2-naphthyl)anthracene-9-boronic acid. Mass spectral analysis confirmed the following: the product was the target product and had an m/e of 572, which was indicative of the molecular weight of the target product, i.e., 572.21.

Example-of-Synthesis 22

Synthesis of Compound 22

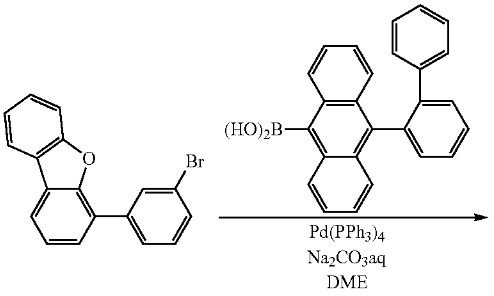

-continued

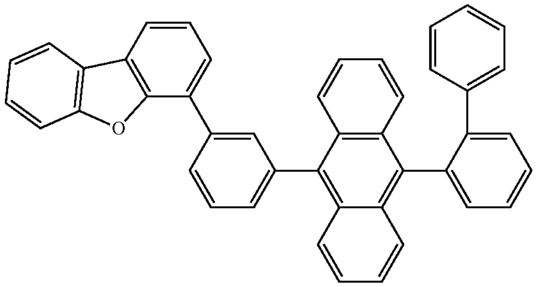

22

Compound 22 was synthesized in the same manner as in Example-of-Synthesis 1 except that: 4-(3-bromophenyl) dibenzofuran was used instead of 4-(4-bromophenyl)dibenzofuran; and 10-(2-biphenyl)anthracene-9-boronic acid was used instead of 10-(2-naphthyl)anthracene-9-boronic acid. Mass spectral analysis confirmed the following: the product was the target product and had an m/e of 572, which was indicative of the molecular weight of the target product, i.e., 572.21.

Example-of-Synthesis 23

Synthesis of Compound 23

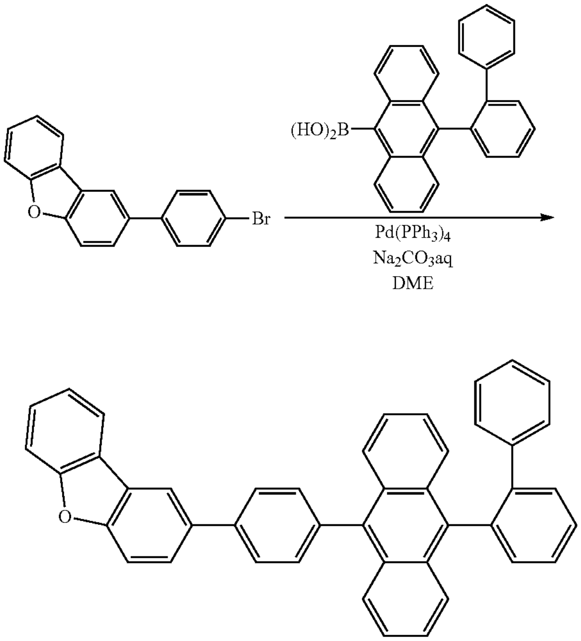

23

Compound 23 was synthesized in the same manner as in Example-of-Synthesis 1 except that: 2-(4-bromophenyl) dibenzofuran was used instead of 4-(4-bromophenyl)dibenzofuran; and 10-(2-biphenyl)anthracene-9-boronic acid was used instead of 10-(2-naphthyl)anthracene-9-boronic acid. Mass spectral analysis confirmed the following: the product was the target product and had an m/e of 572, which was indicative of the molecular weight of the target product, i.e., 572.21.

Example-of-Synthesis 24

Synthesis of Compound 24

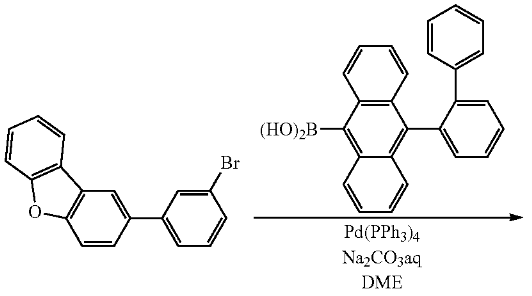

-continued

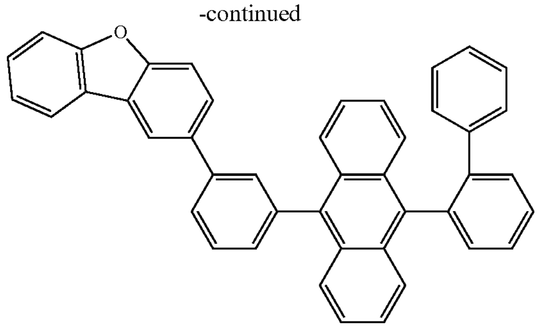

24

Compound 24 was synthesized in the same manner as in Example-of-Synthesis 1 except that: 2-(3-bromophenyl) dibenzofuran was used instead of 4-(4-bromophenyl)dibenzofuran; and 10-(2-biphenyl)anthracene-9-boronic acid was used instead of 10-(2-naphthyl)anthracene-9-boronic acid. Mass spectral analysis confirmed the following: the product was the target product and had an m/e of 572, which was indicative of the molecular weight of the target product, i.e., 572.21.

Example-of-Synthesis 25

Synthesis of Compound 25

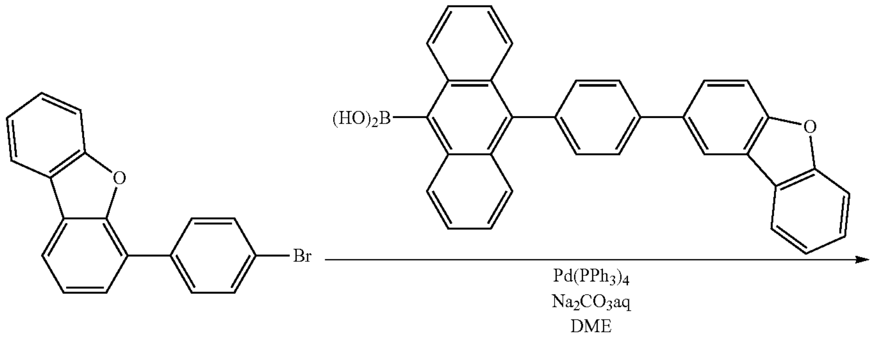

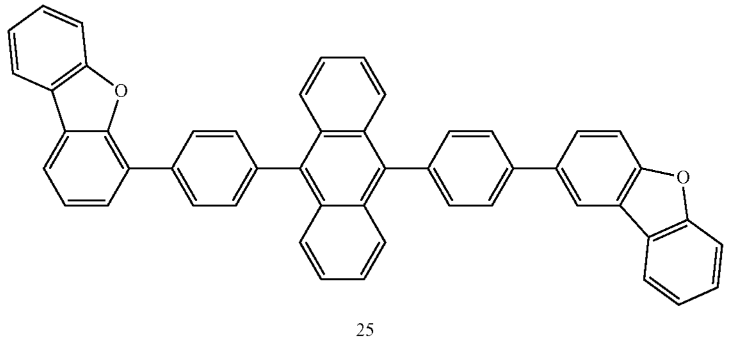

25

Compound 25 was synthesized in the same manner as in Example-of-Synthesis 1 except that 10-[4-(dibenzofuran-2-yl)phenyl]anthracene-9-boronic acid was used instead of 10-(2-naphthyl)anthracene-9-boronic acid. Mass spectral analysis confirmed the following: the product was the target product and had an m/e of 662, which was indicative of the molecular weight of the target product, i.e., 662.22.

Example-of-Synthesis 26

Synthesis of Compound 26

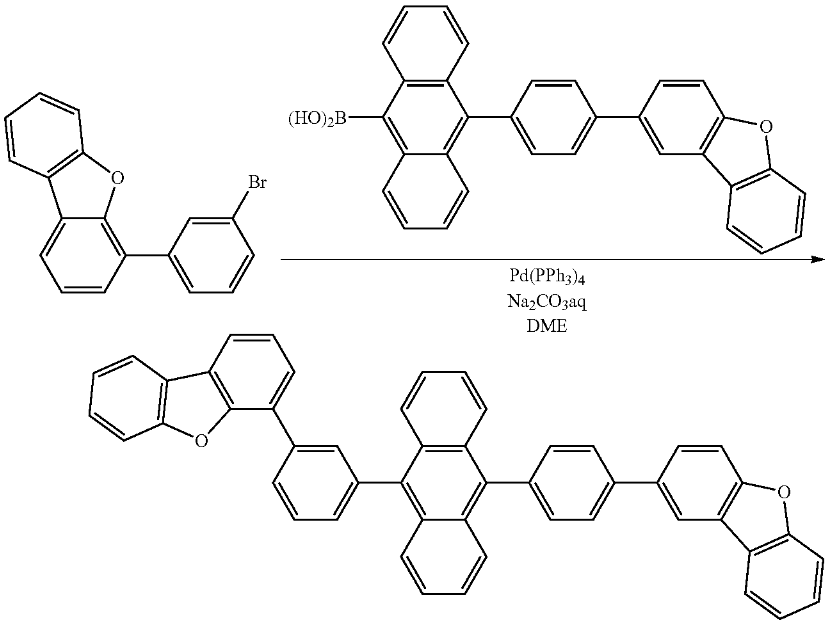

26

Compound 26 was synthesized in the same manner as in Example-of-Synthesis 1 except that: 4-(3-bromophenyl) dibenzofuran was used instead of 4-(4-bromophenyl)dibenzofuran; and 10-[4-(dibenzofuran-2-yl)phenyl]anthracene-9-boronic acid was used instead of 10-(2-naphthyl) anthracene-9-boronic acid. Mass spectral analysis confirmed the following: the product was the target product and had an m/e of 662, which was indicative of the molecular weight of the target product, i.e., 662.22.

Example-of-Synthesis 27

Synthesis of Compound 27

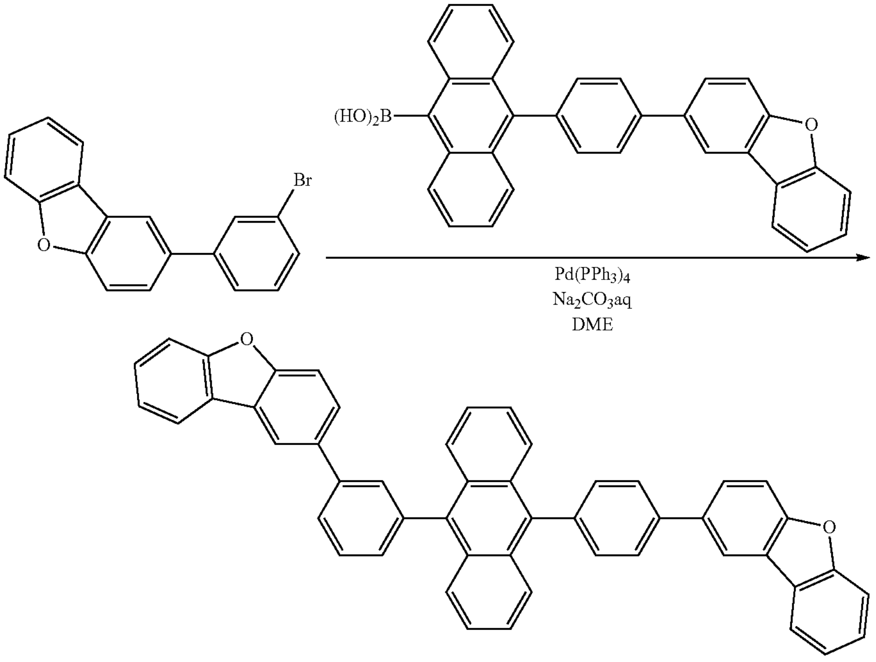

27

Compound 27 was synthesized in the same manner as in Example-of-Synthesis 1 except that: 2-(3-bromophenyl)dibenzofuran was used instead of 4-(4-bromophenyl)dibenzofuran; and 10-[4-(dibenzofuran-2-yl)phenyl]anthracene-9-boronic acid was used instead of 10-(2-naphthyl)anthracene-9-boronic acid. Mass spectral analysis confirmed the following: the product was the target product and had an m/e of 662, which was indicative of the molecular weight of the target product, i.e., 662.22.

Example-of-Synthesis 28

Synthesis of Compound 28

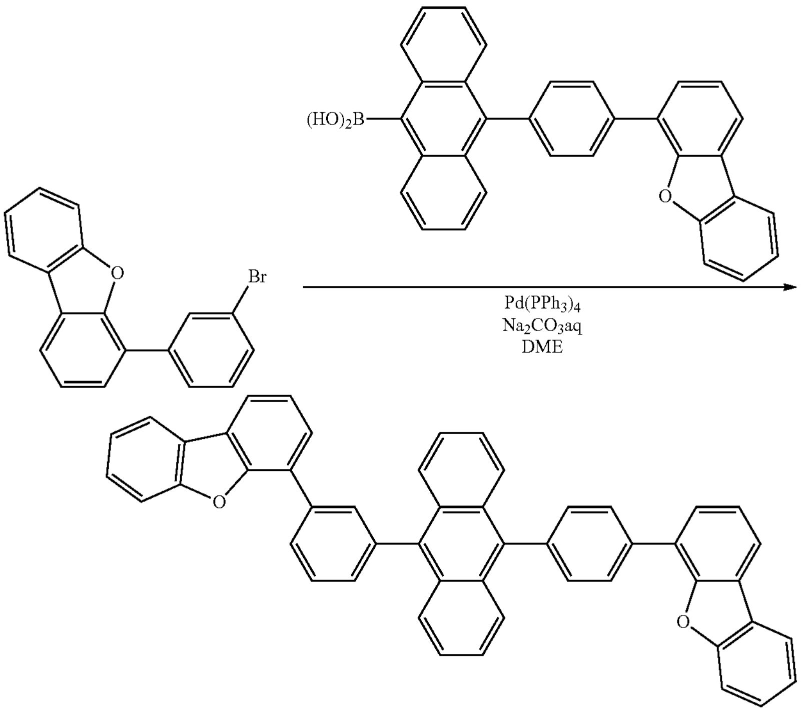

28

Compound 28 was synthesized in the same manner as in Example-of-Synthesis 1 except that: 4-(3-bromophenyl)dibenzofuran was used instead of 4-(4-bromophenyl)dibenzofuran; and 10-[4-(dibenzofuran-4-yl)phenyl]anthracene-9-boronic acid was used instead of 10-(2-naphthyl)anthracene-9-boronic acid. Mass spectral analysis confirmed the following: the product was the target product and had an m/e of 662, which was indicative of the molecular weight of the target product, i.e., 662.22.

Example-of-Synthesis 29

Synthesis of Compound 29

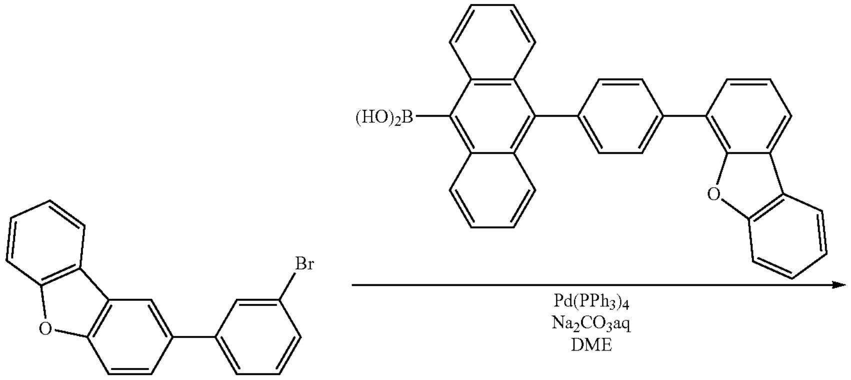

-continued

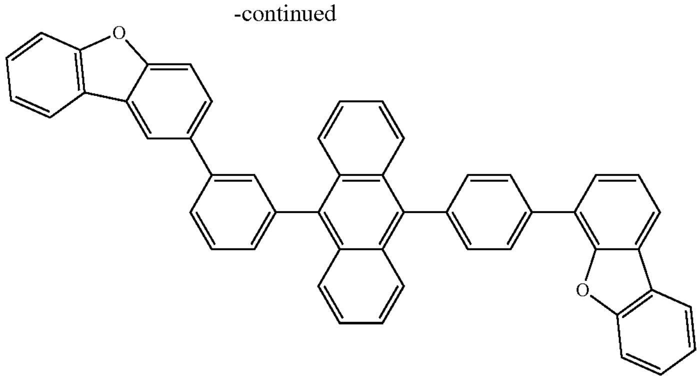

29

Compound 29 was synthesized in the same manner as in Example-of-Synthesis 1 except that: 2-(3-bromophenyl) dibenzofuran was used instead of 4-(4-bromophenyl)dibenzofuran; and 10-[4-(dibenzofuran-4-yl)phenyl]anthracene-9-boronic acid was used instead of 10-(2-naphthyl) anthracene-9-boronic acid. Mass spectral analysis confirmed the following: the product was the target product and had an m/e of 662, which was indicative of the molecular weight of the target product, i.e., 662.22.

Example-of-Synthesis 30

Synthesis of Compound 30

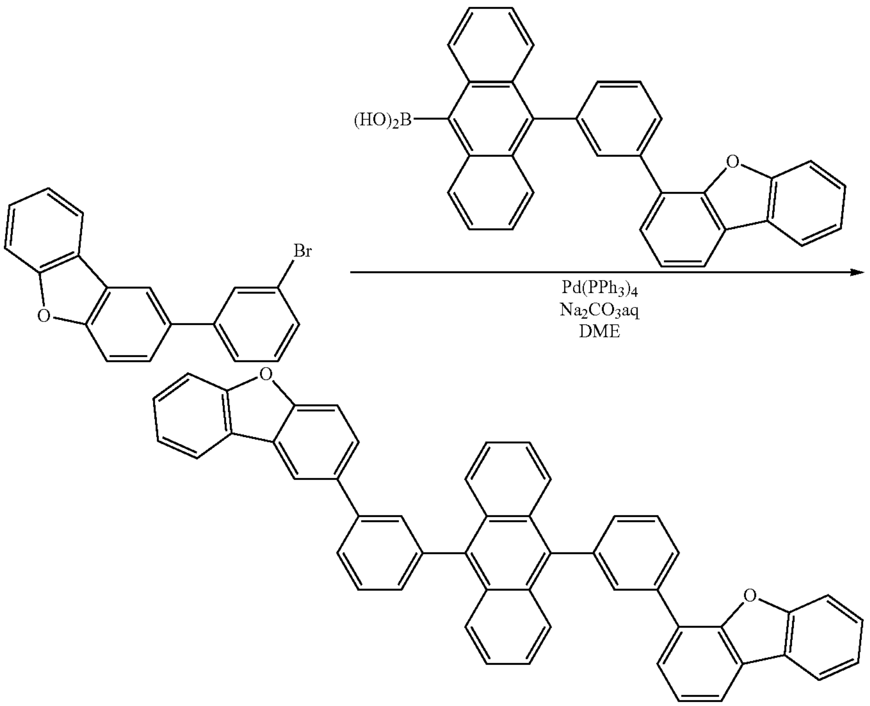

30

Compound 30 was synthesized in the same manner as in Example-of-Synthesis 1 except that: 2-(3-bromophenyl) dibenzofuran was used instead of 4-(4-bromophenyl)dibenzofuran; and 10-[3-(dibenzofuran-4-yl)phenyl]anthracene-9-boronic acid was used instead of 10-(2-naphthyl) anthracene-9-boronic acid. Mass spectral analysis confirmed the following: the product was the target product and had an m/e of 662, which was indicative of the molecular weight of the target product, i.e., 662.22.

Example-of-Synthesis 31

Synthesis of Compound 31

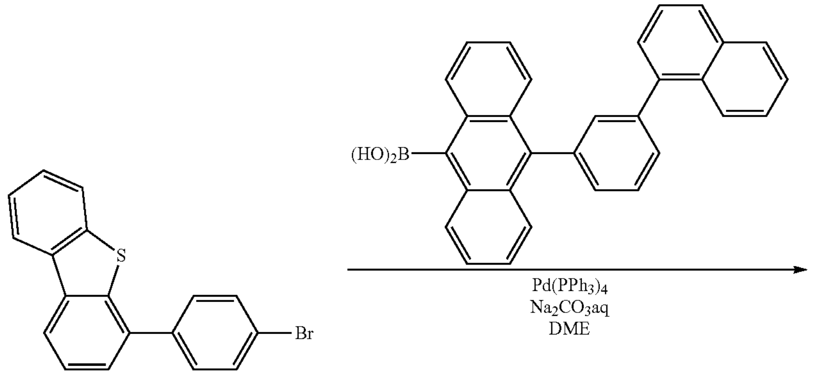

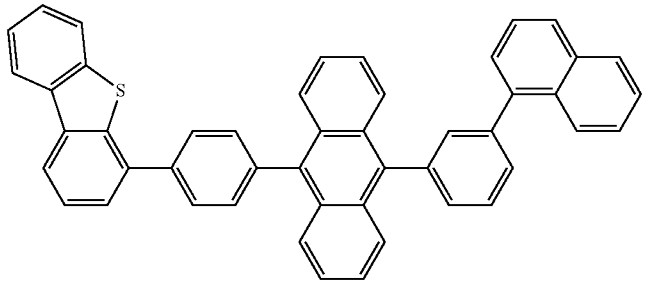

31

Compound 31 was synthesized in the same manner as in Example-of-Synthesis 1 except that: 4-(4-bromophenyl) dibenzothiophene was used instead of 4-(4-bromophenyl) dibenzofuran; and 10-[3-(1-naphthyl)phenyl]anthracene-9-boronic acid was used instead of 10-(2-naphthyl)anthracene-9-boronic acid. Mass spectral analysis confirmed the following: the product was the target product and had an m/e of 638, which was indicative of the molecular weight of the target product, i.e., 638.21.

Example-of-Synthesis 32

Synthesis of Compound 32

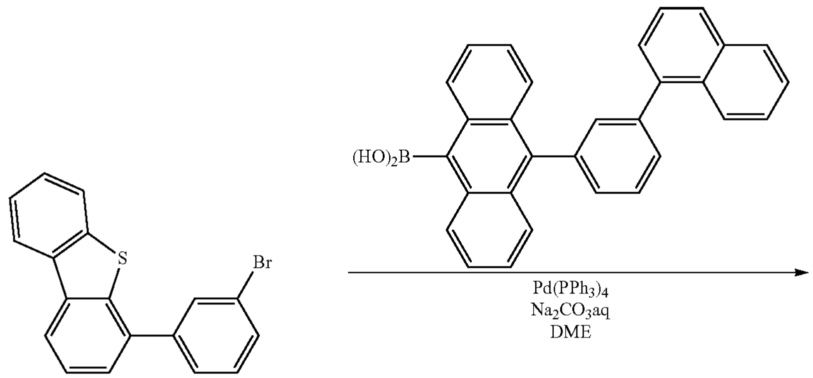

-continued

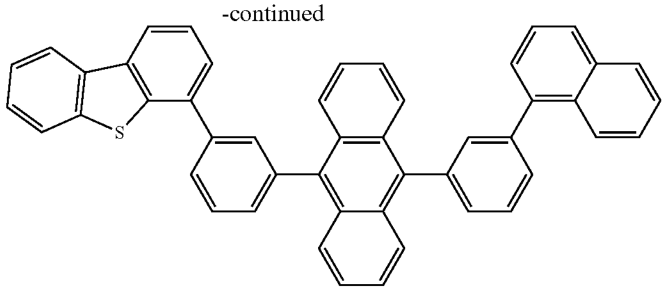

32

Compound 32 was synthesized in the same manner as in Example-of-Synthesis 1 except that: 4-(3-bromophenyl) dibenzothiophene was used instead of 4-(4-bromophenyl) dibenzofuran; and 10-[3-(1-naphthyl)phenyl]anthracene-9-boronic acid was used instead of 10-(2-naphthyl)anthracene-9-boronic acid. Mass spectral analysis confirmed the following: the product was the target product and had an m/e of 638, which was indicative of the molecular weight of the target product, i.e., 638.21.

Example-of-Synthesis 33

Synthesis of Compound 33

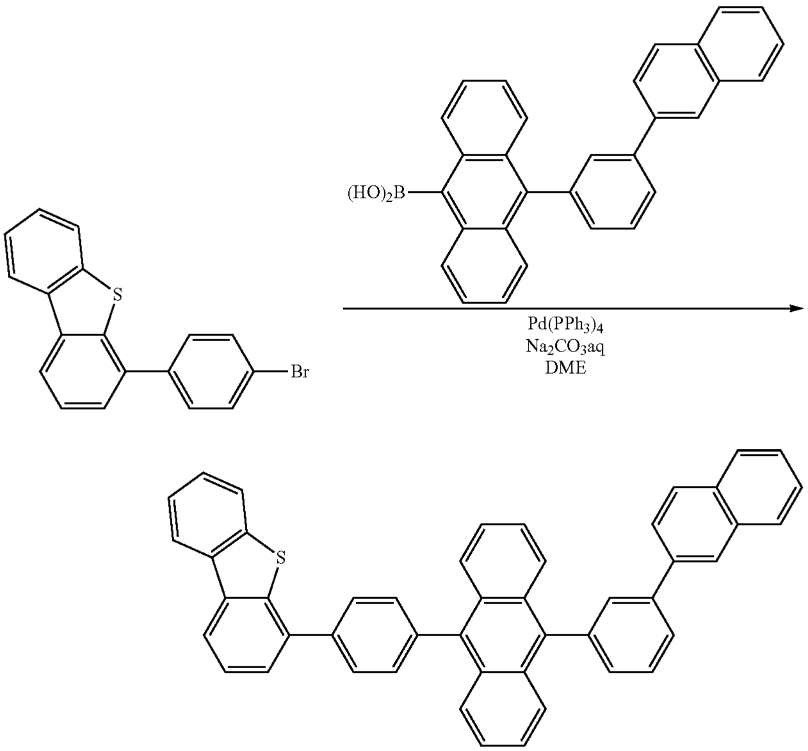

33

Compound 33 was synthesized in the same manner as in Example-of-Synthesis 1 except that: 4-(4-bromophenyl) dibenzothiophene was used instead of 4-(4-bromophenyl) dibenzofuran; and 10-[3-(2-naphthyl)phenyl]anthracene-9-boronic acid was used instead of 10-(2-naphthyl)anthracene-9-boronic acid. Mass spectral analysis confirmed the following: the product was the target product and had an m/e of 638, which was indicative of the molecular weight of the target product, i.e., 638.21.

Example-of-Synthesis 34

Synthesis of Compound 34

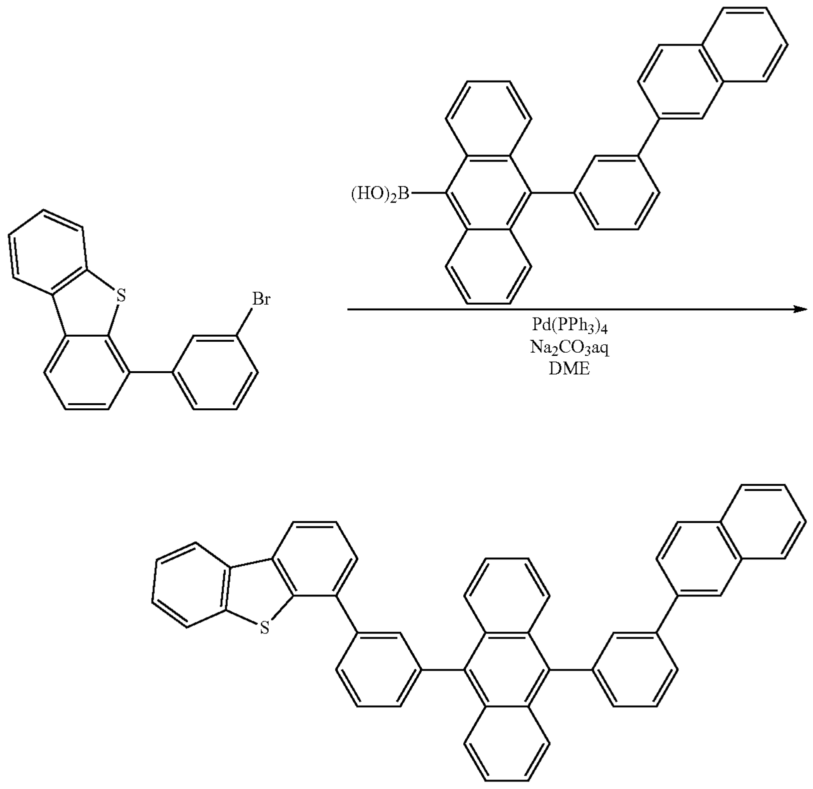

34

Compound 34 was synthesized in the same manner as in Example-of-Synthesis 1 except that: 4-(3-bromophenyl)dibenzothiophene was used instead of 4-(4-bromophenyl)dibenzofuran; and 10-[3-(2-naphthyl)phenyl]anthracene-9-boronic acid was used instead of 10-(2-naphthyl)anthracene-9-boronic acid. Mass spectral analysis confirmed the following: the product was the target product and had an m/e of 638, which was indicative of the molecular weight of the target product, i.e., 638.21.

Example-of-Synthesis 35

Synthesis of Compound 35

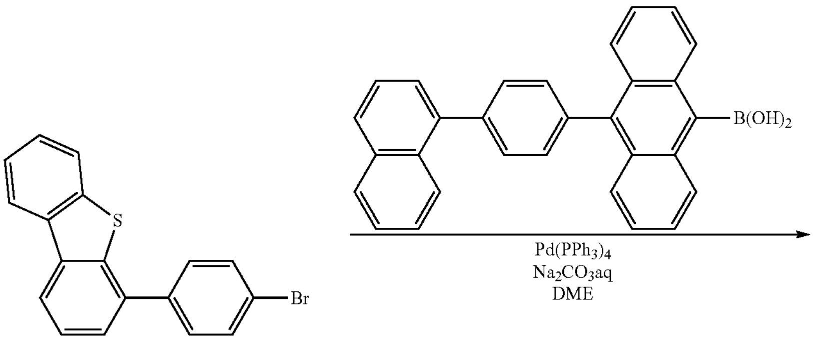

-continued

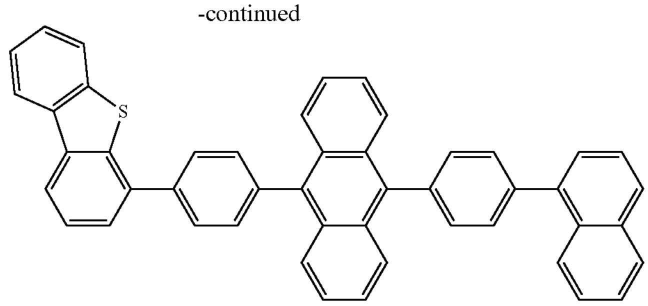

35

Compound 35 was synthesized in the same manner as in Example-of-Synthesis 1 except that: 4-(4-bromophenyl) dibenzothiophene was used instead of 4-(4-bromophenyl) dibenzofuran; and 10-[4-(1-naphthyl)phenyl]anthracene-9-boronic acid was used instead of 10-(2-naphthyl)anthracene-9-boronic acid. Mass spectral analysis confirmed the following: the product was the target product and had an m/e of 638, which was indicative of the molecular weight of the target product, i.e., 638.21.

Example-of-Synthesis 36

Synthesis of Compound 36

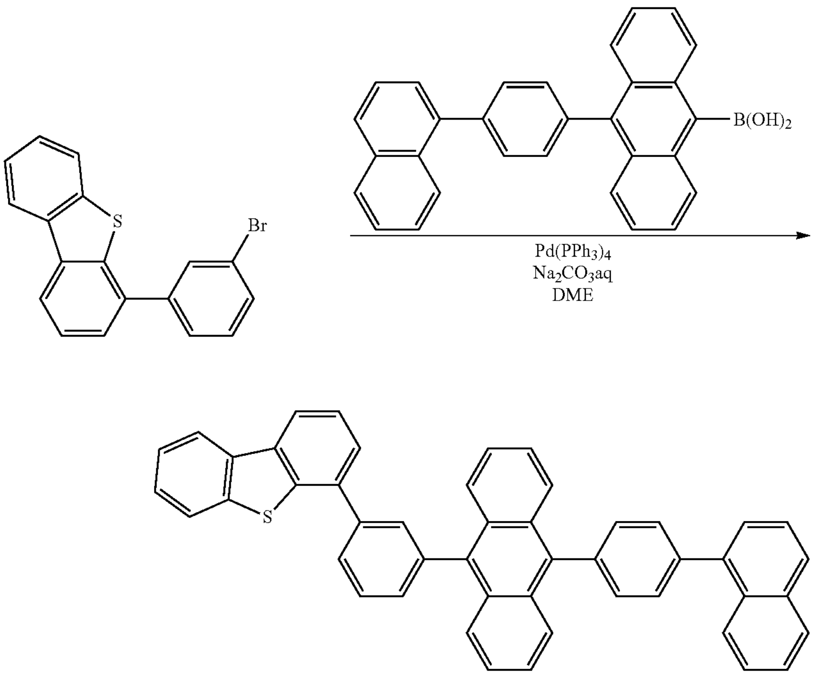

36

Compound 36 was synthesized in the same manner as in Example-of-Synthesis 1 except that: 4-(3-bromophenyl) dibenzothiophene was used instead of 4-(4-bromophenyl) dibenzofuran; and 10-[4-(1-naphthyl)phenyl]anthracene-9-boronic acid was used instead of 10-(2-naphthyl)anthracene-9-boronic acid. Mass spectral analysis confirmed the following: the product was the target product and had an m/e of 638, which was indicative of the molecular weight of the target product, i.e., 638.21.

Example-of-Synthesis 37

Synthesis of Compound 37

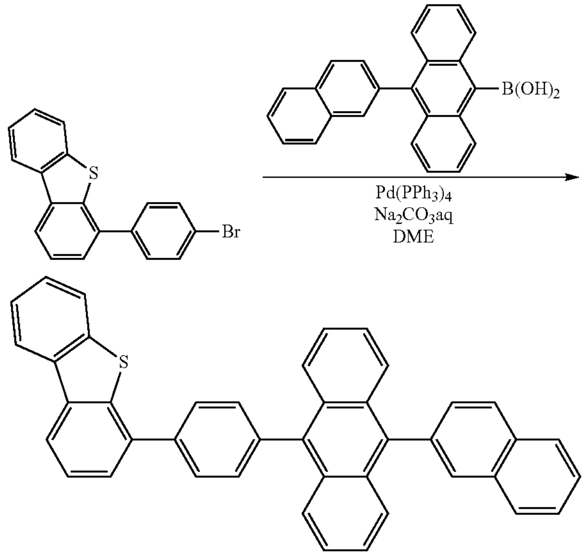

37

Compound 37 was synthesized in the same manner as in Example-of-Synthesis 1 except that 4-(4-bromophenyl) dibenzothiophene was used instead of 4-(4-bromophenyl) dibenzofuran. Mass spectral analysis confirmed the following: the product was the target product and had an m/e of 562, which was indicative of the molecular weight of the target product, i.e., 562.18.

Example-of-Synthesis 38

Synthesis of Compound 38

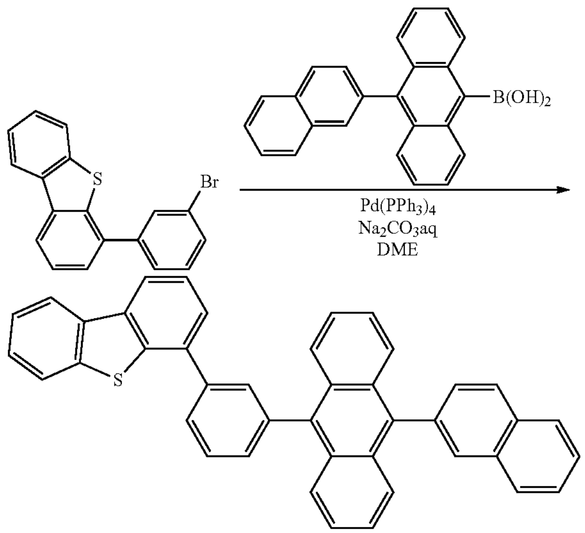

38

Compound 38 was synthesized in the same manner as in Example-of-Synthesis 1 except that 4-(3-bromophenyl) dibenzothiophene was used instead of 4-(4-bromophenyl) dibenzofuran. Mass spectral analysis confirmed the following: the product was the target product and had an m/e of 562, which was indicative of the molecular weight of the target product, i.e., 562.18.

Example-of-Synthesis 39

Synthesis of Compound 39

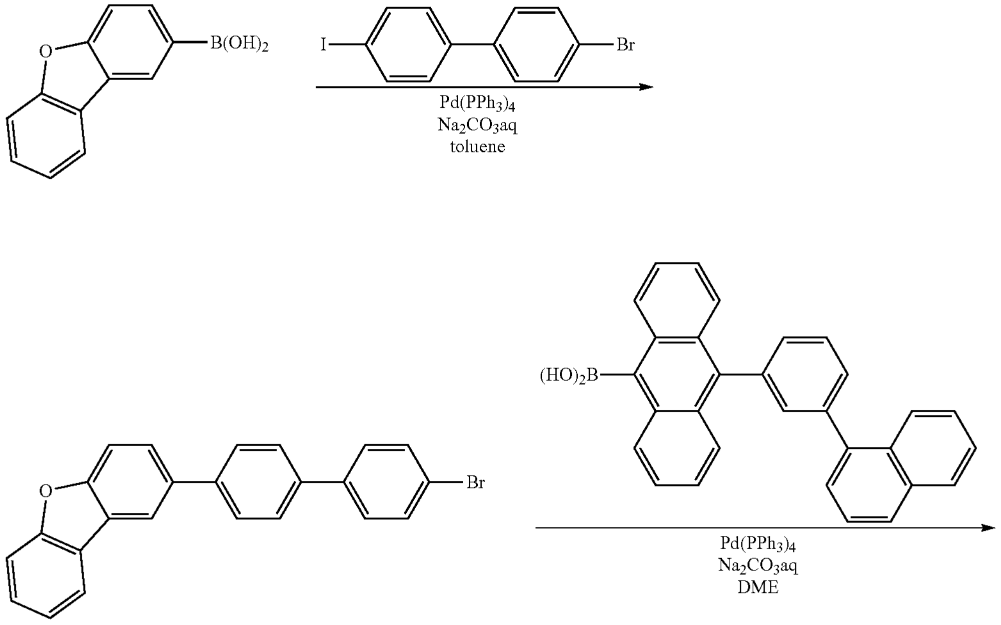

-continued

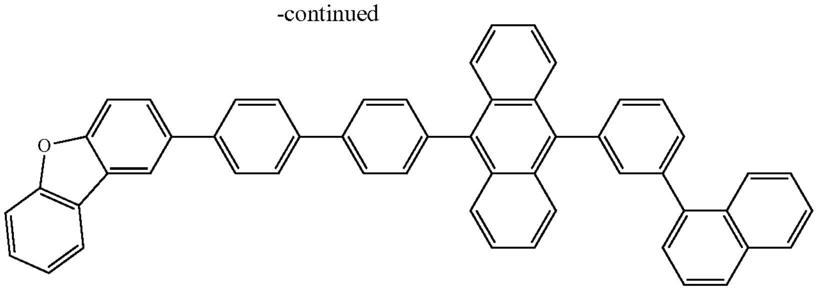

39

(39-1) Synthesis of 2-(4'-bromobiphenyl-4-yl)dibenzofuran 2-(4'-bromophenyl-4-yl)dibenzofuran was synthesized in the same manner as in the synthesis of 2-(4-bromophenyl) dibenzofuran except that 4-bromo-4'-iodobiphenyl was used instead of 4-bromoiodobenzene.

(39-2) Synthesis of Compound 39

Compound 39 was synthesized in the same manner as in Example-of-Synthesis 1 except that: 2-(4'-bromophenyl-4-yl)dibenzofuran was used instead of 4-(4-bromophenyl) dibenzofuran; and 10-[3-(1-naphthyl)phenyl]anthracene-9-boronic acid was used instead of 10-(2-naphthyl)anthracene-9-boronic acid. Mass spectral analysis confirmed the following: the product was the target product and had an m/e of 698, which was indicative of the molecular weight of the target product, i.e., 698.26.

Example-of-Synthesis 40

Synthesis of Compound 40

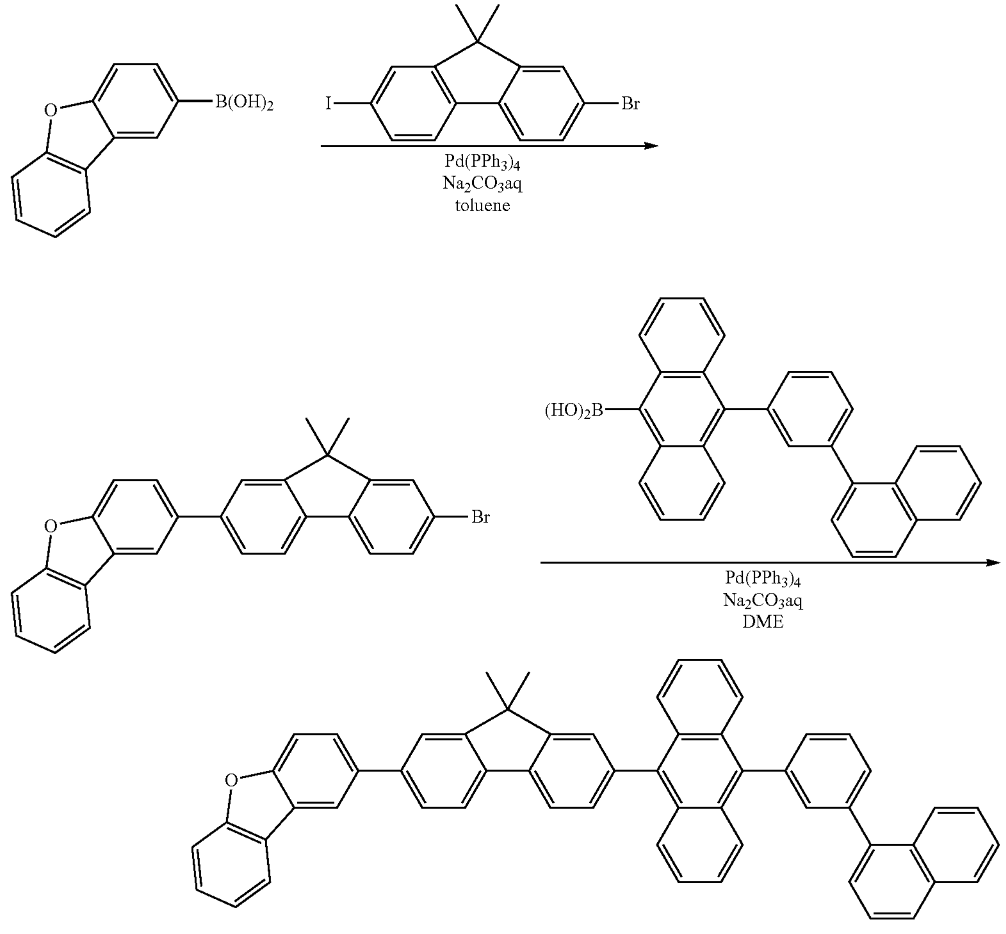

40

(40-1) Synthesis of 2-(7-bromo-9,9-dimethylfluoren-2-yl)dibenzofuran 2-(7-bromo-9,9-dimethylfluoren-2-yl)dibenzofuran was synthesized in the same manner as in the synthesis of 2-(4-bromophenyl)dibenzofuran except that 2-bromo-7-iodo-9,9-dimethylfluorene was used instead of 4-bromoiodobenzene.

(40-2) Synthesis of Compound 34

Compound 40 was synthesized in the same manner as in Example-of-Synthesis 1 except that: 2-(7-bromo-9,9-dimethylfluoren-2-yl)dibenzofuran was used instead of 4-(4-bromophenyl)dibenzofuran; and 10-[3-(1-naphthyl)phenyl]anthracene-9-boronic acid was used instead of 10-(2-naphthyl)anthracene-9-boronic acid. Mass spectral analysis confirmed the following: the product was the target product and had an m/e of 738, which was indicative of the molecular weight of the target product, i.e., 738.29.

Example-of-Synthesis 41

Synthesis of Compound 41

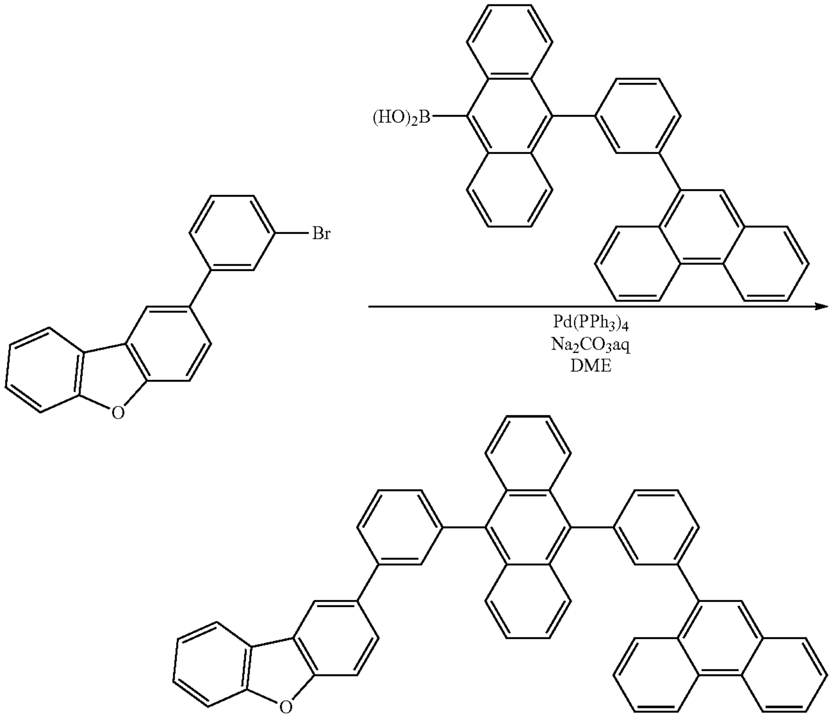

41

Compound 41 was synthesized in the same manner as in Example-of-Synthesis 1 except that: 2-(3-bromophenyl)dibenzofuran was used instead of 4-(4-bromophenyl)dibenzofuran; and 10-[3-(2-naphthyl)phenyl]anthracene-9-boronic acid was used instead of 10-(2-naphthyl)anthracene-9-boronic acid. Mass spectral analysis confirmed the following: the product was the target product and had an m/e of 672, which was indicative of the molecular weight of the target product, i.e., 672.25.

Example-of-Synthesis 42

Synthesis of Compound 42

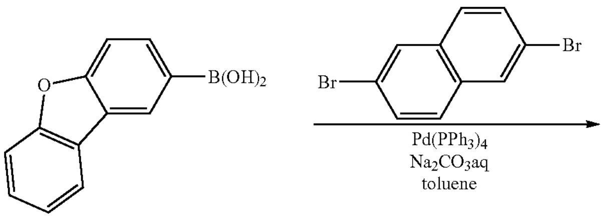

-continued

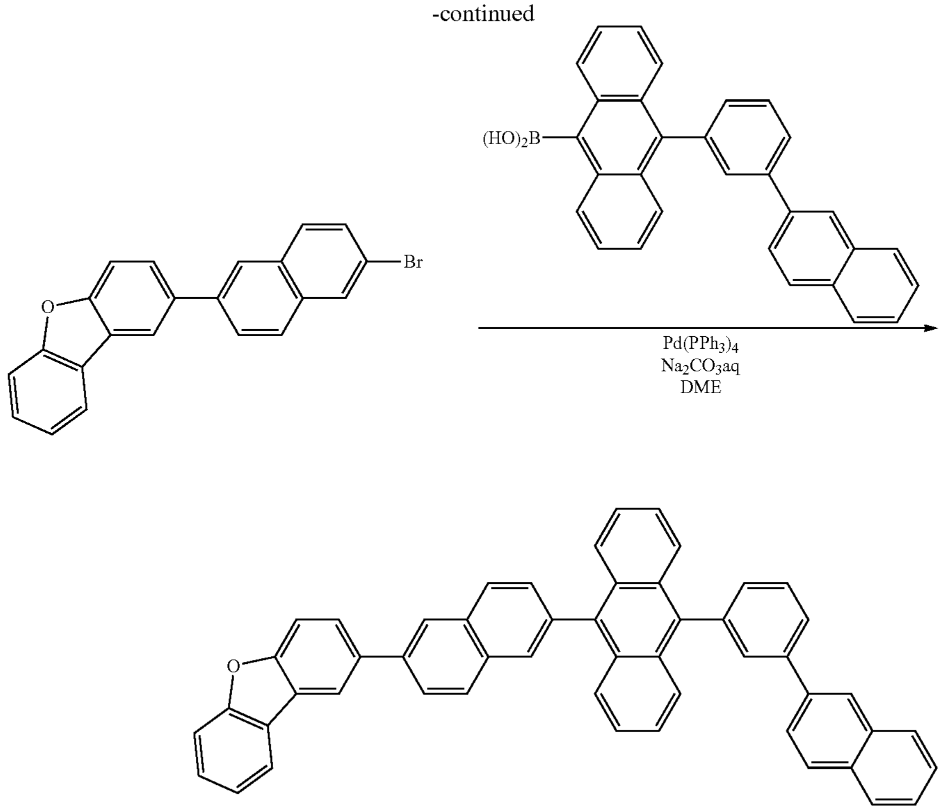

42

(42-1) Synthesis of 2-(6-bromonaphthalen-2-yl)dibenzofuran 2-(6-bromonaphthalen-2-yl)dibenzofuran was synthesized in the same manner as in the synthesis of 4-(4-bromophenyl)dibenzofuran except that 2,6-dibromonaphthalene was used instead of 4-bromoiodobenzene.

(42-2) Synthesis of Compound 42

Compound 42 was synthesized in the same manner as in Example-of-Synthesis 1 except that: 2-(6-dibromonaphthalene-2-yl)dibenzofuran was used instead of 4-(4-bromophenyl)dibenzofuran; and 10-[3-(2-naphthyl)phenyl]anthracene-9-boronic acid was used instead of 10-(2-naphthyl) anthracene-9-boronic acid. Mass spectral analysis confirmed the following: the product was the target product and had an m/e of 672, which was indicative of the molecular weight of the target product, i.e., 672.25.

Example 5

A glass substrate measuring 25 mm wide by 75 mm long by 1.1 mm thick and provided with an ITO transparent electrode (anode) (manufactured by GEOMATEC Co., Ltd.) was subjected to ultrasonic cleaning in isopropyl alcohol for 5 minutes, and was then subjected to UV/ozone cleaning for 30 minutes. The glass substrate with the transparent electrode line after the cleaning was mounted on a substrate holder of a vacuum vapor deposition apparatus. First, Compound A-1 shown below was formed into a film having a thickness of 60 nm on the surface on the side where the transparent electrode line was formed so as to cover the transparent electrode. Subsequently, Compound A-2 shown below was formed into a film having a thickness of 20 nm on the A-1 film.

Further, Compound 1 shown above of the present invention and Styrylamine Derivative D-1 shown below were formed into a film having a thickness of 40 nm at a thickness ratio of 40:2 on the A-2 film, whereby a bluish light emitting layer was obtained. Compound 5 functions as a host while Styrylamine Derivative D-1 functions as a dopant.

Alq having the following structure was formed into a film having a thickness of 20 nm by vapor deposition on the film so as to serve as an electron transporting layer. After that, LiF was formed into a film having a thickness of 1 nm. Metal aluminum was deposited from the vapor onto the LiF film so that a metal cathode having a thickness of 150 nm was formed. Thus, an organic EL device was formed.

The device performance of the resultant organic EL device when the device was driven at a current density of 10 mA/cm$^2$, and a lifetime required for an initial luminance of 1,000 cd/m$^2$ to reduce in half were measured. Table 2 shows the results.

D-1

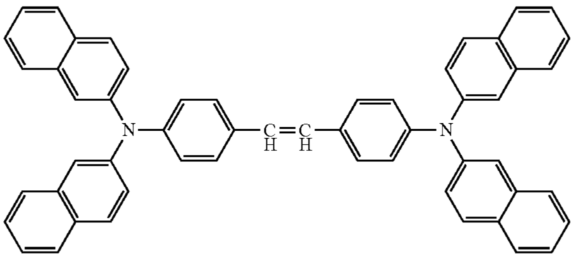

Alq

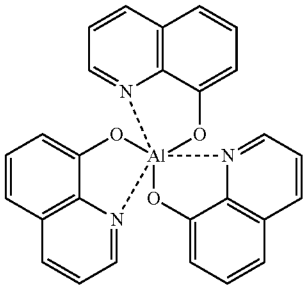

A-1

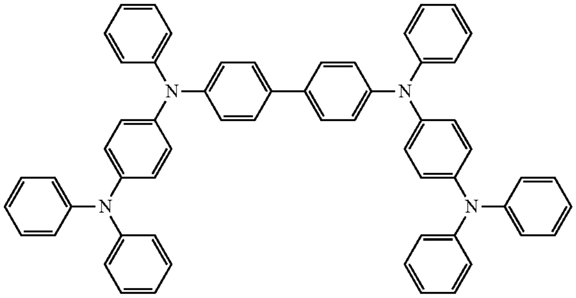

-continued

A-2

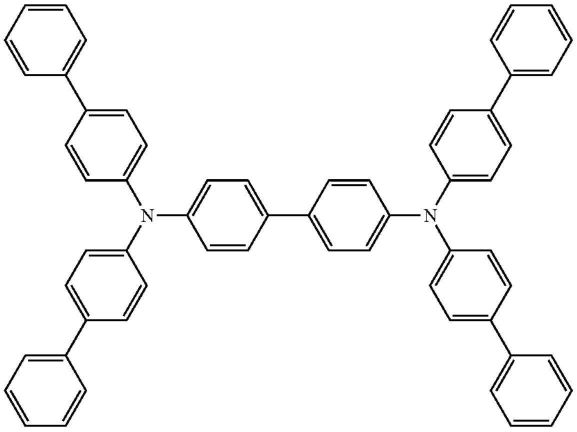

Examples 6 to 42

Organic EL devices were each produced in the same manner as in Example 5 except that any one of Compounds 2 to 38 shown above was used instead of Compound 1, and the devices were each evaluated in the same manner as in Example 5. Table 2 shows the results.

Comparative Examples 9 to 16

Organic EL devices were each produced in the same manner as in Example 5 except that any one of Compounds A to H shown below was used instead of Compound 1, and the devices were each evaluated in the same manner as in Example 5. Table 2 shows the results.

A

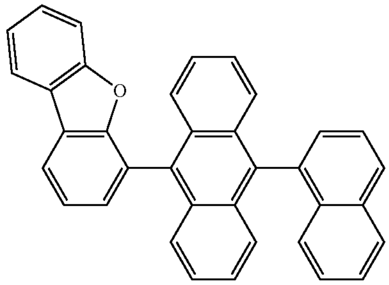

B

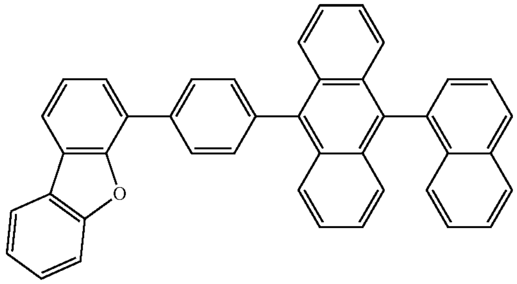

C

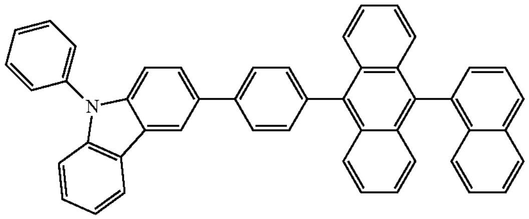

D

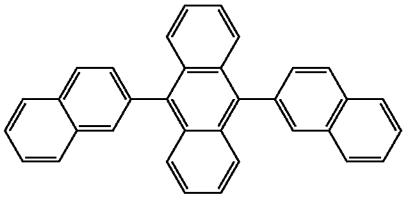

-continued

E

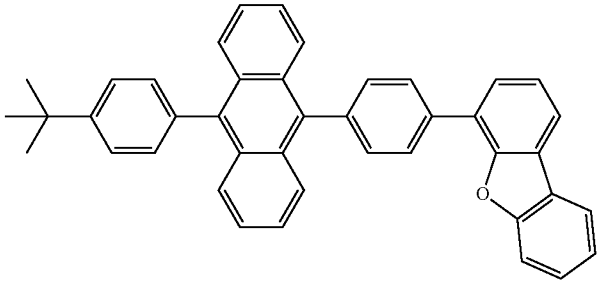

F

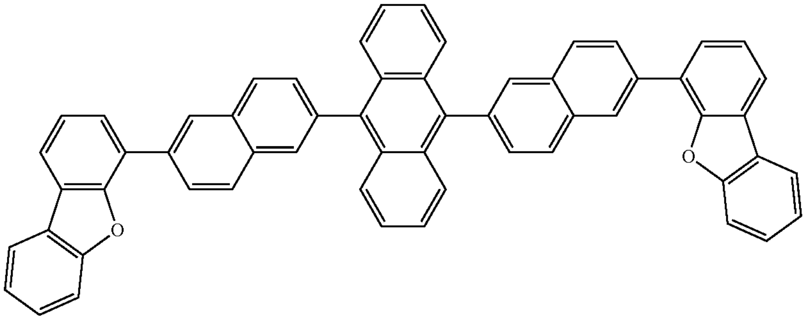

G

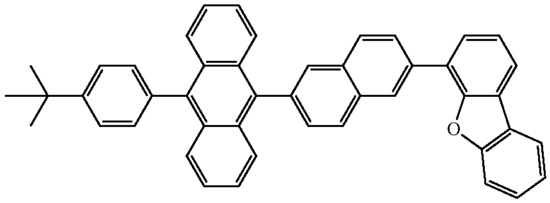

H

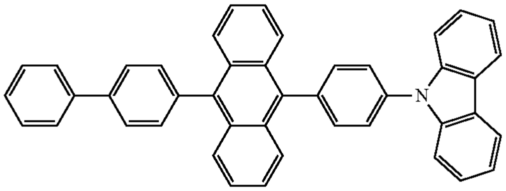

TABLE 2

| | Host | Dopant | Voltage (V) | Current efficiency (cd/A) | Luminescent color | Lifetime |
|---|---|---|---|---|---|---|
| Example 5 | Compound 1 | D-1 | 6.5 | 7.5 | Blue | 8,000 |
| Example 6 | Compound 2 | D-1 | 6.6 | 7.5 | Blue | 7,000 |
| Example 7 | Compound 3 | D-1 | 6.5 | 7.8 | Blue | 7,000 |
| Example 8 | Compound 4 | D-1 | 6.7 | 7.8 | Blue | 8,000 |
| Example 9 | Compound 5 | D-1 | 6.5 | 7.4 | Blue | 8,000 |
| Example 10 | Compound 6 | D-1 | 6.6 | 7.5 | Blue | 8,000 |
| Example 11 | Compound 7 | D-1 | 6.6 | 7.8 | Blue | 8,000 |
| Example 12 | Compound 8 | D-1 | 6.6 | 7.8 | Blue | 8,000 |
| Example 13 | Compound 9 | D-1 | 6.5 | 7.5 | Blue | 8,000 |
| Example 14 | Compound 10 | D-1 | 6.7 | 7.5 | Blue | 8,000 |
| Example 15 | Compound 11 | D-1 | 6.5 | 7.8 | Blue | 8,000 |
| Example 16 | Compound 12 | D-1 | 6.5 | 7.8 | Blue | 8,000 |
| Example 17 | Compound 13 | D-1 | 6.6 | 7.4 | Blue | 8,000 |
| Example 18 | Compound 14 | D-1 | 6.6 | 7.5 | Blue | 8,000 |
| Example 19 | Compound 15 | D-1 | 6.5 | 7.8 | Blue | 8,000 |
| Example 20 | Compound 16 | D-1 | 6.7 | 7.8 | Blue | 8,000 |
| Example 21 | Compound 17 | D-1 | 6.5 | 7.4 | Blue | 8,000 |
| Example 22 | Compound 18 | D-1 | 6.6 | 7.4 | Blue | 8,000 |
| Example 23 | Compound 19 | D-1 | 6.5 | 7.8 | Blue | 8,000 |
| Example 24 | Compound 20 | D-1 | 6.7 | 7.8 | Blue | 8,000 |
| Example 25 | Compound 21 | D-1 | 6.5 | 7.4 | Blue | 7,000 |
| Example 26 | Compound 22 | D-1 | 6.6 | 7.4 | Blue | 7,000 |
| Example 27 | Compound 23 | D-1 | 6.5 | 7.8 | Blue | 7,000 |
| Example 28 | Compound 24 | D-1 | 6.7 | 7.8 | Blue | 8,000 |
| Example 29 | Compound 25 | D-1 | 6.5 | 7.8 | Blue | 8,000 |
| Example 30 | Compound 26 | D-1 | 6.6 | 7.8 | Blue | 8,000 |
| Example 31 | Compound 27 | D-1 | 6.5 | 7.8 | Blue | 8,000 |
| Example 32 | Compound 28 | D-1 | 6.7 | 7.4 | Blue | 8,000 |
| Example 33 | Compound 29 | D-1 | 6.5 | 7.8 | Blue | 8,000 |
| Example 34 | Compound 30 | D-1 | 6.6 | 7.8 | Blue | 8,000 |
| Example 35 | Compound 31 | D-1 | 6.5 | 7.0 | Blue | 7,000 |

TABLE 2-continued

| | Host | Dopant | Voltage (V) | Current efficiency (cd/A) | Luminescent color | Lifetime |
|---|---|---|---|---|---|---|
| Example 36 | Compound 32 | D-1 | 6.7 | 7.0 | Blue | 7,000 |
| Example 37 | Compound 33 | D-1 | 6.5 | 7.0 | Blue | 7,000 |
| Example 38 | Compound 34 | D-1 | 6.6 | 7.0 | Blue | 7,000 |
| Example 39 | Compound 35 | D-1 | 6.5 | 7.0 | Blue | 7,000 |
| Example 40 | Compound 36 | D-1 | 6.7 | 7.0 | Blue | 7,000 |
| Example 41 | Compound 37 | D-1 | 6.5 | 7.0 | Blue | 7,000 |
| Example 42 | Compound 38 | D-1 | 6.6 | 7.0 | Blue | 7,000 |
| Comparative Example 9 | Compound A | D-1 | 6.6 | 6.5 | Blue | 4,000 |
| Comparative Example 10 | Compound B | D-1 | 6.7 | 6.6 | Blue | 5,000 |
| Comparative Example 11 | Compound C | D-1 | 7.0 | 5.5 | Bluish green | 500 |
| Comparative Example 12 | Compound D | D-1 | 7.3 | 6.0 | Blue | 4,000 |
| Comparative Example 13 | Compound E | D-1 | 7.3 | 6.0 | Blue | 2,000 |
| Comparative Example 14 | Compound F | D-1 | 7.3 | 6.0 | Blue | 2,000 |
| Comparative Example 15 | Compound G | D-1 | 7.3 | 6.0 | Blue | 2,000 |
| Comparative Example 16 | Compound H | D-1 | 7.3 | 6.0 | Blue | 2,000 |

Examples 43 to 80 and Comparative Examples 17 to 24

Organic EL devices were each produced in the same manner as in each of Examples 5 to 42 and Comparative Examples 9 to 16 except that Benzimidazole Derivative E-1 shown below was used as an electron transporting material and Chrysene Derivative D-2 shown below was used as a dopant. Table 3 shows the results.

E-1

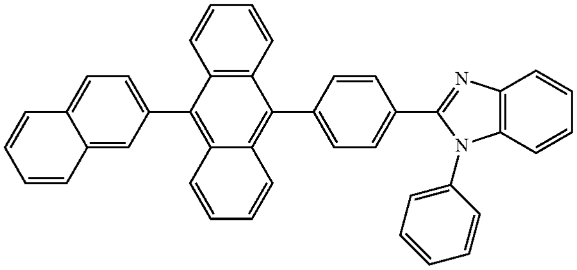

-continued

D-2

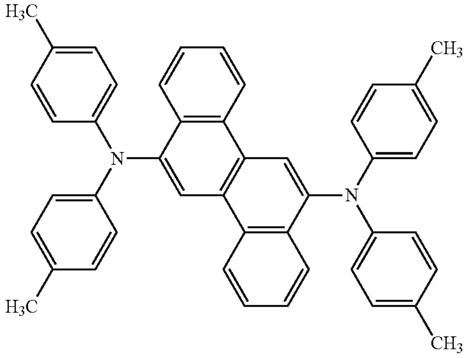

TABLE 3

| | Host | Dopant | Voltage (V) | Current efficiency (cd/A) | Luminescent color | Lifetime |
|---|---|---|---|---|---|---|
| Example 43 | Compound 1 | D-2 | 5.5 | 7.6 | Blue | 6,000 |
| Example 44 | Compound 2 | D-2 | 5.6 | 7.7 | Blue | 6,000 |
| Example 45 | Compound 3 | D-2 | 5.6 | 8.0 | Blue | 6,000 |
| Example 46 | Compound 4 | D-2 | 5.6 | 8.0 | Blue | 6,000 |
| Example 47 | Compound 5 | D-2 | 5.5 | 8.2 | Blue | 9,000 |
| Example 48 | Compound 6 | D-2 | 5.7 | 8.2 | Blue | 9,000 |
| Example 49 | Compound 7 | D-2 | 5.5 | 8.2 | Blue | 9,000 |
| Example 50 | Compound 8 | D-2 | 5.5 | 8.2 | Blue | 9,000 |
| Example 51 | Compound 9 | D-2 | 5.6 | 8.2 | Blue | 9,000 |
| Example 52 | Compound 10 | D-2 | 5.6 | 8.2 | Blue | 9,000 |
| Example 53 | Compound 11 | D-2 | 5.5 | 8.2 | Blue | 9,000 |
| Example 54 | Compound 12 | D-2 | 5.7 | 8.2 | Blue | 9,000 |
| Example 55 | Compound 13 | D-2 | 5.5 | 8.2 | Blue | 9,000 |
| Example 56 | Compound 14 | D-2 | 5.6 | 8.2 | Blue | 9,000 |
| Example 57 | Compound 15 | D-2 | 5.5 | 8.2 | Blue | 9,000 |
| Example 58 | Compound 16 | D-2 | 5.7 | 8.2 | Blue | 9,000 |
| Example 59 | Compound 17 | D-2 | 5.5 | 8.2 | Blue | 9,000 |
| Example 60 | Compound 18 | D-2 | 5.6 | 8.2 | Blue | 9,000 |

TABLE 3-continued

| | Host | Dopant | Voltage (V) | Current efficiency (cd/A) | Luminescent color | Lifetime |
|---|---|---|---|---|---|---|
| Example 61 | Compound 19 | D-2 | 5.5 | 8.2 | Blue | 9,000 |
| Example 62 | Compound 20 | D-2 | 5.7 | 8.2 | Blue | 9,000 |
| Example 63 | Compound 21 | D-2 | 5.5 | 8.0 | Blue | 7,000 |
| Example 64 | Compound 22 | D-2 | 5.6 | 8.0 | Blue | 7,000 |
| Example 65 | Compound 23 | D-2 | 5.5 | 8.0 | Blue | 7,000 |
| Example 66 | Compound 24 | D-2 | 5.7 | 7.6 | Blue | 7,000 |
| Example 67 | Compound 25 | D-2 | 5.5 | 8.2 | Blue | 8,000 |
| Example 68 | Compound 26 | D-2 | 5.6 | 8.2 | Blue | 8,000 |
| Example 69 | Compound 27 | D-2 | 5.5 | 7.8 | Blue | 8,000 |
| Example 70 | Compound 28 | D-2 | 5.6 | 7.8 | Blue | 8,000 |
| Example 71 | Compound 29 | D-2 | 5.5 | 8.0 | Blue | 8,000 |
| Example 72 | Compound 30 | D-2 | 5.5 | 8.0 | Blue | 8,000 |
| Example 73 | Compound 31 | D-2 | 5.5 | 7.6 | Blue | 7,000 |
| Example 74 | Compound 32 | D-2 | 5.5 | 7.6 | Blue | 7,000 |
| Example 75 | Compound 33 | D-2 | 5.5 | 7.6 | Blue | 7,000 |
| Example 76 | Compound 34 | D-2 | 5.5 | 7.6 | Blue | 7,000 |
| Example 77 | Compound 35 | D-2 | 5.5 | 7.6 | Blue | 7,000 |
| Example 78 | Compound 36 | D-2 | 5.5 | 7.8 | Blue | 7,000 |
| Example 79 | Compound 37 | D-2 | 5.5 | 7.5 | Blue | 6,000 |
| Example 80 | Compound 38 | D-2 | 5.6 | 7.5 | Blue | 6,000 |
| Comparative Example 17 | Compound A | D-2 | 5.6 | 6.7 | Blue | 3,000 |
| Comparative Example 18 | Compound B | D-2 | 5.7 | 6.8 | Blue | 4,000 |
| Comparative Example 19 | Compound C | D-2 | 6 | 5.7 | Bluish green | 200 |
| Comparative Example 20 | Compound D | D-2 | 6.3 | 6.2 | Blue | 3,000 |
| Comparative Example 21 | Compound E | D-2 | 6.3 | 6.2 | Blue | 2,000 |
| Comparative Example 22 | Compound F | D-2 | 6.3 | 6.2 | Blue | 2,000 |
| Comparative Example 23 | Compound G | D-2 | 6.3 | 6.2 | Blue | 2,000 |
| Comparative Example 24 | Compound H | D-2 | 6.3 | 6.2 | Blue | 1,000 |

Example 81 to Example 84

Organic EL devices were each produced in the same manner as in Example 43 except that any one of Compounds 39 to 42 shown above was used instead of Compound 1. Table 4 shows the results.

TABLE 4

| | Host | Dopant | Voltage (V) | Current efficiency (cd/A) | Luminescent color | Lifetime |
|---|---|---|---|---|---|---|
| Example 81 | Compound 39 | D-2 | 5.7 | 8.0 | Blue | 9,000 |
| Example 82 | Compound 40 | D-2 | 5.7 | 7.7 | Blue | 7,000 |
| Example 83 | Compound 41 | D-2 | 5.5 | 8.2 | Blue | 9,000 |
| Example 84 | Compound 42 | D-2 | 5.6 | 7.7 | Blue | 7,000 |

The above results show that an organic EL device using any one of the compounds of the present invention each using a benzofuran or benzothiophene derivative (Examples 1 to 84) has a higher current efficiency than that of an organic EL device using any one of Compounds D to H each containing neither benzofuran nor benzothiophene (Comparative Examples 1 to 24). In addition, comparison between each of those compounds of the present invention and Comparative Compound A (Comparative Example 1) reveals that the insertion of an arylene group between anthracene and dibenzofuran specifically improves the efficiency of an organic EL device using any one of the compounds of the present invention. Further, the insertion of an arylene group between anthracene and dibenzofuran or dibenzothiophene lengthens the lifetime of an organic EL device using any one of the compounds of the present invention. While the highest occupied molecular orbital (HOMO) and lowest unoccupied molecular orbital (LUMO) of a compound based on the system of the present invention into which arylene has been inserted remain on anthracene and the arylene group directly bonded to anthracene, the HOMO and LUMO of a compound based on a system in which dibenzofuran is directly bonded to anthracene reach a dibenzofuranyl group. As a result, when an organic EL device using a compound based on the system in which dibenzofuran is directly bonded to anthracene is driven with a current, a dibenzofuranyl group contributes to the oxidation/reduction of the compound, so the substituent may decompose to shorten the lifetime of the device.

In addition, comparison between Compound B (Comparative Example 2) and any one of the compounds of the present invention reveals that an organic EL device using any one of the compounds of the present invention has a longer lifetime than that of an organic EL device using Compound B. The following has been known: when an organic EL device using any one of those material systems is driven with a current, the compound is brought into an excited state, and anthracene and a substituent of anthracene change so as to adopt a planar structure. From this viewpoint, an excited state of a 1-naphthyl group is unstable owing to a short distance between anthracene and a hydrogen atom of the naphthyl group while an excited state of a phenyl group or 2-naphthyl group is stable. As a result, a 1-naphthyl group exerts a shortening effect on the lifetime of an organic EL device using a compound containing the 1-naphthyl group, and the effect appears remarkably in a compound based on the system of the present invention.

Further, an organic EL device containing a dibenzofuran-based compound out of the compound group of the present invention has a particularly long lifetime. This is probably because dibenzofuran is more stable against oxidation/reduction than dibenzothiophene is.

Examples 43 to 80 show that, when an electron transporting material capable of exerting its function at a low voltage is used, an organic EL device using a system having a diphenylanthracene skeleton out of the materials based on the system of the present invention specifically has high efficiency and a long lifetime.

In addition, it is clear that the material of the present invention is a material capable of realizing the lengthening of the lifetime of an organic EL device specifically as compared to a compound disclosed in WO 2005/113531.

As can be seen from the foregoing, the anthracene derivative of the present invention is useful as a material for an organic EL device because the derivative can realize higher efficiency and a longer lifetime than those realized by a material system that has been conventionally used.

INDUSTRIAL APPLICABILITY

As described above in detail, an organic EL device using the anthracene derivative of the present invention as a material for an organic EL device has high luminous efficiency and a long lifetime. Accordingly, the device is extremely useful as an organic EL device with high practicality.

The invention claimed is:

1. An anthracene derivative represented by the following general formula (2):

(2)

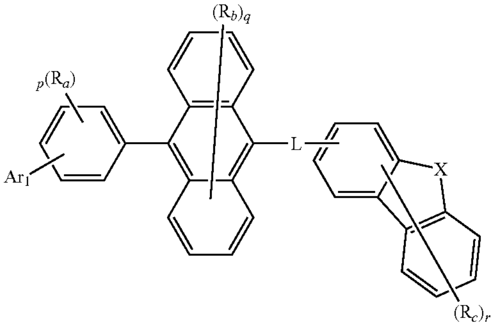

where L represents an unsubstituted naphthylene group, a methyl group substituted or unsubstituted fluorenylene group, or an unsubstituted biphenylene group, $R_a$ to $R_c$ each represent a hydrogen atom, $Ar_1$ represents a naphthyl group or phenanthryl group, X represents an oxygen atom (O) or a sulfur atom (S), p represents an integer of 4, q represents an integer of 8, and r represents an integer of 7.

2. The anthracene derivative according to claim 1, wherein the anthracene derivative is represented by the following general formula (4):

(4)

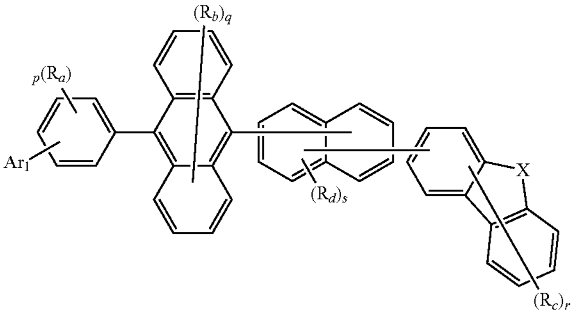

where Ra to Rd each represent a hydrogen atom, $Ar_1$ represents a naphthyl group or phenauthryl group, X represents an oxygen atom (O) or a sulfur atom (S), p represents an integer of 4, q represents an integer of 8, r represents an integer of 7, and s represents an integer of 6.

3. The anthracene derivative according to claim 1, wherein the anthracene derivative is represented by the following general formula (5):

(5)

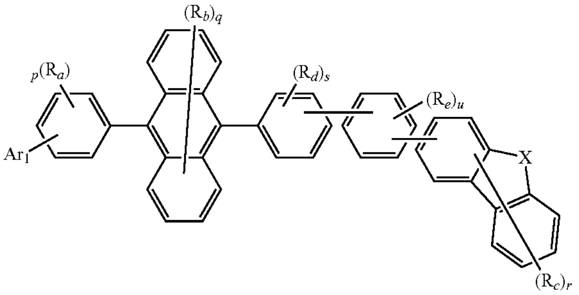

where $R_a$ to $R_e$ each represent a hydrogen atom, $Ar_1$ represents a naphthyl group or phenanthryl group, X represents an oxygen atom (O) or a sulfur atom (S), p represents an integer of 4, q represents an integer of 8, r represents an integer of 7, s represents an integer of 4, and u represents an integer of 4.

4. The anthracene derivative according to claim 1, the anthracene derivative is represented by the following general formula (6):

(6)

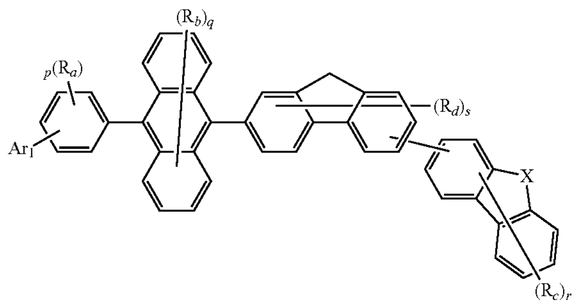

where $R_a$ to $R_d$ each represent a hydrogen atom, $R_d$ represents a hydrogen atom or methyl group, $Ar_1$ represents a naphthyl group or phenanthryl group, X represents an oxygen atom (O) or a sulfur atom (S), p represents an integer of 4, q represents an integer of 8, r represents an integer of 7, and s represents an integer of 1 to 8.

5. The anthracene derivative according to claim 1, wherein the L is bonded to 2-position or 4-position in the following structure or the general formula (2):

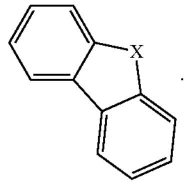

6. The anthracene derivative according to claim 1, wherein $Ar_1$ represents a 1-naphthyl group or a 2-naphthyl group.

7. The anthracene derivative according to claim 1, wherein $Ar_1$ represents a 9-phenanthyl group.

8. The anthracene derivative according to claim 1, wherein X represents an oxygen atom.

9. A material for an organic electroluminescence device, comprising the anthracene derivative according to claim 1.

10. A light emitting material for an organic electroluminescence device, comprising the anthracene derivative according to claim 1.

11. An organic electroluminescence device comprising an organic thin film layer formed of one or plural layers including at least a light emitting layer, the organic thin film layer being interposed between a cathode and an anode, wherein at least one layer of the organic thin film layer contains the anthracene derivative according to claim 1 alone or as a component of a mixture.

12. An organic electroluminescence device according to claim 11, wherein the light emitting layer contains the anthracene derivative as a light emitting material.

13. An organic electroluminescence device according to claim 11, wherein the light emitting layer contains the anthracene derivative as a host material.

14. An organic electroluminescence device according to claim 11, wherein the light emitting layer further contains a fluorescent or phosphorescent dopant.

15. An organic electroluminescence device according to claim 14, wherein the fluorescent dopant comprises an arylamine compound and/or an aryldiamine compound.

16. An organic electroluminescence device according to claim 14, wherein the fluorescent dopant comprises a styrylamine compound and/or a styryldiamine compound.

17. An organic electroluminescence device according to claim 14, wherein the fluorescent dopant comprises an aromatic amine compound and/or an aromatic diamine compound.

18. An organic electroluminescence device according to claim 14, wherein the fluorescent dopant comprises a fused polycyclic aromatic compound (except amine compounds).

19. An organic electroluminescence device according to claim 14, wherein the phosphorescent dopant comprises a metal complex compound.

* * * * *